(12) United States Patent
Kwon et al.

(10) Patent No.: US 11,717,480 B2
(45) Date of Patent: Aug. 8, 2023

(54) EXTRACELLULAR VESICLES AND METHODS AND USES THEREOF

(71) Applicant: The Regents of the University of California, Oakland, CA (US)

(72) Inventors: Young Jik Kwon, Irvine, CA (US); Dominique Antoinette Ingato, Toms River, NJ (US)

(73) Assignee: The Regents of the University of California, Oakland, CA (US)

( * ) Notice: Subject to any disclaimer, the term of this patent is extended or adjusted under 35 U.S.C. 154(b) by 1105 days.

(21) Appl. No.: 16/465,423

(22) PCT Filed: Nov. 30, 2017

(86) PCT No.: PCT/US2017/064062
§ 371 (c)(1),
(2) Date: May 30, 2019

(87) PCT Pub. No.: WO2018/102608
PCT Pub. Date: Jun. 7, 2018

(65) Prior Publication Data
US 2019/0350854 A1 Nov. 21, 2019

Related U.S. Application Data

(60) Provisional application No. 62/428,407, filed on Nov. 30, 2016.

(51) Int. Cl.
*A61K 9/127* (2006.01)
*A61K 31/704* (2006.01)
*A61K 9/00* (2006.01)
*A61K 47/69* (2017.01)
*C12N 5/0784* (2010.01)
*C12N 5/09* (2010.01)

(52) U.S. Cl.
CPC .......... *A61K 9/1271* (2013.01); *A61K 9/0019* (2013.01); *A61K 9/1277* (2013.01); *A61K 31/704* (2013.01); *A61K 47/6901* (2017.08); *C12N 5/0639* (2013.01); *C12N 5/0693* (2013.01); *C12N 2500/30* (2013.01); *C12N 2500/44* (2013.01); *C12N 2500/60* (2013.01)

(58) Field of Classification Search
CPC .............. A61K 9/1271; A61K 47/6901; A61K 9/0019; A61K 9/1277; A61K 31/704; C12N 5/0639; C12N 5/0693; C12N 2500/30; C12N 2500/44; C12N 2500/60
See application file for complete search history.

(56) References Cited

U.S. PATENT DOCUMENTS

2011/0143385 A1* 6/2011 Bauer ............... C12N 1/066
435/375
2012/0177574 A1* 7/2012 Gho ..................... A61K 35/545
424/9.1

FOREIGN PATENT DOCUMENTS

| WO | 2016133254 | | 8/2016 | | |
|----|------------|---|--------|---|---|
| WO | WO-2016123556 A1 | * | 8/2016 | ........... | A61K 31/685 |
| WO | 2017161010 | | 9/2017 | | |
| WO | 2020037303 A1 | | 2/2020 | | |
| WO | 2020180744 A1 | | 9/2020 | | |

OTHER PUBLICATIONS

Akao et al., "Microvesicle-mediated RNA Molecule Delivery System Using Monocytes/Macrophages." Molecular Therapy. 19(2):395-399 (2011).
Akers et al., "Biogenesis of extracellular vesicles (EV): exosomes, microvesicles, retrovirus-like vesicles, and apoptotic bodies." J Neurooncol 113:1-11 (2013).
Albanese et al., "Biologically Active Fas Antigen and Its Cognate Ligand Are Expressed on Plasma Membrane-Derived Extracellular Vesicles." Blood. 91(10):3862-3874 (May 15, 1998).
Allen et al., "Drug Delivery Systems: Entering the Mainstream." Science 303:1818 (2004).
Alvarez-Erviti et al., "Delivery of siRNA to the mouse brain by systemic injection of targeted exosomes." Nature Biotechnology 29(4):341-347 (2011).
Armeanu et al., "Natural Killer Cell-Mediated Lysis of Hepatoma Cells via Specific Induction of NKG2D Ligands by the Histone Deacetylase Inhibitor Sodium Valproate" Cancer Res 65(14):6321-6329 (2005).
Bailey et al., "The Role of Sulphydryl Groups in the Interaction of Myosin and Actin." Biochimica Et Biophysica Acta 1:506-516 (1947).
Baj-Kryworzeka et al., "Tumour-derived microvesicles carry several surface determinants and mRNA of tumour cells and transfer some of these determinants to monocytes " Cancer Immunol Immunother 55:808-818 (2006).
Bangham et al., "Negative Staining of Phospholipids and their Structural Modification by Surface-active Agents as observed in the Electron Microscope." J. Mol. Biol. 8:660-668 (1964).
Barry et al., "Determining the Effects of Lipophilic Drugs on Membrane Structure by Solid-State NMR Spectroscopy: The Case of the Antioxidant Curcumin." J. Am. Chem. Soc. 131:4490-4498 (2009).
Boron et al., "Intracellular pH Transients in Squid Giant Axons Caused by $CO_2$, $NH_3$, and Metabolic Inhibitors." The Journal of General Physiology 67:91-112 (1976).
Bosma et al., "The SCID Mouse Mutant: Definition, Characterization, and Potential Uses." Ann. Rev. Immunol. 9:323-50 (1991).
Braicu et al., "Exosomes as divine messengers: are they the Hermes of modem molecular oncology?" Cell Death and Differentiation 22:34-45 (2015).

(Continued)

*Primary Examiner* — Michael P Cohen
(74) *Attorney, Agent, or Firm* — Gavrilovich, Dodd & Lindsey LLP

(57) ABSTRACT

Extracellular vesicles, their manufacture, and methods of treatment are described. Generally, extracellular vesicles can be generated by applying sulfhydryl blocking reagents on animal cells. Extracellular vesicles can be loaded with compounds for an intended use, such as, for example, loading an extracellular vesicle with a medicament to treat an animal. As described here, extracellular vesicles can be generated in a large scale and used for personalized treatments.

20 Claims, 27 Drawing Sheets

(56) References Cited

OTHER PUBLICATIONS

Braunsmann et al., "High-speed force mapping on living cells with a small cantilever atomic force microscope." Review of Scientific Instruments 85:073703 (2014).
Brown et al., "Gene delivery with synthetic (non viral) carriers." International Journal of Pharmaceutics 229:1-21 (2001).
Bruno et al., "Microvesicles Derived from Mesenchymal Stem Cells Enhance Survival in a Lethal Model of Acute Kidney Injury" PLoS ONE 7(3):e33115 (2012).
Caby et al., "Exosomal-like vesicles are present in human blood plasma." International Immunology. 17(7):879-887 (2005).
Cai et al., "Activated T Cell Exosomes Promote Tumor Invasion via Fas Signaling Pathway." J Immunol 188(12):5954-5961 (2012).
Camussi et al., "Exosome/microvesicle-mediated epigenetic reprogramming of cells." Am J Cancer Res 1(1):98-110 (2011).
Cantaluppi et al., "Microvesicles derived from endothelial progenitor cells protect the kidney from ischemia-reperfusion injury by microRNA-dependent reprogramming of resident renal cells." Kidney International 82:412-427 (2012).
Chaput et al., "Exosome-based immunotherapy." Cancer Immunol Immunother 53:234-239 (2004).
Chaput et al., "Exosomes: immune properties and potential clinical implementations." Semin Immunopathol 33:419-440 (2011).
Charras et al., "Non-equilibration of hydrostatic pressure in blebbing cells." Nature Letters 435:365-369 (2005).
Charras et al., "Reassembly of contractile actin cortex in cell blebs." The Journal of Cell Biology, 175,(3):477-490. (2006).
Charras et al., "Blebs lead the way: how to migrate without lamellipodia." Nature Reviews 9:730-736 (2008).
Chen et al., "Microfluidic isolation and transcriptome analysis of serum microvesicles." Lab Chip 10:505-511 (2010).
Cocucci et al., "Shedding microvesicles: artefacts no more." Trends in Cell Biology 19(2):43-51 (2009).
Cullis et al., "Generating and loading of liposomal systems for drug-delivery applications." Advanced Drug Delivery Reviews 3:67-282 (1989).
Dalle-Donne et al., "The Actin Cytoskeleton Response to Oxidants: From Small Heat Shock Protein Phosphorylation to Changes in the Redox State of Actin Itself." Free Radical Biology & Medicine, 31(12):1624-1632, (2001).
De Jong et al., "Cellular stress conditions are reflected in the protein and RNA content of endothelial cell-derived exosomes." J Extracell Vesicles 1 (Apr. 16, 2012).
Distler et al., "Microparticles as Regulators of Inflammation." Arthritis & Rheumatism 52(11):3337-3348 (2005).
Dolo et al., "Enrichment and localization of ganglioside GD3 and caveolin-1 in shed tumor cell membrane vesicles." Biochimica et Biophysica Acta 1486:265-274 (2000).
Edwards et al., "Spontaneous Vesicle Formation at Lipid Bilayer Membranes." Biophysical Journal 71:1208-1214 (1996).
El Andaloussi et al., "Extracellular vesicles: biology and emerging therapeutic opportunities." Nature Reviews 12:347-357 (2013).
El Aneed, Anas. "An overview of current delivery systems in cancer gene therapy." Journal of Controlled Release 94 1-14 (2004).
Elmore, Susan. "Apoptosis: A Review of Programmed Cell Death." Toxicol Pathol. 35(4):495-516 (2007).
Erickson, Harold P. "Size and Shape of Protein Molecules at the Nanometer Level Determined by Sedimentation, Gel Filtration, and Electron Microscopy." Biological Procedures Online 11(1):32-51 (2009).
Fackler et al., "Cell motility through plasma membrane blebbing." J. Cell Biol. 181(6):879-884 (2008).
Fang et al., "The EPR effect: Unique features of tumor blood vessels for drug delivery, factors involved, and limitations and augmentation of the effect" Advanced Drug Delivery Reviews 63:136-151 (2011).
Faure et al., "Exosomes are released by cultured cortical neurones." J. Mol. Cell. Neurosci. 31:642-648 (2006).
Fevrier et al., "Exosomes: endosomal-derived vesicles shipping extracellular messages." Current Opinion in Cell Biology 16:415-421 (2004).
Fox et al., "Formaldehyde Fixation." The Journal of Histochemistry and Cytochemistry 33(8):845-853 (1985).
Fritze et al., "Remote loading of doxorubicin into liposomes driven by a transmembrane phosphate gradient." Biochimica et Biophysica Acta 1758:1633-1640 (2006).
Fuhrmann et al., "Cell-derived vesicles for drug therapy and diagnostics: Opportunities and challenges." Nano Today 10:397-409 (2015).
Gabizon et al., "Dose Dependency of Pharmacokinetics and Therapeutic Efficacy of Pegylated Liposomal Doxorubicin (DOXIL) in Murine Models" Journal of Drug Targeting 10 (7):539-548 (2002).
Ganta et al., "A review of stimuli-responsive nanocarriers for drug and gene delivery." Journal of Controlled Release 126:187-204 (2008).
Gatti et al., "Microvesicles derived from human adult mesenchymal stem cells protect against ischaemia-reperfusion-induced acute and chronic kidney injury." Nephrol Dial Transplant 26:1474-1483 (2011).
Gesierich et al., "Systemic Induction of the Angiogenesis Switch by the Tetraspanin D6.1A/CO-029." Cancer Res 66:(14):7083-7094 (2006).
Giacca et al., "Virus-mediated gene delivery for human gene therapy." Journal of Controlled Release 161: 377-388 (2012).
Gupta et al., "Dietary antioxidant curcumin inhibits microtubule assembly through tubulin binding." FEBS Journal 273:5320-5332 (2006).
Abels et al., "Introduction to Extracellular Vesicles: Biogenesis, RNA Cargo Selection, Content, Release, and Uptake." Cell Mol Neurobiol 36:301-312 (2016).
Abramowicz et al., "Proteomic analysis of exosomal cargo: the challenge of high purity vesicle isolation." Molecular Biosystems 12:1407-1419 (2016).
Admyre et al., "Direct exosome stimulation of peripheral human T cells detected by ELISPOT." Eur. J. Immunol. 36:1772-1781 (2006).
Albanese et al., "The Effect of Nanoparticle Size, Shape, and Surface Chemistry on Biological Systems." Annu. Rev Biomed. Eng. 14:1-16 (2012).
Alhasan et al., "Exosome Encased Spherical Nucleic Acid Gold Nanoparticle Conjugates as Potent MicroRNA Regulation Agents." Small. 10(1): 86-192. (2014).
Alvarez et al., "Comparison of protein, microRNA, and mRNA yields using different methods of urinary exosome isolation for the discovery of kidney biomarkers." Kidney International 82:1024-1032 (2012).
Andaloussi et al., "Extracellular vesicles: biology and emerging therapeutic opportunities." Nature Reviews Drug Discovery 12:347-357 (2013).
Ariga et al., "Bioinspired Nanoarchitectonics as Emerging Drug Delivery Systems." New Journal of Chemistry 38:5120-5121 (2013).
Arslan et al., "Mesenchymal stem cell-derived exosomes increase ATP levels, decrease oxidative stress and activate PI3K/Akt pathway to enhance myocardial viability and prevent adverse remodeling after myocardial ischemia/reperfusion injury." Stem Cell Research 10:301-312 (2013).
Aspe et al., "Enhancement of Gemcitabine sensitivity in adenocarcinoma by novel exosome-mediated delivery of the Survivin-T34A mutant." Journal of Extracellular Vesicles 3(1):23244 (2014).
Aubertin et al., "Massive release of extracellular vesicles from cancer cells after photodynamic treatment or chemotherapy." Scientific Reports 6:35376 (2016).
Bartolini et al., "Recombinant outer membrane vesicles carrying Chlamydia muridarum HtrA induce antibodies that neutralize chlamydial infection in vitro" Journal of Extracellular Vesicles 2(1):20181 (2013).
Benedikter et al., "Redox-dependent thiol modifications: implications for the release of extracellular vesicles." Cellular and Molecular Life Sciences 75:2321-2337 (2018).
Bhatnagar et al., "Exosomes released from macrophages infected with intracellular pathogens stimulate a proinflammatory response in vitro and in vivo." Blood 110(9):3234-3244 (2007).

(56) References Cited

OTHER PUBLICATIONS

Blanco et al., "Principles of nanoparticle design for overcoming biological barriers to drug delivery." Nat Biotechnol. 33(9):941-951 (2015).

Bobrie et al., "Diverse subpopulations of vesicles secreted by different intracellular mechanisms are present in exosome preparations obtained by differential ultracentrifugation" Journal of Extracellular Vesicles 1(1):8397 (2012).

Bosch et al., "Trehalose prevents aggregation of exosomes and cryodamage." Scientific Reports 6:36162 (2016).

Bunker et al., "Rational design of liposomal drug delivery systems, a review: Combined experimental and computational studies of lipid membranes, liposomes and their PEGylation." Biochimica et Biophysica Acta 1858:2334-2352 (2016).

Carvalho et al., "Doxorubicin: The Good, the Bad and the Ugly Effect." Current Medicinal Chemistry 16:3267-3285 (2019).

Charras et al., "Life and Times of a Cellular Bleb." Biophysical Journal vol. 94:1836-1853 (2008).

Chen et al., "Collateral Damage in Cancer Chemotherapy: oxidative stress in nontargeted tissues." Molecular Intervention 7(3):146-156 (2007).

Chen et al., "Chemokine-Containing Exosomes are Released from Heat-Stressed Tumor Cells via Lipid Raft-Dependent Pathway and Act as Efficient Tumor Vaccine." Journal of Immunology 186:2219-2228 (2011).

Cheng et al., "Exosomes carrying mycobacterial antigens can protect mice against an M. tuberculosis Infection." 43(12):3279-3290 (2013).

Christianson et al., "Cancer cell exosomes depend on cell-surface heparan sulfate proteoglycans for their internalization and functional activity." PNAS 110(43):17380-17385(2013).

Clayton et al., "Induction of heat shock proteins in B-cell exosomes." Journal of Cell Science 118(16):3631-3638 (2005).

Colino et al., "Exosomes from Bone Marrow Dendritic Cells Pulsed with Diphtheria Toxoid Preferentially Induce Type 1 Antigen-Specific IgG Responses in Naive Recipients in the Absence of Free Antigen." J Immunol 177:3757-3762 (2006).

Colombo et al., "Biogenesis, Secretion, and Intercellular Interactions of Exosomes and Other Extracellular Vesicles." Annu. Rev. Cell Dev. Biol . . . 30:255-289 (2014).

Conde-Vancells et al., "Characterization and Comprehensive Proteome Profiling of Exosomes Secreted by Hepatocytes." J Proteome Res. 7(12):5157-5166 (2008).

Crescitelli et al., "Distinct RNA profiles in subpopulations of extracellular vesicles: apoptotic bodies, microvesicles and exosomes." Journal of Extracellular Vesicles 2(1):20677 (2013).

Daraee et al., "Application of liposomes in medicine and drug delivery." Artificial Cells, Nanomedicine, and Biotechnology 44: 381 391 (2016).

Del Cacho et al., "Induction of Protective Immunity against Eimeria tenella, Eimeria maxima, and Eimeria acervulina infections Using Dendritic Cell-Derived Exosomes." Infection and Immunity 80(5):1909-1916 (2012).

Dodson et al., "Challenges in the translation and commercialization of cell therapies." BMC Biotechnology 15:70 (2015).

Dragovic et al., "Sizing and phenotyping of cellular vesicles using Nanoparticle Tracking Analysis." Nanomedicine Nanotechnology, Biology, and Medicine 7:780-788 (2011).

Enderle et al., "Characterization of RNA from Exosomes and Other Extracellular Vesicles Isolated by a Novel Spin Column-Based Method." Plos One 10(8): e0136133.

Evans et al., "Physical Properties of Surfactant Bilayer Membranes: Thermal Transitions, Elasticity, Rigidity, Cohesion, and Collodial Interactions." Journal Physical Chemistry 91:4219-4228 (1987).

Fang et al., "Tumor-derived exosomal miR-1247-3p induces cancer-associated fibroblast activation to foster lung metastasis of liver cancer." Nature Communications 9(191):1-13 (2018).

Fishkind et al., "Microinjection of the Catalytic Fragment of Myosin Light Chain Kinase into Dividing Cells: Effects on Mitosis and Cytokinesis." The Journal of Cell Biology 114(5):967-975 (1991).

Friedl et al., "Tumour-Cell Invasion and Migration: Diversity and Escape Mechanisms." Nature Reviews 3:362-374 (2003).

Fuhrmann et al., "Active loading into extracellular vesicles significantly improves the cellular uptake and photodynamic effect of porphyrins" Journal of Controlled Release 205:35-44 (2015).

Gangoda et al., "Cortactin enhances exosome secretion without altering cargo." The Journal of Cell Biology 214 (2):129-131.

Garay et al., "Antibodies against polyethylene glycol in healthy subjects and in patients treated with PEG-conjugated agents." Expert Opinion Drug Development 9(11):1319-23 (2012).

Gardiner et al., "Extracellular vesicle sizing and enumeration by nanoparticle tracking analysis." Journal of Extracellular Vesicles 2:(1):19671 (2013).

Gilleron et al., "Image-based analysis of lipid nanoparticle-mediated siRNA delivery, intracellular trafficking and endosomal escape." Nature Biotechnology 31:638-646 (2013).

Goodwin et al., "Single-Dose Toxicity Study of Hepatic Intra-arterial Infusion of Doxorubicin Coupled to a Novel Magnetically Targeted Drug Carrier." Toxicological Sciences 60:177-183 (2001).

Gudbergsson et al., "Systematic review of factors influencing extracellular vesicle yield from cell cultures." Cytotechnology 68:579-592 (2016).

Hadla et al., "Exosomes increase the therapeutic index of doxorubicin in breast and ovarian cancer mouse models." Nanomedicine 11(18)2431-41 (2016).

Haney et al., "Exosomes as Drug Delivery Vehicles for Parkinson's Disease Therapy." J Control Release 207:18-30 (2015).

Hannun Y. "Apoptosis and the Dilemma of Cancer Chemotherapy." Blood 89(6):1845-1853 (1997).

He et al., "Integrated immunoisolation and protein analysis of circulating exosomes using microfluidic technology." Lab Chip 14:3773-80 (2014).

Heathman et al., "The translation of cell-based therapies: clinical landscape and manufacturing challenges." Regen. Med. 10(1):49-64 (2015).

Kesimer et al., "Physical Characterization and profiling of airway epithelial derived exosomes using light scattering," Methods, 87:59-63 (2015).

Momen-Heravi et al., "Current methods for the isolation of extracellular vesicles." Biological Chemistry 394(10) 1253-1262(2013).

Scott et al., "Undifferentiated and differentiated L6 myoblast plasma membranes. I: Comparison of the morphology of plasma membrane vesiculation and the factors influencing the vesiculation process," Cell Differentiation, 7 (6):325-334 (1978).

Thomas, Shane. International Search Report and Written Opinion for PCT/US17/64062. Feb. 23, 2018.

Thureson-Klein et al., "Morphological effects of osmolarity on purified noradrenergic vesicles" Journal of Neurocytology 4(5):609-627 (1975).

Weiss, Marie-France. Supplementary European Search Report for EP17875424. Jun. 24, 2020.

Riteau et al., "Exosomes Bearing HLA-G are Released by Melanoma Cells." Human Immunology 64:1064-1072 (2003).

Savina et al., "Exosome Release is Regulated by a Calcium-dependent Mechanism in K562 Cells." The Journal of Biological Chemistry 278(22):20083-20090 (2003).

Scott, R.E., "Plasma Membrane Vesiculation: A New Technique for Isolation of Plasma Membranes." Science 194 (4266):743-5 (1976).

Scott et al., "Plasma Membrane Vesiculation in 3T3 and SV3T3 Cells." J. Cell Sci. 35:229-243 (1979).

Sezgin et al., "Elucidating membrane structure and protein behavior using giant plasma membrane vesicles." Nature Protocols, 7(6):1042-1051 (2012).

Silva et al., "Cell-derived vesicles as a bioplatform for the encapsulation of theranostic nanomaterials." Nanoscale, 5:11374-11384 (2013).

Simon et al., "Intracellular pH and the control of multidrug resistance." Proc. Natl. Acad. Sci. USA 91:1128-1132 (1994).

Simpson et al., "Extracellular Microvesicles: The need for Internationally Recognized Nomenclature and Stringent Purification Criteria" J. Proteomics Bioinform 5:2 (2012).

(56) References Cited

OTHER PUBLICATIONS

Skog et al., "Glioblastoma microvesicles transport RNA and protein that promote tumor growth and provide diagnostic biomarkers." Nat Cell Biol. 10(12):1470-1476 (2008).

Skokos et al., "Mast Cell-Derived Exosomes Induce Phenotypic and Functional Maturation of Dendritic Cells and Elicit Specific Immune Responses In Vivo." The Journal of Immunology 170(6):3037-3045 (2003).

Smith et al., "Extracellular Vesicles Commercial Potential as Byproducts of Cell Manufacturing for Research and Therapeutic Use." BioProcess International (2015).

Smyth et al., "Biodistribution and delivery efficiency of unmodified tumor-derived exosomes." Journal of Controlled Release 199:145-155 (2015).

Steinherz et al., "Antileukemia Activity of a Natural Killer Cell Line against Human Leukemias." Clinical Cancer Research. 4:2859-2868 (1998).

Stoorvogel et al., "The Biogenesis and Functions of Exosomes." Traffic 3:321-330 (2002).

Sun et al., "A Novel Nanoparticle Drug Delivery System: The Anti-inflammatory Activity of Curcumin Is Enhanced When Encapsulated in Exosomes." Molecular Therapy 18(9):1606-1614 (2010).

Szajnik et al., "Tumor-Derived Microvesicles Induce, Expand and Up-Regulate Biological Activities of Human Regulatory T Cells (Treg)" PLoS ONE 5(7):e11469 (2010).

Tan et al., "Cell or Cell Membrane-Based Drug Delivery Systems." Theranostics 5(8)863-881 (2015).

Taverna et al., "Exosomal shuttling of miR-126 in endothelial cells modulates adhesive and migratory abilities of chronic myelogenous leukemia cells." Molecular Cancer 13:169 (2014).

Taylor et al., "Apoptosis: controlled demolition at the cellular level." Molecular Cell Biology 9:231-241 (2008).

Thery et al., "Exosomes: Composition, Biogenesis and Function." Immunology 2:560-579 (2002).

Thery, C. "Isolation and Characterization of Exosomes from Cell Culture Supernatants and Biological Fluids." Curr Protoc Cell Biol. Chapter 3:Unit 3.22 (2006).

Thery et al., "Membrane vesicles as conveyors of immune responses." Immunology 9:581-593 (2009).

Thomas et al., "Progress and problems with the use of viral vectors for gene therapy." Nature Reviews Genetics, 4:346-358 (2003).

Tian et al., "A doxorubicin delivery platform using engineered natural membrane vesicle exosomes for targeted tumor therapy." Biomaterials 35:2383e2390 (2014).

Tinevez et al., "Role of cortical tension in bleb growth." Proceedings in the National Academy of Sciences 106 (44):18581-18586 (2009).

Torgerson et al., "The actin-myosin cytoskeleton mediates reversible agonist-induced membrane blebbing." Journal of Cell Science 111:2911-2922 (1998).

Valadi et al., "Exosome-mediated transfer of mRNAs and microRNAs is a novel mechanism of genetic exchange between cells." Nature Cell Biology 9(6) (2007).

Van Den Boorn et al., "SiRNA delivery with exosome nanoparticles." Nature Biotechnology 29(4):325-326 (2011).

Van_Dommelen et al., "Microvesicles and exosomes: Opportunities for cell-derived membrane vesicles in drug delivery." Journal of Controlled Release 161:635-644 (2012).

Vivier et al., "Functions of Natural Killer Cells." Nature Immunology 9(5):503-510 (2008).

Vlassov et al., "Exosomes: Current knowledge of their composition, biological functions, and diagnostic and therapeutic potentials." Biochimica et Biophysica Acta 1820:940-948 (2012).

Wahlgren et al., "Plasma exosomes can deliver exogenous short interfering RNA to monocytes and lymphocytes." Nucleic Acids Research 40(17):e130 (2012).

Warren et al., "NK cells and apoptosis." Immunology and Cell Biology 77:64-75 (1999).

Wennerberg et al., "Doxorubicin sensitizes human tumor cells to NK cell- and T-cell-mediated killing by augmented TRAIL receptor signaling." Int. J. Cancer. 133:1643-1653 (2013).

Whitford et al., "Continuous Production of Exosomes Utilizing the Technical Advantages of Hollow-Fiber Bioreactor Technology." Genetic Engineering & Biotechnology News 35(16) (2015).

Wysoczynski et al., "Lung cancer secreted microvesicles: Underappreciated modulators of microenvironment in expanding tumors." Int J. Cancer. 125:1595-1603 (2009).

Zeng et al., "Determination of the lowest concentrations of aldehyde fixatives for completely fixing various cellular structures by real-time imaging and quantification." Histochem Cell Biol 139:735-749 (2013).

Zhang et al., "Comparison in the effects of IL-2, IL-12, IL-15 and IFN$\alpha$ on gene regulation of granzymes of human NK cell line NK-92." International Immunopharmacology. 8:989-996 (2008).

Zhao et al., "Magnetite nanoparticles as smart carriers to manipulate the cytotoxicity of anticancer drugs: magnetic control and pH-responsive release " J. Mater. Chem., 22:15717 (2012).

Xu et al., "Extracellular vesicle isolation and characterization: toward clinical application." The Journal of Clinical Investigation 126(4): 1152-1162 (2016).

Yamashita et al., "Effects of Exosome Isolation Methods on Physicochemical Properties of Exosomes and Clearance of Exosomes from the Blood Circulation." Eur J Pharm Biopharm 98:1-8 (2016).

Yang et al. "Current Advances of Lanthanide Ion (Ln3+)-Based Upconversion Nanomaterials for Drug Delivery." Chemical Society Reviews 44:1416-1448 (2015).

Yeatts et al., "Bioreactors to Influence Stem Cell Fate: Augmentation of Mesenchymal Stem Cell Signaling Pathways via Dynamic Culture Systems." Biochim Biophys Acta. 1830(2): 2470-2480 (2013).

Yu et al., "Exosomes Secreted from GATA-4 Overexpressing Mesenchymal Stem Cells Serve as a Reservoir of Anti-Apoptotic microRNAs for Cardioprotection." Int J Cardiol. 182: 349-360 (2015).

Yuan et al., "Macrophage Exosomes as Natural Nanocarriers for Protein Delivery to Inflamed Brain." Biomaterials. 142:1-12 (2017).

Yuana et al., "Co-isolation of extracellular vesicles and high-density lipoproteins using density gradient ultracentrifugation." Journal of Extracellular Vesicles 3:23262 (2014).

Zaborowski et al., "Extracellular Vesicles: Composition, Biological Relevance, and Methods of Study." BioScience 65(8):783-797 (2015).

Zhang et al., "Comparison of ultracentrifugation and density gradient separation methods for isolating Tca8113 human tongue cancer cell line-derived exosomes." Oncology Letters 8: 1701-1706 (2014).

Zhang et al., "Exosome and Exosomal MicroRNA: Trafficking, Sorting, and Function." Genomics Proteomics Bioinformatics 13:17-24 (2015).

Zhang et al., "Focus on Extracellular Vesicles: Therapeutic Potential of Stem Cell-Derived Extracellular Vesicles." Int. J. Mol. Sci. 17(174):1-11 (2016).

Zhao et al., "A Simple Way to Enhance Doxil® Therapy: Drug Release from Liposomes at the Tumor Site by Amphiphilic Block Copolymer." J Control Release 168(1):61-69 (2013).

Zhao et al., "Fixation-induced cell blebbing on spread cells inversely correlates with phosphatidylinositol 4,5-bisphosphate level in the plasma membrane." FEBS Open Bio 4:190-199 (2014).

Zollinger et al., "Cytologic Studies with the Phase Microscope I. The Formation of "Blisters" on Cells in Suspension (Potocytosis), With Observations on the Nature of the Cellular Membrane." Am J Pathol. 24(3):545-567 (1948).

Gyorgy et al., "Membrane vesicles, current state-of-the-art: emerging role of extracellular vesicles." Cell. Mol. Life Sci. 68:2667-2688 (2011).

Hagmann et al., "Regulation of Plasma Membrane Blebbing by the Cytoskeleton." Journal of Cellular Biochemistry 73:488-499 (1999).

Harrigan et al., "Accumulation of doxorubicin and other lipophilic amines into large unilamellar vesicles in response to transmembrane pH gradients" Biochimica et Biophysica Acta 1149 :329-338 (1993).

(56) References Cited

OTHER PUBLICATIONS

Hedlund et al., "Thermal- and Oxidative Stress Causes Enhanced Release of NKG2D Ligand-Bearing immunosuppressive Exosomes in Leukemia/Lymphoma T and B Cells." PLoS ONE 6(2):e16899 (2011).

Hillaireau et al., "Nanocarriers' entry into the cell: relevance to drug delivery." Cell. Mol. Life Sci. 66:2873-2896 (2009).

Hinshaw et al., "Cytoskeletal and Morphologic Impact of Cellular Oxidant Injury." Am J Pathol 123(3):454-464 (1986).

Immordino et al., "Stealth liposomes: review of the basic science, rationale, and clinical applications, existing and potential." International Journal of Nanomedicine, 1(3) 297-315 (2006).

Ishida et al., "PEGylated liposomes elicit an anti-PEG IgM response in a T cell-independent manner." Journal of Controlled Release 122:349-355 (2007).

Iyer et al., "Exploiting the enhanced permeability and retention effect for tumor targeting." Drug Discovery Today 11(17/18):812-818 (2006).

Katsuda et al., "The therapeutic potential of mesenchymal stem cell-derived extracellular vesicles." Proteomics 13:1637-1653 (2013).

Keller et al., "Differences in Cortical Actin Structure and Dynamics Document That Different Types of Blebs Are Formed by Distinct Mechanisms." Experimental Cell Research 277:161-172 (2002).

Kesharwani et al., "A review of nanocarriers for the delivery of small interfering RNA." Biomaterials 33:7138-7150 (2012).

Kim et al., "Exosomes Derived from IL-10-Treated Dendritic Cells Can Suppress Inflammation and Collagen-Induced Arthritis." J Immunol 174(10):6440-6448 (2005).

King et al., "Hypoxic enhancement of exosome release by breast cancer cells." BMC Cancer 12:421 (2012).

Kramer-Albers et al., "Oligodendrocytes secrete exosomes containing major myelin and stress-protective proteins: Trophic support for axons?" Proteomics Clin Appl. 1:1446-1461 (2007).

Labeur et al., "Generation of Tumor Immunity by Bone Marrow-Derived Dendritic Cells Correlates with Dendritic Cell Maturation Stage." The Journal of Immunology, 162 (1) 168-175 (Jan. 1, 1999).

Lamichhane et al., "Emerging Roles for Extracellular Vesicles in Tissue Engineering and Regenerative Medicine." Tissue Engineering: Part B 21(1):45-54 (2015).

Landau et al., "The Effects of High Hydrostatic Pressure on Human Cells in Primary and Continuous Culture." Experimental Cell Research 23:538-548 (1961).

Lee et al., "Exosomes and microvesicles: extracellular vesicles for genetic information transfer and gene therapy." Human Molecular Genetics 21(1)R125-R134 (2012).

Lian et al., "Trends and Developments in Liposome Drug Delivery Systems." Journal of Pharmaceutical Sciences 90(6):667-680 (2001).

Liu et al., "Murine Mammary Carcinoma Exosomes Promote Tumor Growth by Suppression of NK Cell Function." The Journal of Immunology 176(3):1375-85 (2006).

Llopis et al., "Measurement of cytosolic, mitochondrial, and Golgi pH in single living cells with green fluorescent proteins." Proc. Natl. Acad. Sci. USA vol. 95:6803-6808 (1998).

LV et al., "Toxicity of cationic lipids and cationic polymers in gene delivery." Journal of Controlled Release 114:100-109 (2006).

Lyass et al., "Correlation of Toxicity with Pharmacokinetics of Pegylated Liposomal Doxorubicin (Doxil) in Metastatic Breast Carcinoma." Cancer 89(5):1037-1047 (2000).

Mace et al., "NK Cell Lytic Granules Are Highly Motile at the Immunological Synapse and Require F-Actin for Post-Degranulation Persistence." J Immunol 189(10):4870-4880 (2012).

Mackenzie et al., "Rapid Secretion of lnterleukin-1B by Microvesicle Shedding." Immunity 8:325-835 (2001).

Maki et al., "Factors Regulating the Cytotoxic Activity of the Human Natural Killer Cell Line, NK-92." Journal of Hematotherapy & Stem Cell Research 10:369-383 (2001).

Martinez et al., "Transfer of differentiation signal by membrane microvesicles harboring hedgehog morphogens." Blood 108(9):3012-3020 (2006).

Mathivanan et al., "Exosomes: Extracellular organelles important in intercellular communication." Journal of Proteomics 73:1907-1920 (2010).

Mayer et al., "Uptake of adriamycin into large unilamellar vesicles in response to a pH gradient." Biochimica et Biophysica Acta 857:123-126 (1986).

Medvedev et al., "Regulation of Fas and Fas-Ligand Expression in NK Cells by Cytokines and the Involvement of Fas-Ligand in NK/LAK Cell-Mediated Cytotioxicity." Cytokine 9(6):394-404 (1997).

Miller, J.S., "Therapeutic applications: natural killer cells in the clinic." Hematology Am Soc Hematol Educ Program. 247-53 (2013).

Mitran et al., "Multiscale Computation of Cytoskeletal Mechanics During Blebbing." Cellular and Biomolecular Mechanics and Mechanobiology pp. 345-371 (2010).

Miyoshi et al., "Calpain Activation in Plasma Membrane Bleb Formation During tert-Butyl Hydroperoxide-Induced Rat Hepatocyte Injury." Gastroenterology 110:1897-19 (1996).

Monleon et al., "Differential Secretion of Fas Ligand- or APO2 Ligand/TNF-Related Apoptosis-Inducing Ligand-Carrying Microvesicles During Activation-Induced Death of Human T Cells." The Journal of Immunology 67 (12):6736-44 (2001).

Muralidharan-Chari et al., "Microvesicles: mediators of extracellular communication during cancer progression." Journal of Cell Science 123:1603-1611 (2010).

Niu et al., "Preparation and Characterization of Doxorubicin Liposomes." Methods in Molecular Biology 624:211-219 (2010).

Norman et al., "Cell Blebbing and Membrane Area Homeostasis in Spreading and Retracting Cells." Biophysical Journal 99:1726-1733 (2010).

Obregon et al., "Exovesicles from Human Activated Dendritic Cells Fuse with Resting Dendritic Cells, Allowing Them to Present Alloantigens." The American Journal of Pathology 169(6):2127-2136 (2006).

Ohno et al., "Systemically Injected Exosomes Targeted to EGFR Deliver Antitumor MicroRNA to Breast Cancer Cells." Molecular Therapy 21(1):185-191 (2013).

Parolini et al., "Microenvironmental pH Is a Key Factor for Exosome Traffic in Tumor Cells" Journal of Biological Chemistry 284(49):34211-34222 (2009).

Pascucci et al., "Paclitaxel is incorporated by mesenchymal stromal cells and released in exosomes that inhibit in vitro tumor growth: A new approach for drug delivery " Journal of Controlled Release 192:262-270 (2014).

Peche et al., "Induction of Tolerance by Exosomes and Short-Term Immunosuppression in a Fully MHC-Mismatched Rat Cardiac Allograft Model." American Journal of Transplantation 6:1541-1550 (2006).

Petros et al., "Strategies in the design of nanoparticles for therapeutic applications." Nature Reviews Drug Discovery 9:615-627 (2010).

Pornpattananangkul et al., "Stimuli-Responsive Liposome Fusion Mediated by Gold Nanoparticles." ACS Nano. 4(4):1935-1942 (2010).

Portney et al., "Nano-oncology: drug delivery, imaging, and sensing." Anal Bioanal Chem 384:620-630 (2006).

Rafelski et al., "Crawling Toward a Unified Model of Cell Motility: Spatial and Temporal Regulation of Actin Dynamics." Annu. Rev. Biochem. 73:209-39 (2004).

Ratajczak et al., "Embryonic stem cell-derived microvesicles reprogram hematopoietic progenitors: evidence for horizontal transfer of mRNA and protein delivery." Leukemia 20:847-856 (2006).

Reagan et al., "Mesenchymal Stem Cell Tumor-Homing: Detection Methods in Disease Model Systems." Stem Cells. 29(6):920-927 (2011).

Ridley, A.J. "Life at the Leading Edge." Cell 145:1012-1022 (2011).

Ostrowski et al., "Rab27a and Rab27b control different steps of the exosome secretion pathway." Nature Cell Biology 12:19-30 (2010).

Pegtel et al., "Functional delivery of viral miRNAs via exosomes." PNAS 107(14): 6328-6333 (2010).

Piffoux et al., "Extracellular vesicles for personalized medicine: the input of physically triggered production, loading and theranostic properties." Adv Drug Deliv Rev 138:247-258 (2019).

(56) References Cited

OTHER PUBLICATIONS

Prabaharan et al., "Gold nanoparticles with a monolayer of doxorubicin-conjugated amphiphilic block copolymer for tumor-targeted drug delivery." Biomaterials 30:6065-6075 (2009).
Prokop et al., "Nanovehicular Intracellular Delivery Systems." J Pharm Sci. 97(9): 3518-3590 (2008).
Rabouille, C. "Pathways of Unconventional Protein Secretion." Trends in Cell Biology 27(3):230-240 (2017).
Raiborg et al., "Protein sorting into multivesicular endosomes." Current Opinion in Cell Biology 15:446-455 (2003).
Rani et al., "Mesenchymal Stem Cell-derived Extracellular Vesicles: Toward Cell-free Therapeutic Applications." Mol Ther. 23(5): 812-823 (2015).
Riazifar et al., "Stem Cell Extracellular Vesicles: Extended Messages of Regeneration." Annu. Rev. Pharmacol. Toxicol.57:125-54 (2017).
Robert et al., "High-Sensitivity Flow Cytometry Provides Access to Standardized Measurement of Small-Size Microparticles—Brief Report." Arterioscler Thromb Vase Biol 32(4):1054-8 (2012).
Roux et al., "Membrane curvature controls dynamin polymerization." PNAS 107(9):4141-4146 (2010).
Rupert et al., "Determination of Exosome Concentration in Solution Using Surface Plasmon Resonance Spectroscopy." Analytical Chemistry 86:5929-5936 (2014).
Saari et al., "Microvesicle- and exosome-mediated drug delivery enhances the cytotoxicity of Paclitaxel in autologous prostate cancer cells." Journal of Controlled Release 220:727-737 (2015).
Sadauskas et al., "Kupffer cells are central in the removal of nanoparticles from the organism." Particle and Fibre Toxicology 4(10):1-7 (2007).
Sahay et al., "Endocytosis of Nanomedicines." J Control Release 145(3):182-195 (2010).
Sahay et al., "Efficiency of siRNA delivery by lipid nanoparticles is limited by endocytic recycling." Nat Biotechnol 31(7):653-658 (2013).
Savina et al., "Rab11 Promotes Docking and Fusion of Multivesicular Bodies in a Calcium-Dependent Manner." Traffic 6:131-143 (2005).
Savla et al., "Tumor targeted quantum dot-mucin 1 aptamer-doxorubicin conjugate for imaging and treatment of Cancer." Journal of Controlled Release 153:16-22 (2011).
Semple et al., "Interactions of liposomes and lipid-based carrier systems with blood proteins: Relation to clearance behaviour in vivo." Advanced Drug Delivery Reviews 32:3-17 (1998).
Shelke et al., "Importance of exosome depletion protocols to eliminate functional and RNA-containing extracellular Vesicles from fetal bovine serum." Journal of Extracellular Vesicles 3:24783 (2014).
Shimoda et al., "Exosomes as nanocarriers for systemic delivery of the Helicobacter pylori virulence factor CagA." Scientific Reports 6:18346 (2016).
Shtam et al., "Exosomes are natural carriers of exogenous siRNA to human cells in vitro." Cell Communication and Signaling 11:88 (2013).
Simons et al., "Functional rafts in cell membranes." Nature 387:569-572 (1997).
Smith et al., "Measurement of Protein Using Bicinchoninic Acid." Analytical Biochemistry 150:76-85 (1985).
Soo et al., "Nanoparticle tracking analysis monitors microvesicle and exosome secretion from immune cells." Immunology 136:192-197 (2012).
Staykova et al., "Mechanics of surface area regulation in cells examined with confined lipid membranes." PNAS 108(22):9084-9088 (2011).
Suk et al., "PEGylation as a strategy for improving nanoparticle-based drug and gene delivery." Adv Drug Deliv Rev. 99(Pt A):28-51 (2016).
Takahashi et al., "Exosomes maintain cellular homeostasis by excreting harmful DNA from cells." Nature Communications 8(1):1-16 (2017).
Tang et al., "Mesenchymal Stem Cell Derived ExosomesThe Potential for Translational Nanomedicine." Academic Press, 2015.
Tauro et al., "Comparison of ultracentrifugation, density gradient separation, and immunoaffinity capture methods for isolating human colon cancer cell line LIM1863-derived exosomes." Methods 56:293-304 (2012).
Thanh et al., "Functionalisation of nanoparticles for biomedical applications." Nano Today 5:213-230 (2010).
Thone et al., "Extracellular blebs: Artificially-induced extracellular vesicles for facile production and clinical translation." Methods 177:135-145 (2020).
Tian et al., "Surface functionalized exosomes as targeted drug delivery vehicles for cerebral ischemia therapy." Biomaterials 150:137-149 (2018).
Toledano et al., "Reconstructed Stem Cell Nanoghosts: A Natural Tumor Targeting Platform." Nano Lett. 13:3248-3255 (2013).
Tominaga et al., "A novel platform for cancer therapy using extracellular vesicles." Advanced Drug Delivery Reviews 95:50-55 (2015).
Tricarico et al., "Biology and biogenesis of shed microvesicles." Small GTPASES 8(4):220-232 (2017).
Turiak et al., "Proteomic characterization of thymocyte-derived microvesicles and apoptotic bodies in BALB/c mice." Journal of Proteomics 74:2025-2033 (2011).
Van Der Pol et al., "Optical and non-optical methods for detection and characterization of microparticles and exosomes." Journal of Thrombosis and Haemostasis 8:2596-2607 (2010).
Van Deun et al., "The impact of disparate isolation methods for extracellular vesicles on downstream RNA profiling." Journal of Extracellular Vesicles 3:24858 (2014).
Verhoef et al., "Questioning the Use of PEGylation for Drug Delivery." Drug Deliv Transl Res. 3(6):499-503 (2013).
Viaud et al., "Dendritic Cell-Derived Exosomes for Cancer Immunotherapy: What's Next?" Cancer Research 70(4):1281-5 (2010).
Villarroya-Beltri et al., "ISGylation controls exosome secretion by promoting lysosomal degradation of MVB proteins."
Vion et al., "Shear Stress Regulates Endothelial Microparticle Release." Circulation Research 112(10):1323-1333 (2013).
Voldman, J. "Electrical Forces For Microscale Cell Manipulation." Annu. Rev. Biomed. Eng. 8:425-54 (2006).
Wang et al., "Ciliated micropillars for the microfluidic-based isolation of nanoscale lipid vesicles." Lab Chip 13(15):2879-2882 (2013).
Wiklander et al., "Extracellular vesicle in vivo biodistribution is determined by cell source, route of administration and targeting." Journal of Extracellular Vesicles 4:26316 (2015).
Wilhelm et al., "Analysis of nanoparticle delivery to tumours." Nature Reviews Materials 1:6014 (2016).
Witwer et al., "Standardization of sample collection, isolation and analysis methods in extracellular vesicle research." Journal of Extracellular Vesicles 2:20360 (2013).
Wong et al., "Synthetically Functionalized Retroviruses Produced from the Bioorthogonally Engineered Cell Surface." Bioconjugate Chemistry 22(2):151-155 (2011).
Wubbolts et al., "Proteomic and Biochemical Analyses of Human B Cell-derived Exosomes." The Journal of Biological Chemistry 278(13):10963-10972 (2003).
Herberts et al., "Risk factors in the development of stem cell therapy." Journal of Translational Medicine 9(29):1-14 (2011).
Hogue, MJ. "The Effect of Hypotonic and Hypertonic Solutions on Fibroblasts of the Embryonic Chick Heart in vitro." Journal of Experimental Medicine 30(6):617-648 (1919).
Hood et al., "Maximizing Exosome Colloidal Stability Following Electroporation." Analytical Biochemistry 448:41-49 (2014).
Hoshino et al., "Tumour exosome integrins determine organotropic metastasis." Nature 527(7578): 329-335 (2015).
Hsu et al., "Regulation of exosome secretion by Rab35 and its GTPase-activating proteins TBC1D10A-C." Journal of Cell Biology 189(2):223-232 (2010).
Hung et al. "Stabilization of Exosome-targeting Peptides via Engineered Glycosylation." The Journal of Biology Chemistry 290(13):8166-8172 (2015).

(56) References Cited

OTHER PUBLICATIONS

Hung et al., "A platform for actively loading cargo RNA to elucidate limiting steps in EV-mediated delivery." Journal of Extracellular Vesciles 5:31027 (2016).

Ibrahim et al.,"Exosomes as Critical Agents of Cardiac Regeneration Triggered by Cell Therapy." Stem Cell Reports 2:606-619 (2014).

Im et al., "Label-free detection and molecular profiling of exosomes with a nano-plasmonic sensor." Nat Biotechnol. 32(5):490-495 (2014).

Ingato et al., "Good things come in small packages: Overcoming challenges to harness extracellular vesicles for therapeutic delivery." Journal Controlled Release 241:174-185 (2016).

Ingato et al., "Cancer Cell-Derived, Drug-Loaded Nanovesicles Induced by Sulfhydryl-Blocking for Effective and Safe Cancer Therapy." ACS Nano 12:9568-9577 (2018).

Ishida et al. "Accelerated blood clearance of PEGylated liposomes upon repeated injections: Effect of doxorubicin-encapsulation and high-dose first injection." Journal of Controlled Release 115:251-258 (2006).

Israelachivilli et al., "Theory of Self-Assembly of Hydrocarbon Amphiphiles into Micelles and Bilayers." J. Chem. Soc., Faraday Trans. 2 72:525-1568 (1976).

Jang et al., "Bioinspired Exosome-Mimetic Nanovesicles for Targeted Delivery of Chemotherapeutics to Malignant Tumors." ACS Nano 7(9):7698-7710 (2013).

Jeyaram et al., "Preservation and Storage Stability of Extracellular Vesicles for Therapeutic Applications." AAPS J 20(1):1-13 (2017).

Jimenez et al., "Endothelial cells release phenotypically and quantitatively distinct microparticles in activation and apoptosis." Thrombosis Research 109:175-180 (2003).

Jo et al., "Microfluidic fabrication of cell-derived nanovesicles as endogenous RNA carriers." Lab Chip 14(7):1261-9 (2014).

Johnstone et al., "Vesicle Formation during Reticulocyte Maturation." The Journal of Biological Chemistry 262(19):9412-9420 (1987).

Kadiu et al., "Biochemical and Biologic Characterization of Exosomes and Microvesicles as Facilitators of HIV-1 Infection in Macrophages." The Journal of Immunology 189(2):744-54 (2012).

Kanwar et al., "Microfluidic device (ExoChip) for On-Chip isolation, quantification and characterization of circulating exosomes." Lab Chip 14(11):1891-900 (2014).

Kastelowitz et al., "Exosomes and Microvesicles: Identification and Targeting By Particle Size and Lipid Chemical Probes." Chembiochem 15(7):923-928 (2014).

Katakowski et al., "Exosomes from marrow stromal cells expressing miR-146b inhibit glioma growth." Cancer Lett. 335(1):201-204 (2013).

Kessler et al., "Interference by Lipids in the Determination of Protein Using Bicinchoninic Acid." Analytical Biochemistry 159:138-142 (1986).

Kim et al., "Large-scale generation of cell-derived nanovesicles." 6(20):12056-64 (2014).

King et al., "Bioreactor Development for Stem Cell Expansion and Controlled Differentiation." Curr Opin Chem Biol. 11(4):394-398 (2007).

Kooijmans et al., "Display of GPI-anchored anti-EGFR nanobodies on extracellular vesicles promotes tumour cell targeting." Journal of Extracellular Vesicles 5:31053 (2016).

Kosaka et al., "Secretory Mechanisms and Intercellular Transfer of MicroRNAs in Living Cells" The Journal of Biological Chemistry 285(23):17442-17452 (2010).

Lai et al., "Exosome secreted by MSC reduces myocardial ischemia/reperfusion injury." Stem Cell Research 4:214-222 (2010).

Lai et al., "Dynamic Biodistribution of Extracellular Vesicles In Vivo Using a Multimodal Imaging Reporter." Stem Cell Research 4:214-222 (2010).

Lammmers et al., "Drug targeting to tumors: Principles, pitfalls and (pre-) clinical progress." Journal of Controlled Release 161:175-187 (2012).

Lamparski et al., "Production and characterization of clinical grade exosomes derived from dendritic cells." Journal of Immunological Methods 270:211-226 (2002).

Lauf et al., "A Chloride Dependent K+ Flux Induced by N-ethylmaleimide in Genetically Low K+ Sheep and Goat Erythrocytes." Biochemical and Biophysical Research Communications 92(4):1422-1428 (1980).

Lee et al., "Acoustic Purification of Extracellular Microvesicles." ACS Nano 9(3):2321-2327 (2015).

Lener et al., "Applying extracellular vesicles based therapeutics in clinical trials—an ISEV position paper." Journal of Extracellular Vesicles 4:30087 (2015).

Li et al., "Exosomes Derived from Hypoxic Oral Squamous Cell Carcinoma Cells Deliver miR-21 to Normoxic Cells to Elicit a Prometastatic Phenotype." Cancer Res 76(7):1770-1780 (2016).

Liu et al., "Targeted exosome-mediated delivery of opioid receptor Mu siRNA for the treatment of morphine relapse." Scientific Reports 5:17543 (2015).

Llorente et al., "Molecular lipidomics of exosomes released by PC-3 prostate cancer cells." Biochimica et Biophysica Acta 1831:1302-1309 (2013).

Mahaweni et al., "Tumour-derived exosomes as antigen delivery carriers in dendritic cell-based immunotherapy for malignant mesothelioma." Journal of Extracellular Vesicles 2:22492 (2013).

Mause et al., "Protagonists of a Novel Communication Network for Intercellular Information Exchange." Microparticles 107(9):1047-57 (2010).

Mills et al., "Apoptotic Membrane Blebbing Is Regulated by Myosin Light Chain Phosphorylation." The Journal of Cell Biology 140(3):627-636 (1998).

Momen-Heravi et al., "Current methods for the isolation of extracellular vesicles." Biol Chem 394(10):1253-1262 (2013).

Momen-Heravi et al., "Exosome-mediated delivery of functionally active miRNA-155 inhibitor to macrophages." Nanomedicine 10(7):1517-1527 (2014).

Momparler et al., "Effect of Adriamycin on DNA, RNA and Protein Synthesis in Cell-free Systems and Intact Cells." Cancer Research 36:2891-2895 (1976).

Montecalvo et al., "Mechanism of transfer of functional microRNAs between mouse dendritic cells via exosomes." Blood 119(3):756-766.

Munagala et al., "Bovine milk-derived exosomes for drug delivery." Cancer Lett. 371(1):48-61 (2016).

Nakamishi et al., "Bioactive Nanocarbon Assemblies: Nanoarchitectonics and Applications." Nanotechnology 9(3):378-394 (2014).

Nasongkla et al., "cRGD-Functionalized Polymer Micelles for Targeted Doxorubicin Delivery." Angew. Chem. Int. Ed. 43:6323-6327 (2004).

Nikam et al., "NANOPARTICLES—An Overview." International Journal of Research and Development in Pharmacy and Life Sciences 3(5):1121-1127 (2014).

O'Brien et al., "miR-134 in extracellular vesicles reduces triple-negative breast cancer aggression and increases drug sensitivity." Oncotarget, 6(32):32774-32788 (2015).

Ohara et al., "Effective delivery of chemotherapeutic nanoparticles by depleting host Kupffer cells." Int. J. Cancer:131:2402-2410 (2012).

\* cited by examiner

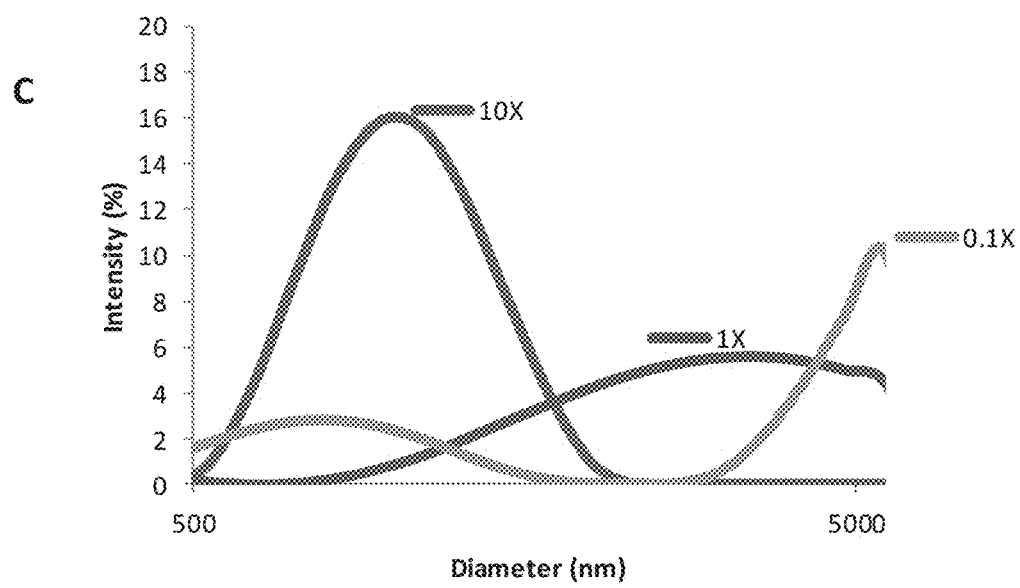
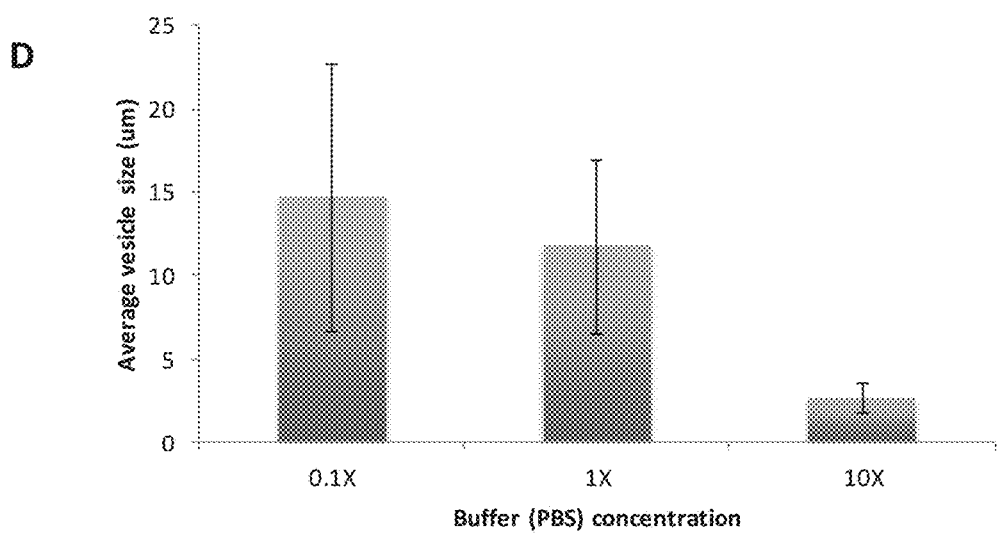
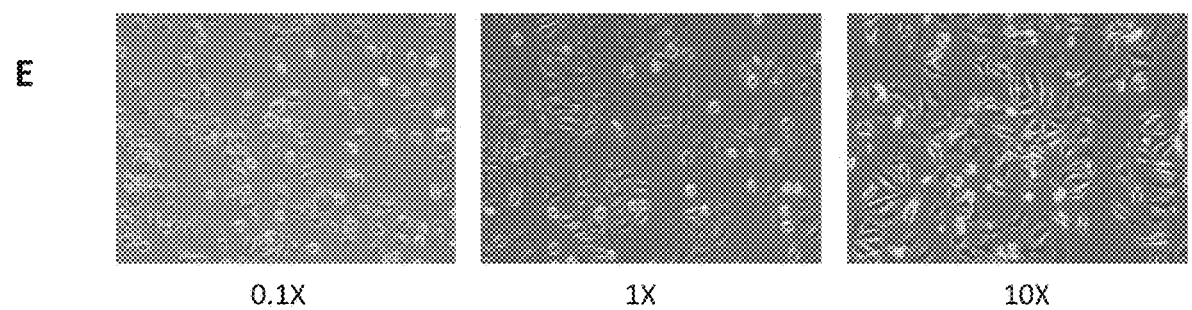
Figure 12 con't.

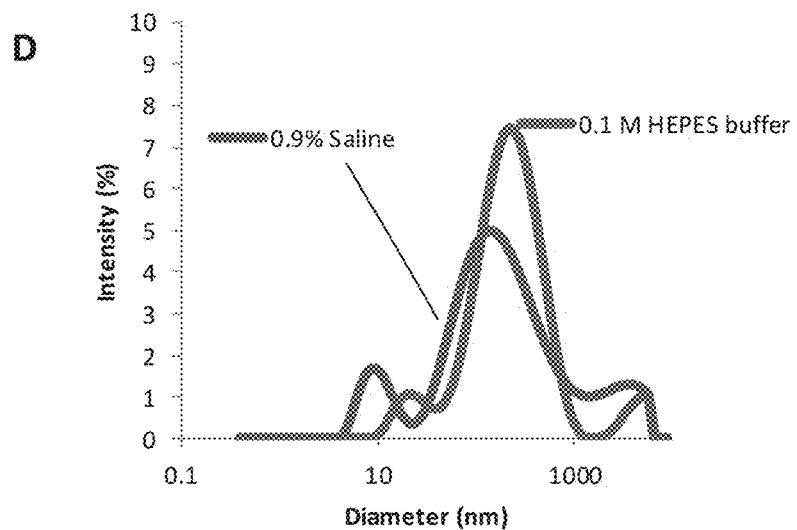
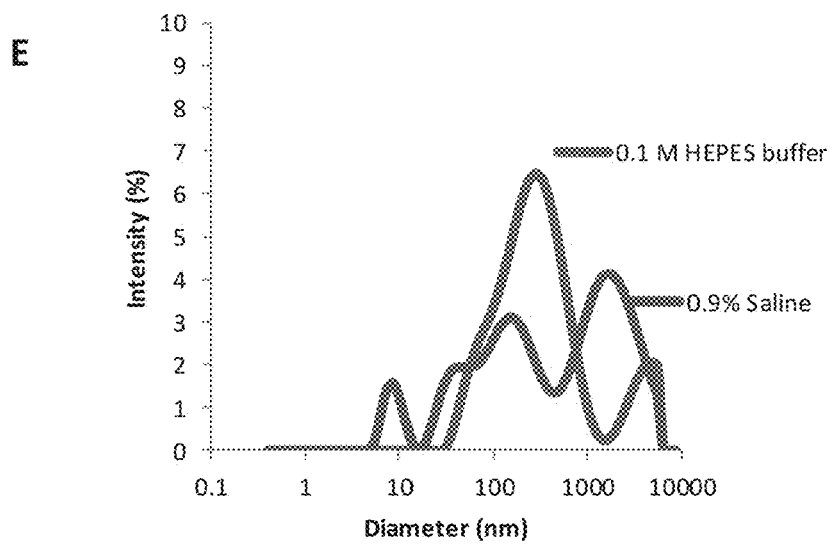
Figure 13 con't.

EXTRACELLULAR VESICLES AND METHODS AND USES THEREOF

CROSS REFERENCE TO RELATED APPLICATIONS

This application is a national stage of PCT Patent Application No. PCT/US2017/064062, entitled "Extracellular Vesicles and Methods and Uses Thereof" to Kwon et al., filed Nov. 30, 2017, which claims priority to U.S. Provisional Application Ser. No. 62/428,407, entitled "Nanovesicles for Compound Delivery" to Kwon et al., filed Nov. 30, 2016, the disclosures of which are incorporated by reference herein in their entirety.

STATEMENT REGARDING FEDERALLY SPONSORED RESEARCH OR DEVELOPMENT

This invention was made with Governmental support under Grant No. DGE-1321846 awarded by the National Science Foundation. The government has certain rights in the invention.

FIELD OF THE INVENTION

The present invention is directed to extracellular vesicles, including methods of synthesis and applications thereof, more particularly, extracellular vesicles created from living cells, which are created with more homogeneity in size and increased production levels. The present invention is also directed to medicaments delivered via an extracellular vesicle as well as method to deliver an extracellular vesicle to a patient.

BACKGROUND OF THE INVENTION

The fields of drug delivery and gene therapy rely on nano-sized carriers for effective delivery of precious cargo to the designated target site. (See, e.g., Thomas, C. E., et al., Nat. Rev. Genet. 4, 346-58 (2003); Lv, H., Zhang, et al., J. Control. Release 114, 100-9 (2006); and Silva, A. K. A. et al. Nanoscale 5, 11374-84 (2013), the disclosures of which are incorporated herein by reference.) Therapeutic delivery agents have two key objectives: protect cargo from the harsh environment of the body and release cargo at the appropriate site without inducing immunogenic response. In order to achieve these goals, a variety of viral and non-viral nano-carriers with highly specific properties, dependent upon the type of cargo and desired site of delivery, have been designed. Common viral nanocarriers include retroviruses and adenoviruses. Common nonviral nanocarriers include liposomes, polyplexes, and dendrimers. In addition, compounds can be delivered to cells by passive membrane transport or forceful entry that disrupts the membrane (e.g. particle bombardment, sonication). Nevertheless, issues with non-specific cytotoxicity, poor biocompatibility, and low efficacy of compound delivery still remain major challenges in the field.

Cells emit extracellular vesicles (EVs) to transport vital biomacromolecules such as mRNA and microRNA between cells and exogenous RNA-loaded exosomes have been used to achieve targeted, tissue-specific delivery. One common type of EV is an exosome, which have been studies as a possible method for therapeutic delivery. Cells in culture naturally produce EVs but at a rate significantly below the requirements for therapeutic administration, which has been attempted to be mitigated by exposing cells to endosomal trafficking regulators, modified proteins, and external stressors. However, these time- and labor-intensive processes directly affect cellular activities and make it difficult to preserve the composition and biological functions of EVs at a desired cellular stage. Thus, it is essential to explore alternative methods for rapid and large-scale production of EVs.

SUMMARY OF THE INVENTION

In one embodiment of this disclosure is directed to a method to generate extracellular vesicles. In various embodiments, these vesicles are created by exposing at least one mammalian cell to a solution comprising sulfhydryl blocking reagents.

In many such embodiments the methods may consist of collecting extracellular vesicles that are generated by exposing the at least one mammalian cell to the solution comprising sulfhydryl blocking reagents.

In some embodiments, the solution may also consist of a buffer. In some such embodiments, the buffer concentration used in this solution may be altered to modify the size and distribution of extracellular vesicles produced by the method of this embodiment.

In more embodiments, numerous sulfhydryl blocking reagents may be used. In some such embodiments, the method may use sulfhydryl blocking reagents comprising a cross-linking reagent and a reducing agent. In some such embodiments, the cross-linking agent may be selected from formaldehyde or paraformaldehyde, while the reducing agent may be selected from dithiothreitol, cysteine, and glutathione.

In yet other embodiments, paraformaldehyde may be used as the cross-linking reagent, dithiothreitol as the reducing agent, and phosphate buffered saline as the buffer.

In still yet other embodiments, the specific concentration of paraformaldehyde may range from about 2.5 mM to about 2.5 M, while the specific concentration of dithiothreitol may range from about 0.2 mM to about 200 mM. In some such embodiments, the specific concentration of paraformaldehyde may be 25 mM, while the specific concentration of dithiothreitol may be 2 mM. In still other such embodiments, the phosphate buffered saline may have a concentration of at least 5×, the phosphate buffered saline may have a concentration of less than 0.5×, or the phosphate buffered saline may have a concentration of less than 0.5×.

In still yet other embodiments, the extracellular vesicles produced by the method of this embodiment may range in size from 25-100 nm, 100-700 nm, 700-2000 nm, or 1000-10000 nm. In these size ranges, the extracellular vesicles may have a polydispersity index of less than about 0.6, such as less than about any of 0.5, 0.4, 0.3, 0.2, or 0.1.

Another embodiment of this disclosure is drawn to methods to provide extracellular vesicles to a treatment subject.

In many such embodiments, the method may include the steps of obtaining at least one extracellular vesicle generated from at least one mammal cell.

In other embodiments, the method includes purifying the at least one extracellular vesicle in a saline buffer.

In still other embodiments, the method may include the step of loading the at least one extracellular vesicle with a medicament. In some such embodiments, the loading step may be performed by incubating the at least one extracellular vesicle with a medicament at 37° C. for at least one hour.

In yet other embodiments, the loaded extracellular vesicles may have a concentration of at least 100 μg/mL and may be selected from the doxorubicin and a vaccine.

In still yet other embodiments, the at least one mammal cell may come from the treatment subject and may be an antigen-presenting cell. In some such embodiments, these cells may be selected from a dendritic cell and a tumor cell.

In still yet other embodiments, the administration of the at least one extracellular vesicle may be performed in proximity to the tumor tissue.

In still yet other embodiments, the administering step may effect a response in the treatment subject, wherein the response may consist of T-cell activation or immune response stimulation.

Still another embodiment of this disclosure is directed to a composition for the delivery of a compound.

In many such embodiments, the compound may comprise at least one extracellular vesicle derived from a mammalian cell and is substantially free of a nuclear component.

In other embodiments, the extracellular vesicle has a diameter of between about 10 nm and 10000 nm.

In still other embodiments, the mammalian cell may come from a stem cell, a cancer cell, a dendritic cell presenting an antigen, and a red blood cell.

In yet other embodiments, the mammalian cell may come from a primary cell or a cell derived from a cell line.

In still yet other embodiments, at least one extracellular vesicle may be a plurality of extracellular vesicles having an average diameter of between about 10 nm and about 200 nm.

In still yet other embodiments, the at least one extracellular vesicle may also be generated through sulfhydryl blocking, may be stable for at least six hours in serum at 37° C., and may be loaded with a medicament.

In still yet other embodiments, this medicament may be selected from a therapeutic agent, an imaging agent, an anticancer agent, doxorubicin, an antigenic peptide, and a polynucleotide encoding an antigenic peptide.

In still other embodiments, the compound of this embodiment may comprise a saline buffer.

Additional embodiments and features are set forth in part in the description that follows, and in part will become apparent to those skilled in the art upon examination of the specification or may be learned by the practice of the disclosure. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying drawings where.

DETAILED DISCLOSURE OF THE INVENTION

Figure 1:
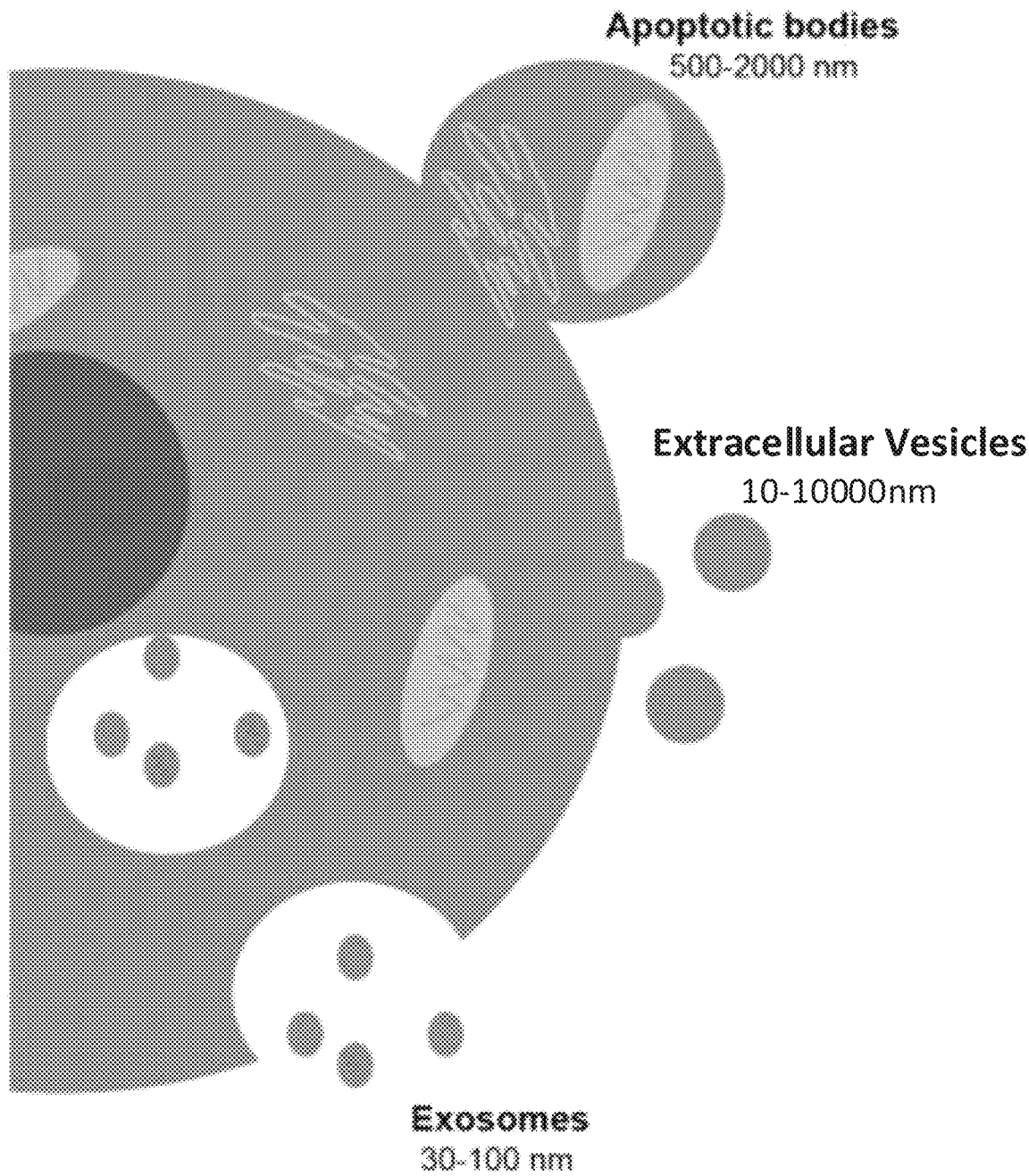
FIG. 1 illustrates various extracellular bodies that may be emitted from a cell along with general size ranges that these bodies may possess.

Turning now to the diagrams and figures, embodiments of the invention are generally directed to EVs, methods of their manufacture, and applications thereof (FIG. 1). Several embodiments are directed to the EVs themselves, which are chemically modified vesicles that resemble naturally occurring EVs and exosomes. In many of these embodiments, the EVs have altered actin-myosin function that lead to an altered structure within the vesicles.

Various embodiments are also directed to EVs that are compound loaded. In numerous embodiments, the EVs are treated to retain a compound for a particular treatment. Accordingly, the compounds loaded onto the vesicles are chosen for the proper application. In several embodiments, antineoplastic compounds are loaded onto EVs for treatment of neoplasms, tumors, or cancer. In more particular embodiments, the antineoplastic compound is doxorubicin. In many other embodiments, EVs present an antigenic compound to induce a particular immune response, such as, for example, elicit T-cell activation. In more particular embodiments, the EVs present the cancer antigen SIINFEKL.

Methods of EV manufacture in accordance with many embodiments are also described. In many of these embodiments, EVs can be manufactured from any animal cell, dependent on the application. For example, to treat a patient, the patient's own cells can be extracted and used to manufacture the EVs having several benefits, which may include a lack of an allogenic response. Accordingly, multiple embodiments are directed to personalized EVs derived from an animal host source. The cell-type for EV manufacture may also vary, dependent on application. In some embodiments, the cell-type chosen are blood cells, fibroblasts, or tumor cells. In various embodiments, the cell type is chosen for ease of extraction and culture. In other embodiments, the cell type is chosen based on characteristics of the cell. For example, dendritic cells may be chosen for their antigen presenting capability, which can yield EVs presenting an antigen. Accordingly, many embodiments are directed to EVs derived from antigen-presenting cells.

In numerous embodiments, EVs are produced by incubating cells with sulfhydryl blocking reagents. These reagents alter the function of a natural cellular phenomenon known as blebbing. The alteration of blebbing by sulfhydryl blocking reagents results in vesicles of altered structure. In many embodiments, the sulfhydryl blocking reagents may be comprised of a non-specific cross-linker and a reducing agents. In some embodiments, the non-specific cross-linker is selected from N-ethyl maleamide, formaldehyde, and paraformaldehyde. In some embodiments, the reducing agent is selected from dithiothreitol, cysteine, and glutathione. In several embodiments, the non-specific cross-linker may be paraformaldehyde, and the reducing agent may be dithiothreitol. In more particular embodiments, the concentrations of the reagents are 25 mM paraformaldehyde with 2 mM dithiothreitol. It should be noted that paraformaldehyde and its monomeric subunit, formaldehyde, are non-specific cross-linking reagents, while dithiothreitol is a reducing agent. Additionally, certain embodiments are directed to scalable manufacture of EVs. Accordingly, embodiments of the processes described within yield large amounts personalized EVs.

In some embodiments, EVs may be produced in the presence of a buffer along with sulfhydryl blocking reagents. In some embodiments, the buffer concentration is any of 0.1×, 0.2×, 0.3×, 0.4×, 0.5×, 0.6×, 0.7×, 0.8×, 0.9×, 1×, 2×, 3×, 4×, 5×, 6×, 7×, 9×, and 10×. In some embodiments, a buffer may be selected from the group consisting of PBS, saline, DMEM, GPMV, HEPES, DPBS, or any other buffer known in the art. In particular embodiments, the buffer is 1×BS, while in some embodiments the buffer is 0.1×, and in some embodiments the buffer is 10×.

Various embodiments are also directed to methods of treatment. In many embodiments, the method of treatment is utilizing compound-loaded EVs on an animal subject, such as, for example, a human patient. In various other embodiments, the method of treatment is utilizing antigen-presenting EVs on an animal subject. The disorder to be treated depends on the application. Accordingly, in several embodiments, the EVs can be used treat any disorder that utilizes a compound for treatment. In more particular embodiments, EVs loaded with antineoplastic compounds are used to treat neoplasms, tumors, or cancer. In other particular embodiments, antigen-presenting EVs are utilized to elicit an immune response to treat a disorder. In more particular embodiments, the disorder to be treated by the antigen-presenting EVs is cancer or a pathogenic infection.

In some embodiments, EVs may be generated to carry a therapeutic agent. In some embodiments, the therapeutic agent may be Doxorubicin (DOX). In order to generate EVs carrying DOX, EVs may be produced by inducing vesiculation in harvested cells via sulfhydryl blocking in the presence of a buffer, specifically, vesiculation induced by paraformaldehyde and dithiothreitol in the presence of PBS. The EVs generated by this means may be isolated by centrifugation and incubated in the presence of DOX to load DOX into the EVs. Once loaded with DOX, the EVs may be filtered again to remove excess DOX from the solution. At this point, the DOX-loaded EVs (DOX-EVs) may be administered to an individual.

In some embodiments, EVs may be generated to display certain surface moieties. In some embodiments, the surface moiety may be the SIINFEKL antigen. In order to generate SIINFEKL-loaded EVs (SIINFEKL-EVs), cells may be harvested from an individual. Harvested cells may be pulsed in the presence of the SIINFEKL antigen to cause the harvested cells to display SIINFEKL. Upon loading SIINFEKL onto the harvested cells, vesiculation may be induced via sulfhydryl blocking in the presence of a buffer, specifically, vesiculation induced by paraformaldehyde and dithiothreitol in the presence of PBS. The EVs generated by this vesiculation may be collected via centrifugation to remove any cells or excess chemicals. The resultant SIINFEKL-EVs may be administered to an individual to induce a response in the individual to the presence of SIINFEKL.

Figure 2:
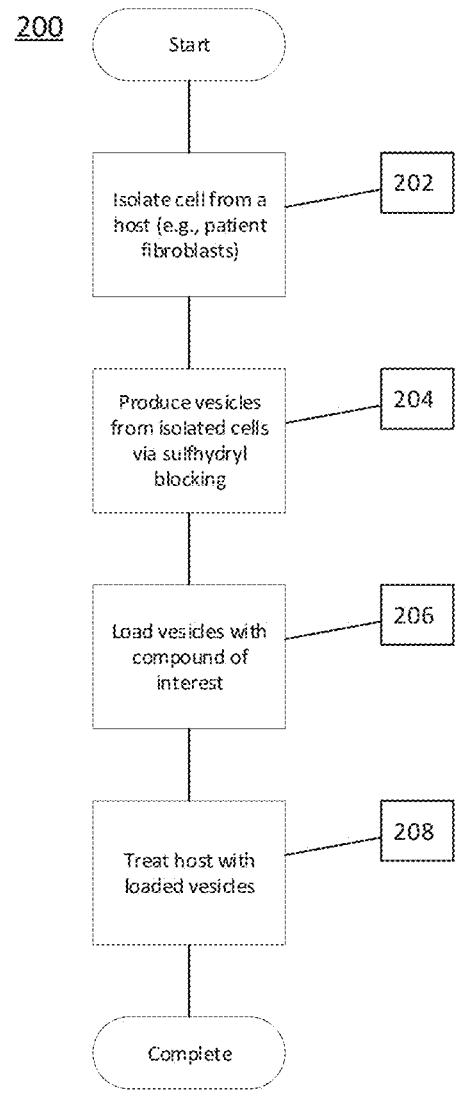
FIG. 2 illustrates a process for treating a host with extracellular vesicles produced from isolated cells of the host in accordance with an embodiment of the invention.

Turning now to FIG. 2, an embodiment of a process for personalized treatment with EVs is presented. It should be noted that FIG. 2 is only exemplary, and embodiments of the invention are not limited to personalized treatment. In a personal treatment regime as described in Process 200, the host to be treated is the same host that provided the animal cells to manufacture the EV. For example, a patient having a cancer can get personalized treatment by isolated cells from the patient (202), production of EVs from the patient's isolated cells (204), loading neoplastic compounds onto the derived EVs (206), and treating the patient with the personalized, compound-loaded EVs (208). Although humans are suggested, it should be understood, however, that veterinary or experimental treatments on respective nonhuman animals could also be performed.

Process 200 can begin with extracting and isolating animal cells from a host source (202). In several embodiments, the host is any animal to be treated, such as, for example a human patient. The cell type to be extracted is dependent on the application. In many embodiments, the cell type is one that are of easy access and culture, such as blood cells or fibroblasts. In a non-personalized context, cells may be harvested from another source that is not directly from a patient or host. Harvesting cells from other sources may include cells harvested from cell lines established in cell culture or harvesting cells from another host source, such as another animal or human.

Process 200 can continue with production of EVs from the isolated animal cells (204). Application of sulfhydryl blocking reagents on the isolated the isolated animal cells can yield mass quantity of EVs that is scalable. In particular embodiments, the sulfhydryl blocking reagents are 25 mM paraformaldehyde with 2 mM dithiothreitol. It should be understood, however, the sulfhydryl blocking reagents and their concentration to be used can vary, dependent on the application and optimization. Once the EVs have been produced, the vesicles can be concentrated and purified by acceptable protocols, which may include centrifugation, filtration, chromatography, or other applicable methods.

Isolated EVs can be loaded with a compound of interest (206). The compound to be loaded is determined by the application. For example, if the personalized treatment is directed at cancer, the compound could be an antineoplastic drug. Accordingly, the EVs are incubated with the compound of interest in order to load the vesicles with the drug. The procedure for compound loading will vary, dependent on the properties of the EVs and the compounds. For example, loading EVs with antineoplastic drug doxorubicin is dependent on compound concentration, temperature, and incubation time.

Once the EVs are loaded with the compound of interest, the compound-loaded vesicles can be used for treatment of the host (208). The site of treatment will depend on the application. For example, with EVs can be administered locally at the tumor site or systematically by any appropriate mechanism (e.g., oral, intravenous).

It should be noted that the steps present in Process 200 do not necessarily have to be completed in the order as described in FIG. 2. Such that in some embodiments, loading vesicles with a compound of interest step may occur prior to producing vesicles by sulfhydryl blocking. Such an instance may occur in situations where the vesicles are being loaded with a compound (e.g., mRNA, protein, or peptide) is produced by the cell, from which the vesicles will be produced.

EVs have the potential to be an exciting option for nanoscale delivery. EVs present a unique chance to harness near natural biological carriers for treatments of a host. As diagrammed in FIG. 3, extracellular vesicles offer a compelling opportunity to develop into personalized therapeutic delivery carriers. In one embodiment, cells are harvested from a patient and used to produce vesicles in vitro. In more embodiments, these vesicles are loaded with compounds for delivery to the patient's diseased tissue. In some embodiments, the EVs contain surface modification to improve targeting. Personalized treatment, as depicted by example in FIG. 3, would mitigate an immunogenic response associated with non-self compound carriers. Furthermore, EVs could also improve targeting, as determined by surface modifications on the vesicles and interaction of the modifications with the targeted host cells.

Despite their high potential in therapeutic delivery, vesicle-based therapeutics have been slow to progress to clinical trials due to problems associated with mass production. The low yield associated with ex vivo production of vesicles is a major challenge that leads to a bottleneck in the production process. In addition, traditional use of sulfhydryl blocking reagents, such as formaldehyde and N-ethyl maleamide, to produce EVs typically renders giant plasma membrane vesicles (e.g., as shown in membrane raft studies; E. Sezgin et al. Nat. Protoc. 7, 1042-51 (2012), the disclosure of which is incorporated herein by reference). Due to their large size and polydispersivity, giant plasma membrane vesicles are not suitable therapeutic delivery carriers.

Compositions for Delivery of a Compound

In some embodiments, EVs may be used to deliver a compound derived from a mammalian cell. EVs may also be free of a nuclear component. A nuclear component may be characterized by proteins and nucleic acid which are understood to be localized within the nucleus of a cell. A nuclear component does not include cellular components, which are naturally or artificially designed to be exported from the nucleus. As such, a nuclear component may not consist of carbohydrates, proteins, nucleic acids, which may be exported. Such nucleic acids may consist of plasm id DNA, plastid DNA, mitochondrial DNA, nuclear DNA, RNA, or RNA-DNA hybrid molecules, which naturally or artificially are exported from the nucleus.

EVs of some embodiments may come from nucleated or non-nucleated cells, which may come from the group consisting of stem cells, dendritic cells, red blood cells, or cancer cells. In certain embodiments, the EV may come from a dendritic cell. In some embodiments, the EV may come from a dendritic cell displaying an antigen. In some embodiments, EVs may come from a primary cell harvested from an individual, or an EV may come from a cell line established in cell culture.

In embodiments of a composition for the delivery of a compound, where the EV comes from nucleated or non-nucleated cells, including any of stem cells, dendritic cells, red blood cells, or cancer cells, where the cells display or do not display an antigen, these embodiments may comprise a plurality of EVs, where the average diameter of EVs is between about 10 nm and about 200 nm. In some of these embodiments, at least 10%, 20%, 30%, 40%, 50%, 60%, 70%, 80%, 90% or 100% of the EVs may be between about 10 nm and about 200 nm.

In any of the above embodiments for a composition for delivery of a compound, the composition may include a sulfhydryl blocking reagent. Additionally, in any of the embodiments for a composition for delivery of a compound, the EVs may comprise cross-linked actin, cross-linked myosin, or both cross-linked actin and cross-linked myosin. In embodiments containing cross-linked actin, cross-linked myosin, or both cross-linked actin and cross-linked myosin, an average of at least 0%, 10%, 20%, 30%, 40%, 50%, 60%, 70%, 80%, 90%, or 100% of the actin, myosin, or actin and myosin are cross-linked.

In any of the above embodiments for a composition for delivery of a compound, the EVs may be stable for at least 2, 4, 6, 8, 10, 12, 16, 24, or 48 hours in serum at 37° C.

Additionally, in any of the above embodiments for a composition for delivery of a compound, the EVs may be loaded with compound. In some of these embodiments, the compound is therapeutic or an imaging agent. In embodiments, where the compound is therapeutic, the compound may be an anti-cancer agent. In embodiments, where the compound is an anti-cancer agent, the compound may be doxorubicin. Additionally, in embodiments, where the compound is therapeutic, the compound may be selected from an antigenic peptide and a polynucleotide that encodes an antigenic peptide.

In any of the above embodiments for a composition for delivery of a compound, the composition may include an agent to maintain osmotic pressure of the EV. In embodiments including an agent to maintain osmotic pressure of the EV, the agent may be a saline buffer.

Methods of Producing EVs Derived from a Mammalian Cell

In some embodiments, EVs may be produced by incubating a mammalian cell with a cross-linking agent and a reducing agent. In these embodiments to produce an EV, the cross-linking reagent may be selected from formaldehyde or paraformaldehyde. In either of the above embodiments of methods to produce EVs, the reducing agent may be selected from dithiothreitol, cysteine and glutathione. In any of the above embodiments of methods to produce EVs, the cross-linking agent may be paraformaldehyde, and the reducing agent may be dithiothreitol. In the above embodiments of methods to produce EVs, where the cross-linking agent is paraformaldehyde, the paraformaldehyde may be at a concentration of about 2.5 mM to about 2.5 M. In the above embodiments of methods to produce EVs, where the reducing agent is dithiothreitol, the dithiothreitol may be at a concentration of about 0.2 mM to about 200 mM. In the above embodiments of methods to produce EVs, where the cross-linking agent is paraformaldehyde and the reducing agent is dithiothreitol, the concentration of paraformaldehyde may be at a concentration of 25 mM, and the dithiothreitol may be at a concentration of 2 mM.

In any of the above embodiments of methods to produce EVs, the EVs may be incubated with a compound. In embodiments of methods to produce EVs, where the EVs are incubated with a compound, the EVs may be incubated with a compound at about 37° C. In embodiments where the EVs may be incubated with a compound, the concentration may be at concentration of at least 100 μg/mL. Further, in embodiments where the EVs may be incubated with a compound, the EVs may be incubated with the compound for at least 30 minutes, 1 hour, 2 hours, 3 hours, 4 hours, 5 hours, 6 hours, 12 hours, or 24 hours. In any of the embodiments where the EVs may be incubated with a compound, the compound may be doxorubicin.

In any of the above embodiments of methods to produce EVs, the method may further include treating the composition with an agent to maintain the osmotic pressure of the EVs. In embodiments where the method to produce EVs includes treating the composition with an agent to maintain the osmotic pressure of the EVs, the agent to maintain the osmotic pressure may be a saline buffer.

Methods to Treat a Disease or Disorder

Some embodiments of the present invention may be a method of treating a disease or disorder comprising administering a composition for the delivery of a compound as described above—in which the composition includes a therapeutic agent, for example an anticancer agent, doxorubicin, or an antigenic peptide and a polynucleotide that encodes an antigenic peptide—to a subject suffering from a disease or disorder. In the above embodiment of a method of treating a disease or disorder, the mammalian cell used in the compound may be harvested from the subject. In either of the above embodiments, the cell may be a tumor cell. In embodiments, where the cell is harvested from a tumor cell, the EVs may be administered to or in proximity to tumor tissue.

In embodiments of a method of treating a disease or disorder, where the cell is a mammalian cell from the subject, the mammalian cell may be an antigen-displaying cell from the subject. In embodiments of a method of treating a disease or disorder, where the mammalian cell is an antigen-displaying cell, the cell may be a dendritic cell. In embodiments of a method of treating a disease or disorder, where the EVs are loaded with a compound—where the compound is a therapeutic agent, an imaging agent, an anti-cancer agent, or doxorubicin—the compound may be a vaccine for the disease or disorder.

Methods to Activate T Cells

Some embodiments of the invention may consist of a method of activating T cells comprising administering a composition for the delivery of a compound as described above—in which the composition is therapeutic, an anti-cancer agent, doxorubicin, or an antigenic peptide and a polynucleotide that encodes an antigenic peptide—into a subject. In the above embodiment of a method of activating T cells, the mammalian cell may be a dendritic cell.

Methods to Stimulate an Immune Response

Some embodiments of the present invention may consist of a method to stimulate an immune response comprising administering a composition for the delivery of a compound as described above—in which the composition is therapeutic, an anti-cancer agent, doxorubicin, or an antigenic peptide and a polynucleotide that encodes an antigenic peptide—into a subject. In the above embodiment of a method to stimulate an immune response, the mammalian cell may be a dendritic cell.

Embodiments of EV Production and Characterization

Figure 3:
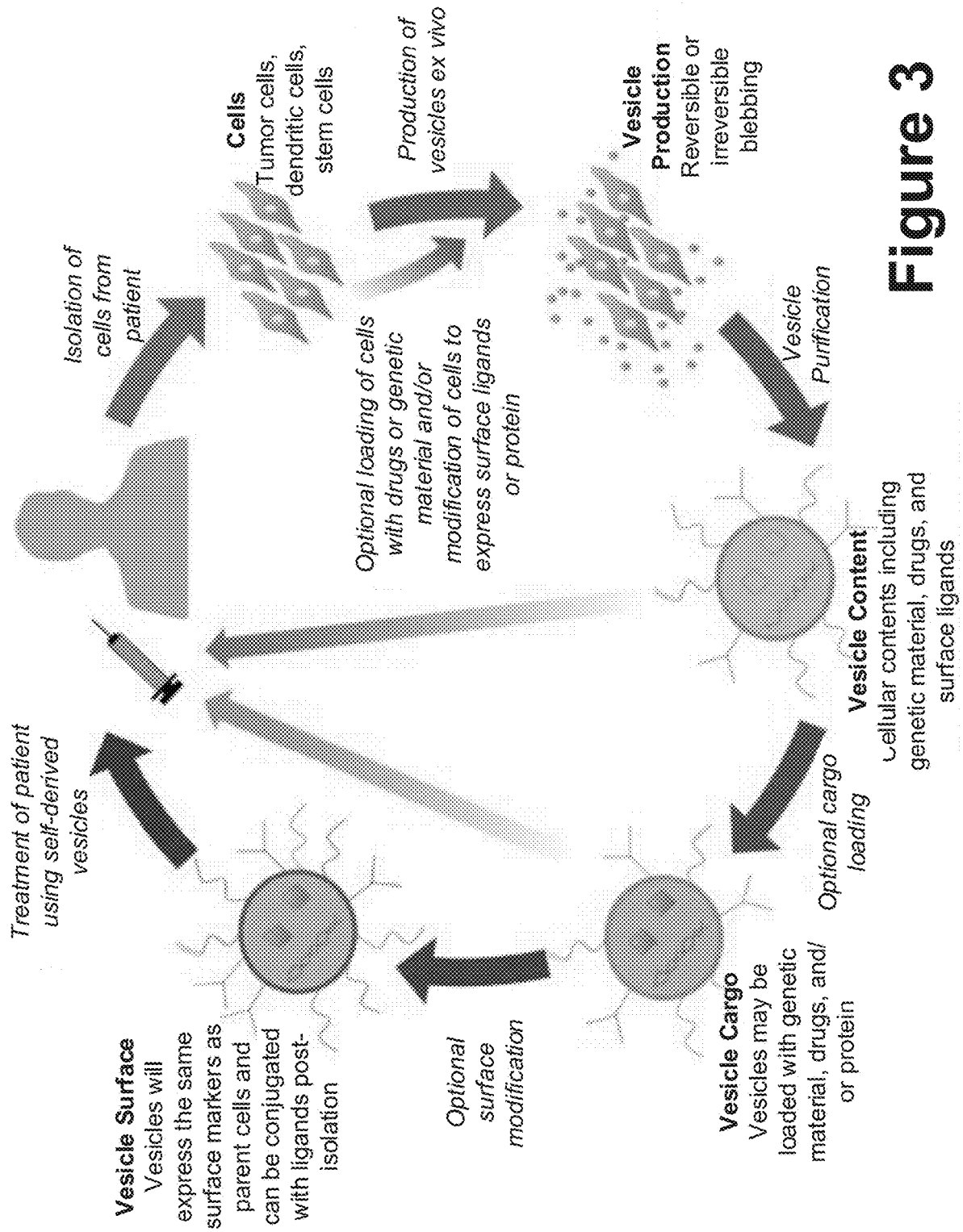
FIG. 3 illustrates the alteration of a biological process associated with extracellular vesicle formation in accordance with various embodiments of the invention.

Formation of EVs requires the biological process known as blebbing, which is the protrusion and retraction of portions of the plasma membrane. Blebbing is a result of changes in hydrostatic pressure, which are counteracted by cytoskeletal mechanisms (G. T. Charras, et al., J. Cell Biol. 175, 477-90 (2006), the disclosure of which is incorporated herein by reference). The opposing forces between the hydrostatic pressure of the cytoplasm and the retraction of the actin filaments determines whether a vesicle is released or the bleb retracts (J. Hagmann, M. M. Burger, & J. A. Theriot, J. Cell. Biochem. 73, 488-99 (1999), the disclosure of which is incorporated herein by reference). Accordingly, blebbing relies heavily on actin and myosin function. FIG. 3 depicts crosslinking-derived EVs prior to and following isolation and purification.

Figure 4:
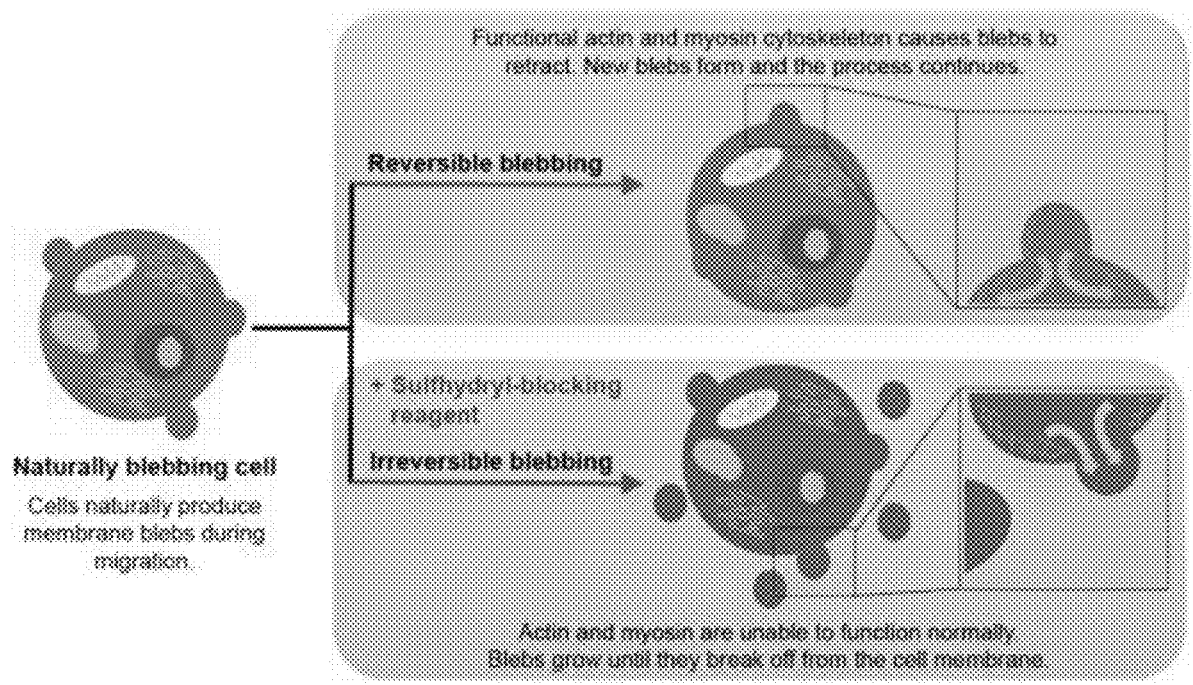
FIG. 4 illustrates the alteration of a biological process associated with extracellular vesicle formation in accordance with various embodiments of the invention.

As shown in FIG. 4, exposure of cells to sulfhydryl blocking reagents induces a state of irreversible blebbing. Concentration of sulfhydryl blocking reagents affects actin-myosin function and also correlates with media osmolarity. This implies significance of hydrostatic pressure and actin-myosin function on blebbing.

EV formation by sulfhydryl blocking reagents, in accordance with various embodiments of the invention, is highly advantageous because of its extremely rapid rate of EV production. Other methods to produce EVs, such as calcium- and stress-induced EV production, requires between 12 hours and several days to achieve significantly improved yields. Methods in accordance with embodiments described here can form similar amount of EVs in just one hour. Additionally, EVs, generated as described, are relatively simple to characterize and modify because the vesicles have similar membrane composition and intravesicular cytosol components to the cells they are derived from.

Figure 5:
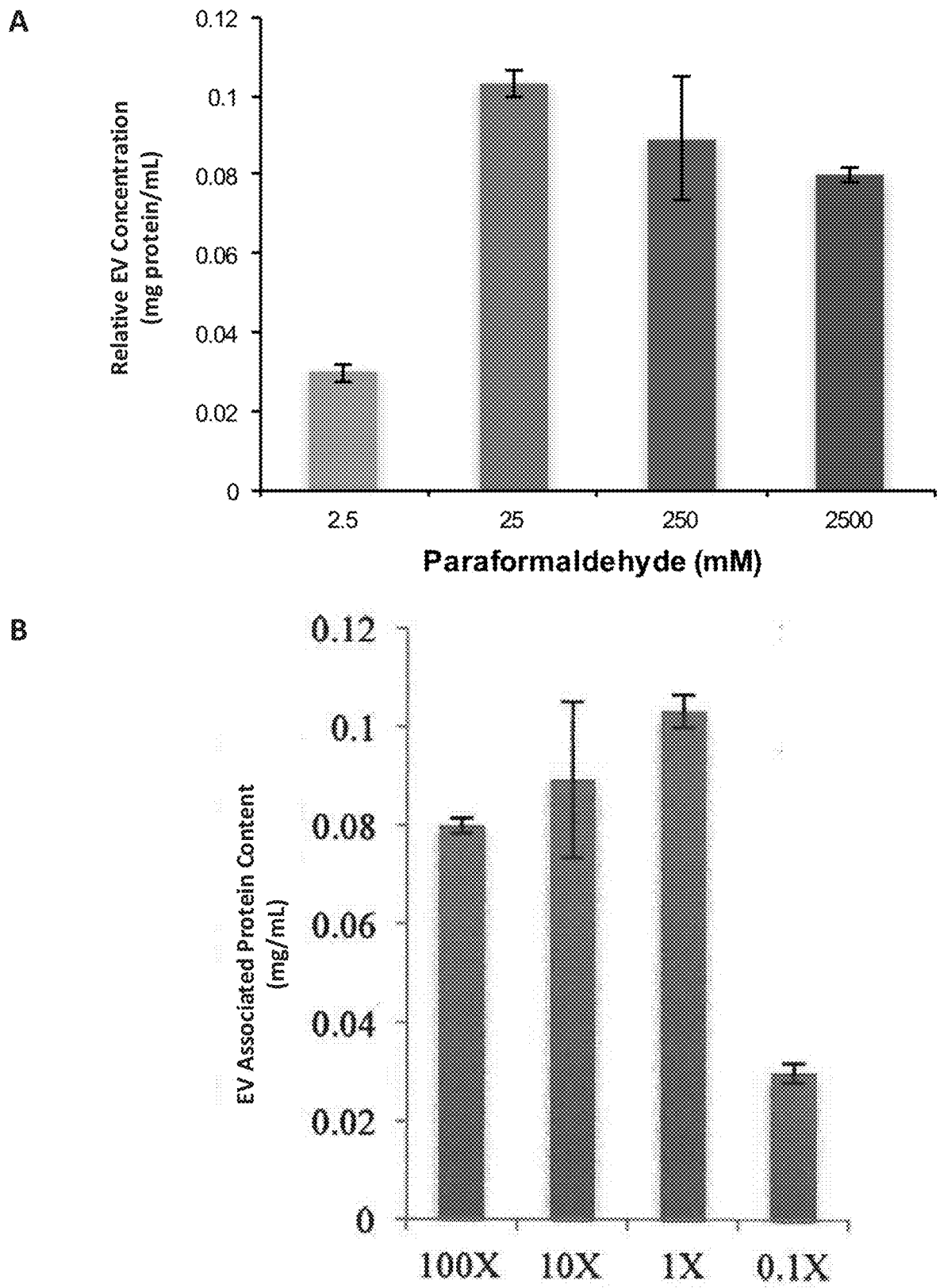
FIG. 5A is a bar chart depicting concentrations of paraformaldehyde and effects on extracellular vesicle associated protein content generated in accordance with various embodiments of the invention.
FIG. 5B is a data graph depicting concentrations of sulfhydryl blockers and effects on extracellular vesicle associated protein content generated in accordance with various embodiments of the invention.

In FIG. 5 describes embodiments of the production of EVs, where the concentrations of sulfhydryl blocking reagents have been altered. Specifically, FIG. 5A demonstrates embodiments where the concentration of paraformaldehyde has been altered to show maximum production levels at 25 mM paraformaldehyde with 2 mM dithiothreitol. FIG. 5B shows embodiments where HeLa cells were exposed to various concentrations of sulfhydryl blocking reagents, such that 1×=25 mM paraformaldehyde with 2 mM dithiothreitol. EVs were isolated and quantified using a BCA protein assay. These data show that the production of EVs with HeLa cells is highest at 25 mM paraformaldehyde with 2 mM dithiothreitol, as compared to other concentrations tested.

Figure 6:
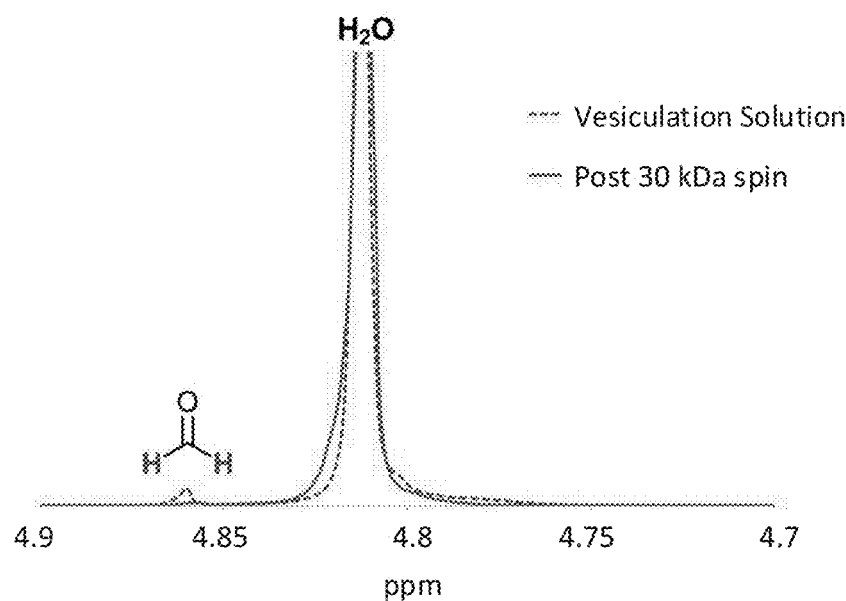
FIG. 6 depicts the removal of formaldehyde from various embodiments of the invention after purification.

In various embodiments, EVs may be collected by any suitable means to separate EVs from cells or cell debris. In some embodiments, to isolate EVs, cells were removed by centrifugation at 1,200 rpm for 5.5 minutes followed by removal of cell debris and micro-sized vesicles at 10,000 rpm for 10 minutes. EVs were concentrated with a 30 kDa centricon (4,500 rpm for 15 minutes); the EV-containing supernatant was concentrated and washed with an equivalent volume of PBS twice. Upon production of EVs in embodiments of this disclosure, formaldehyde residue may be removed using centrifugation, as shown in FIG. 6. The presence of formaldehyde in the resulting EV collection was measured by $^1$H NMR. It should be noted that an embodiment removing formaldehyde by centrifugation is only exemplary, and residue from any added reagents may be removed by any suitable means, including centrifugation, absorption, neutralization, or other means known in the art.

Figure 7:
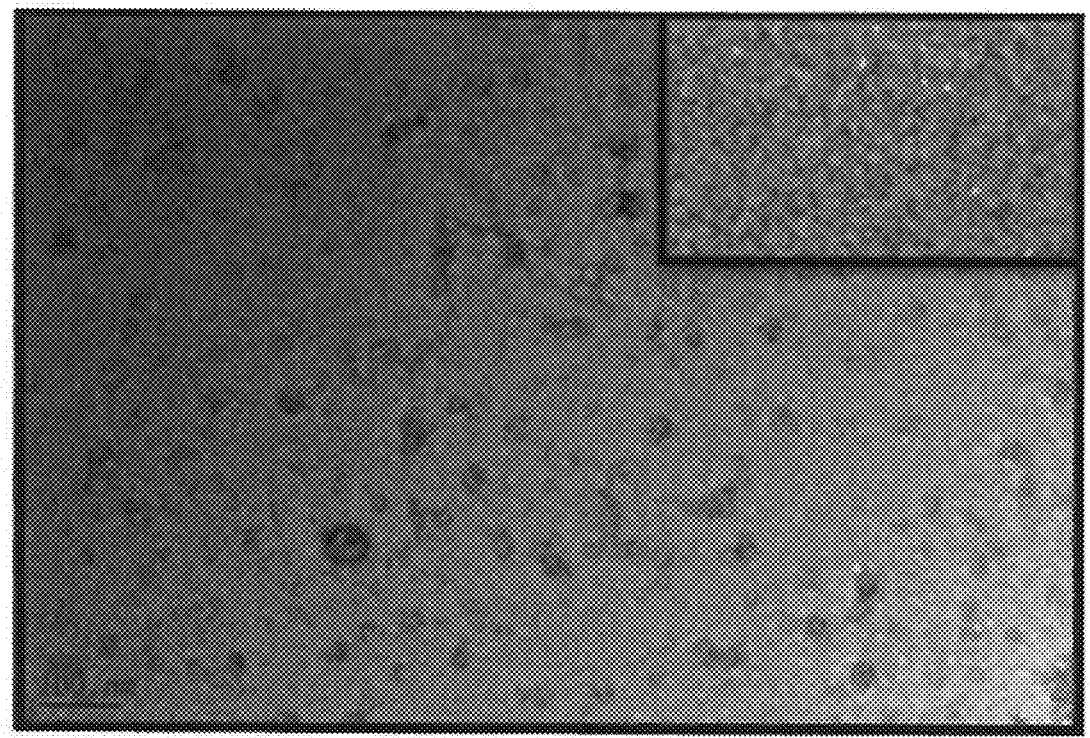
FIG. 7 is an electron microscope image of extracellular vesicles in accordance with various embodiments of the invention.
Figure 8:
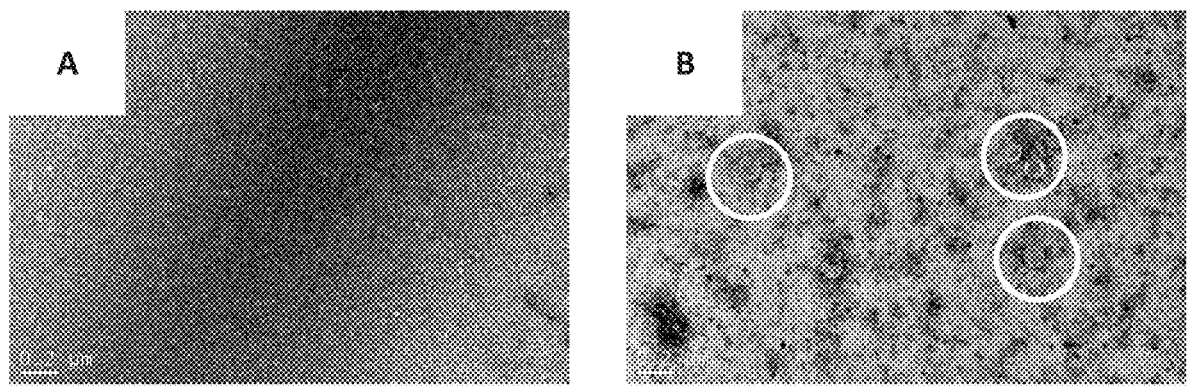
FIG. 8 provides electronic microscope images comparing supernatants of EL4 cells treated without or with sulfhydryl blocking reagents generated in accordance with various embodiments of the invention.

To analyze the lower size limit for EV production by sulfhydryl blocking reagents, EVs may be analyzed by means such as transmission electron microscopy (TEM). FIG. 7 demonstrates an embodiment where the supernatant of vesiculating HeLa cells was analyzed by TEM. HeLa cells treated with paraformaldehyde (PFA) and dithiothreitol (DTT), in accordance with various embodiments of the invention, generate a large amount of EVs as secondarily confirmed by TEM measurements. Since the control (inset) does not show EVs, these nano-sized EVs are unlikely to be exosomes generated by normal cellular processes. Instead, sulfhydryl blocking reagent-induced blebbing results in cells shedding nano-sized EVs. Additionally, FIG. 8 shows a TEM image of EL4 cells treated with and without PFA/DTT. TEM images in FIG. 8A demonstrate that the supernatant from EL4 cells incubated in serum-free/reagent-free media have little or no vesicles, while the EL4 cells incubated with serum-free media containing 25 mM paraformaldehyde and 2 mM dithiothreitol for 4 hours, however, had many nano-sized EVs as indicated by the circles. In order to more clearly examine the EVs, the cells, debris and giant plasma membrane vesicles were removed by centrifugation at 16,100×g. The EVs were then isolated and concentrated by centrifugation at 100,000×g.

Figure 9:
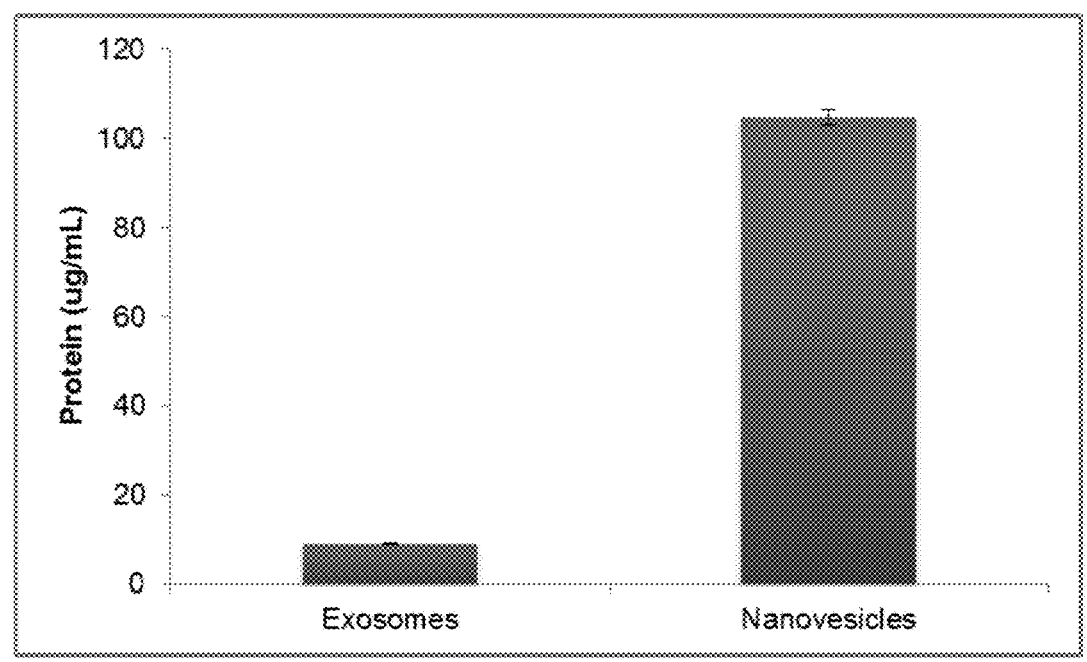
FIG. 9 is a data graph depicting extracellular vesicles production in the presence and absence of sulfhydryl blocking reagents.

EVs are a promising potential therapeutic carrier. Low yield of intrinsic vesicle production is a problem. However, sulfhydryl blocking reagents can be used to produce EVs appropriate in size for carrying therapeutic cargo. FIG. 9 demonstrates embodiments of EV production in the presence and absence of sulfhydryl blocking reagents. EL4 cells were incubated at 100,000 cells/mL in 5 mL of either DMEM (without FBS) for 24 hours or PBS with 90 µL 4% PFA solution and 10 µL 1 M DTT for 2 hours at 37° C. After cells and cell debris were removed by centrifugation at 1200 rpm for 5.5 min, micro-sized vesicles were pelleted at 13,200 rpm for 10 minutes, leaving the EVs in the supernatant. Then, EVs were isolated by 30 kDa centricons at 4,500 rpm for 10 minutes. The EVs were washed three times with 5 mL of DPBS to remove free protein and sulfhydryl blocking reagents. Protein content was assessed using a BCA protein assay (FIG. 9). Vesicles produced from cells that were not exposed to sulfhydryl blocking reagents are called exosomes. Sulfhydryl blocking reagents produce a significantly greater (10-fold) amount of EVs compared to naturally occurring exosomes, based on protein quantification over a significantly shorter time-frame of production.

Figure 10:
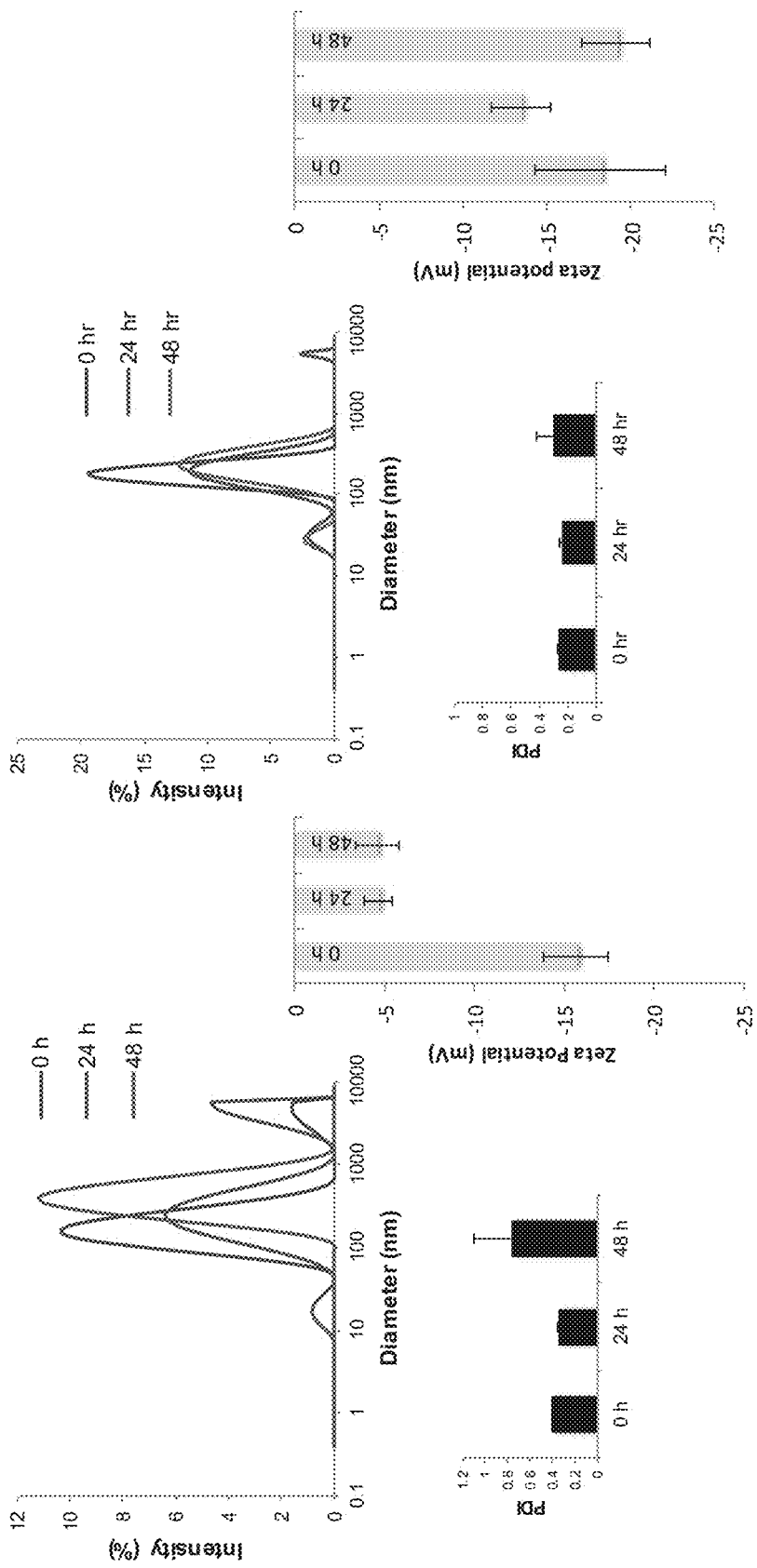
FIG. 10 describes the stability of the extracellular vesicles produced by various embodiments of this invention as compared to naturally occurring exosomes.

Additionally, the stability of EVs produced by embodiments of the invention may be measured by various means. FIG. 10 describes the stability of exosomes versus EVs produced according to certain embodiments. In this figure, the size range of exosomes and EVs of some embodiments are shown as measured by dynamic light scattering (DLS) as measured at 0, 24, and 48 hours. Additionally, the polydispersity index (PDI) shows that as time passes, exosomes increase in polydispersity, while EVs of certain embodiments remain stable. Also, the anionic surface charge of exosomes decreased over time, while EVs of some embodiments remain relatively stable after 24 and 48 hours, when compared to the initial measurement.

Figure 11:
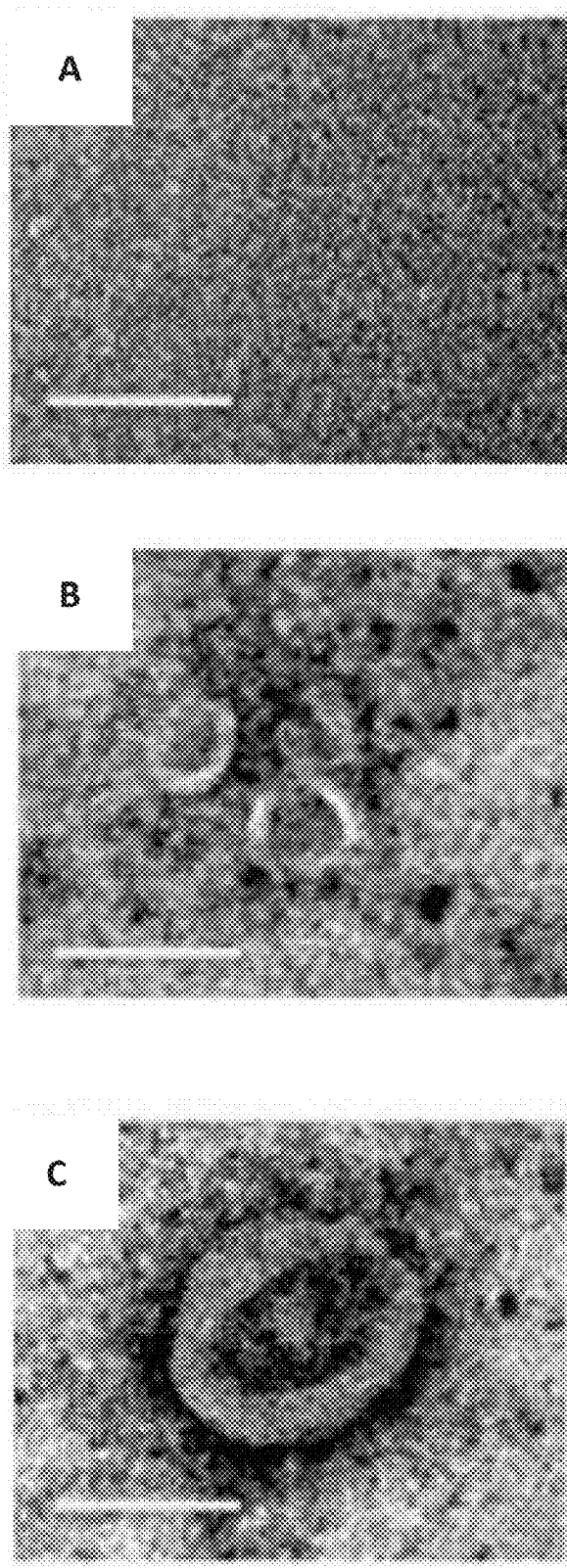
FIG. 11 is a composite of three electron microscope images of supernatants derived from EL4 cells with various treatments: untreated and unloaded (FIG. 11A), treated with sulfhydryl blocking agents (FIG. 11B), treated with sulfhydryl blocking agents and loaded with DOX (FIG. 11C), generated in accordance with various embodiments of the invention.

Turning now to FIG. 11, describing the ability to generate and use EVs to carry a therapeutic drug. Specifically, FIG. 11 demonstrates the size of EVs produced in accordance with various embodiments of the invention. In particular, FIG. 11A is a TEM image of supernatant collected from control EL4 cells, which have not been exposed to sulfhydryl blocking reagents. FIG. 11B shows a representative TEM image of EL4 EVs of some embodiments produced via sulfhydryl blocking. FIG. 11C shows EL4 EVs, which have been loaded with doxorubicin (DOX) after being produced by sulfhydryl blocking. The scale bars in FIG. 11 equal 200 nm.

Figure 12:
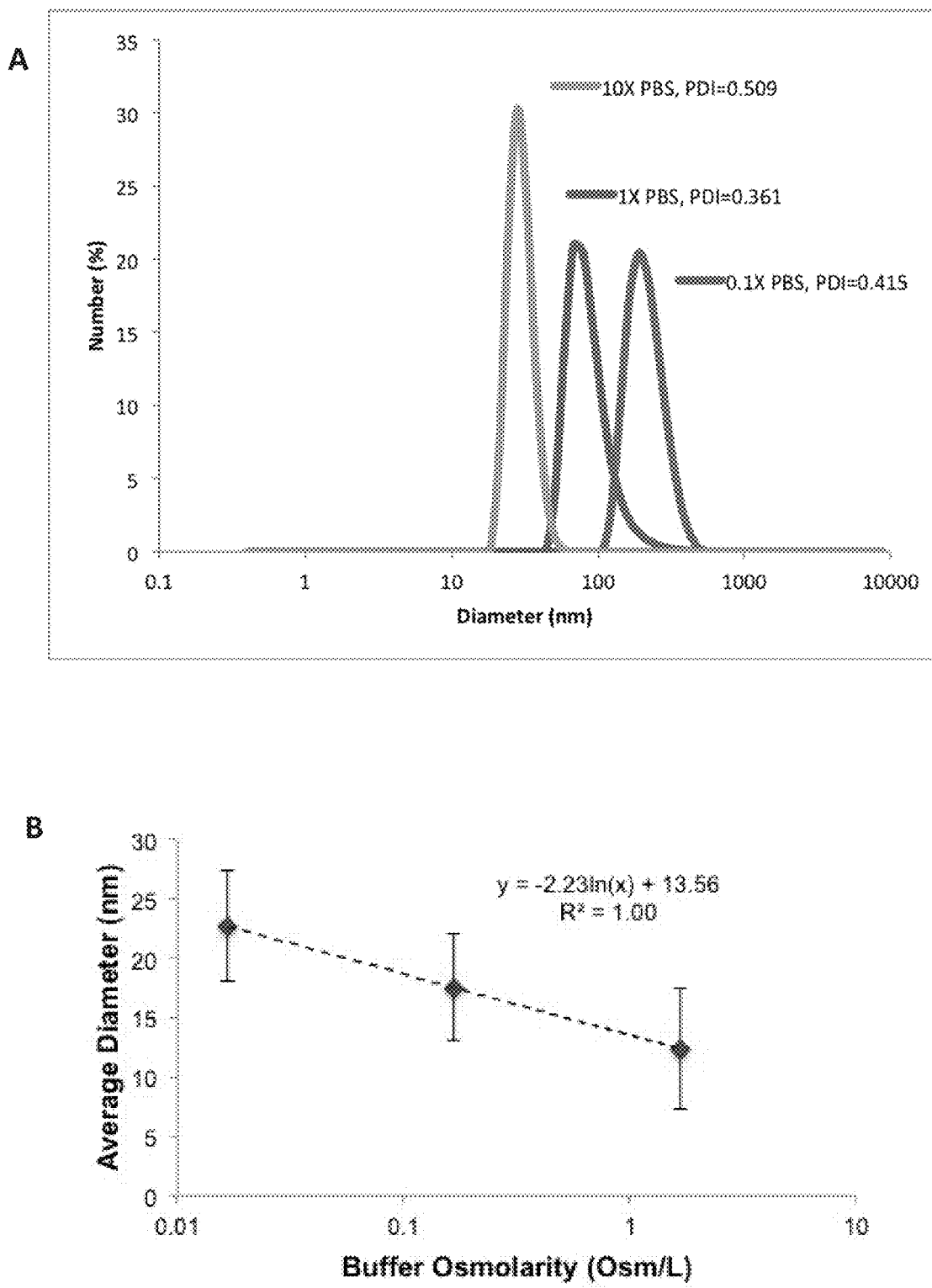
FIG. 12A provides the results of a dynamic light scattering assay showing the size range of nano-scale extracellular vesicles produced by different concentrations of phosphate buffered saline of various embodiments of this invention.
FIG. 12B is a data graph depicting the correlation between extracellular vesicle size and osmolarity in accordance with various embodiments of the invention.
FIG. 12C provides the results of a dynamic light scattering assay showing the size range of micro-scale extracellular vesicles produced by different concentrations of phosphate buffered saline of various embodiments of this invention.
FIG. 12D is a bar graph showing the average size and standard distribution of extracellular vesicles produced by different concentrations of phosphate buffered saline in accordance with various embodiments of the present invention.
FIG. 12E shows images of extracellular vesicles produced by varying the concentration of phosphate buffer in accordance with various embodiments of the invention.

Additionally, in embodiments of the invention, the size of EVs being produced can be altered by adjusting the osmolarity of the buffer (FIG. 12). In some embodiments, phosphate-buffered saline (PBS) may be used along with the sulfhydryl blocking reagents to generate EVs. In this figure, EVs were generated using 25 mM PFA, 2 mM DTT along with PBS at 0.1×, 1×, and 10× concentrations. The size distribution of EVs produced in these embodiments was measured via a DLS assay. The increased concentration of PBS led to smaller EVs produced in some embodiments. These results indicate that the size of EVs produced in some embodiments may be customized to suit specific needs.

Specifically, FIG. 12A demonstrates the effect of increasing the buffer concentration to generate EVs in the 10 nm to 1,000 nm size-range (nano-scale EVs) of some embodiments. Embodiments of nano-scale EVs may be generated by inducing vesiculation in cells, followed by a 30 kDa centrifugal filtration as described in this disclosure. In some embodiments, cells may be removed from the solution by an initial 1,200 rpm centrifugation prior to the 30 kDa centrifugal filtration. Additionally, FIG. 12B demonstrates a similar result showing a linear relationship between increased osmolarity and smaller EVs.

Similarly, FIGS. 12C and 12D demonstrate the effect of increasing the buffer concentration to generate EVs in the 500 nm to greater than 15,000 nm size-range (micro-scale EVs) in other embodiments. Embodiments of micro-scale EVs may be generated by inducing vesiculation in cells followed by centrifugation at 1,200 rpm to remove cells. The remaining supernatant may be further centrifuged at 9,300×g to isolate micro-scale EVs. It should be noted that the supernatant remaining after isolation of micro-scale EVs may also be submitted to a 30 kDa centrifugal filtration to further isolate nano-scale EVs. Images of micro-scale EVs of various embodiments are shown in FIG. 12E. In these images, the size and distribution of micro-scale EVs generated using sulfhydryl blocking reagents along with varying concentrations of PBS are shown.

The size of EVs produced in certain embodiments may also be adjusted by using alternative buffers. FIG. 13A demonstrates the effect of several buffers on the size of EVs produced by some embodiments as measured by DLS. In this figure, the buffers DPBS, DMEM, and GPMV were shown to produce EVs with sulfhydryl blocking in various size ranges, including into the larger, µm-sized EVs.

Additionally, not all buffers produce EVs at the same rate. FIG. 13B demonstrates the production of EVs by various buffers as determined by a BCA assay to assess the protein content. As shown, PBS and DPBS buffers are more efficient than GPMV and DMEM buffers. FIG. 13C demonstrates PDI of EVs produced by PBS and GPMV buffers. As indicated in FIG. 13C, PBS buffer produces EVs with a lower PDI, indicating that PBS creates more uniformly sized EVs over GPMV, which has a PDI of approximately 1, which indicates nearly complete polydispersity of EVs produced with GPMV. Further, FIG. 13D demonstrates nano-sized EVs produced by vesiculation with 0.1 M HEPES buffer and 0.9% saline, which show a very broad size distribution and high polydispersity among these buffers. Similarly, FIG. 13E shows production of micro-sized EVs using 0.1 M HEPES buffer and 0.9% saline, which show a very broad size distribution and high polydispersity among these buffers.

Figure 13:
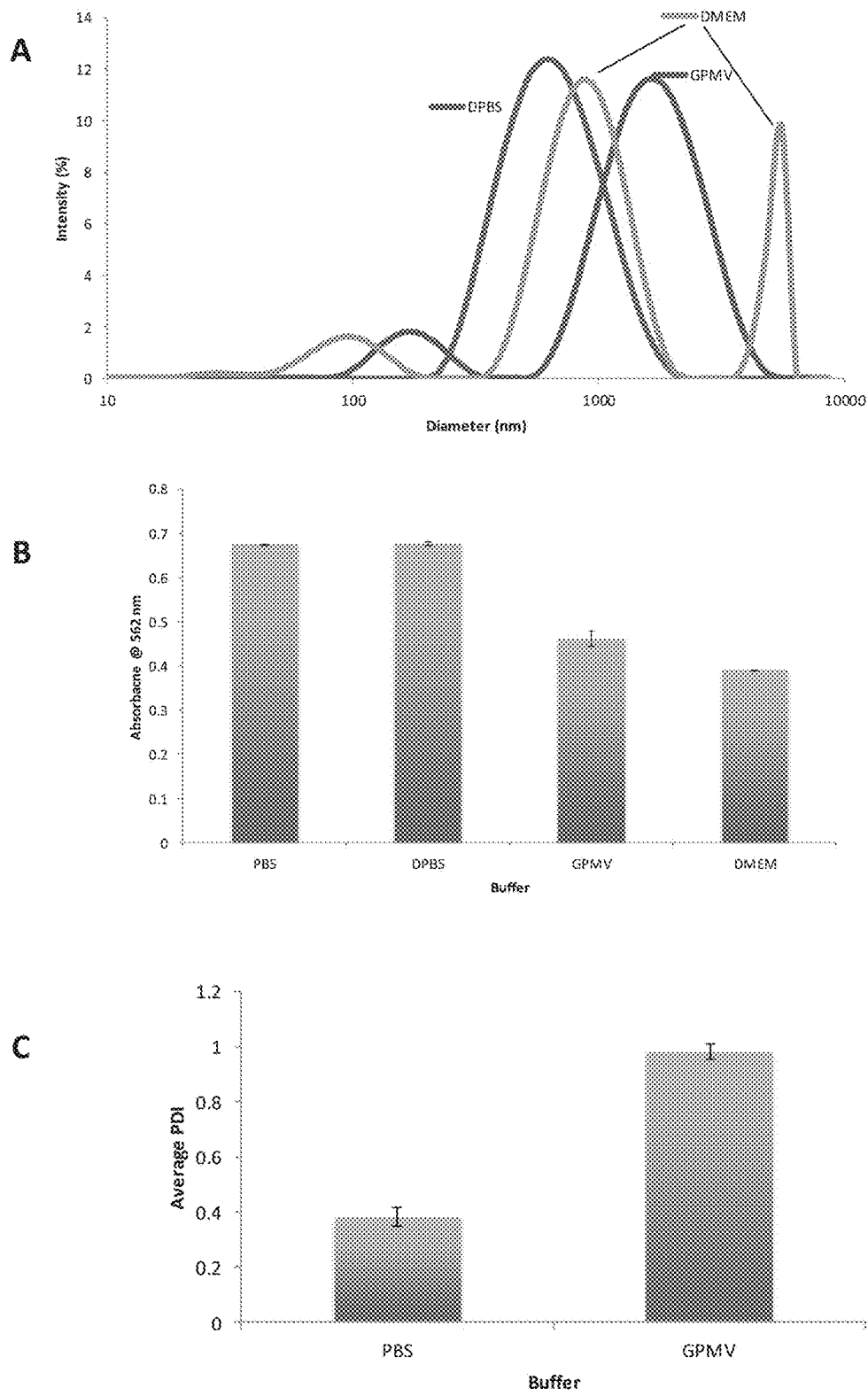
FIG. 13A provides the results of a dynamic light scattering assay showing the size range of extracellular vesicles produced by different buffers of various embodiments of this invention.
FIG. 13B is a bar graph showing the amount of extracellular vesicles produced by various buffers under the same conditions of various embodiments of the invention.
FIG. 13C is a bar graph depicting the polydispersity index of extracellular vesicles produced by different buffers of various embodiments of the invention.
FIG. 13D shows the size and distribution of nano-scale extracellular vesicles produced in the presence of HEPES and saline buffers in accordance with various embodiments of the invention.
FIG. 13E shows the size and distribution of micro-scale extracellular vesicles produced in the presence of HEPES and saline buffers in accordance with various embodiments of the invention.

Each of these buffers shown in FIG. 13 may contain various components to balance osmotic pressure as well as supplement cellular growth. The results shown in FIG. 13 indicate that changing osmolarity of the solution is not the only factor in adjusting the average size, size distribution, or production rate of EVs produced by various embodiments.

Figure 14:
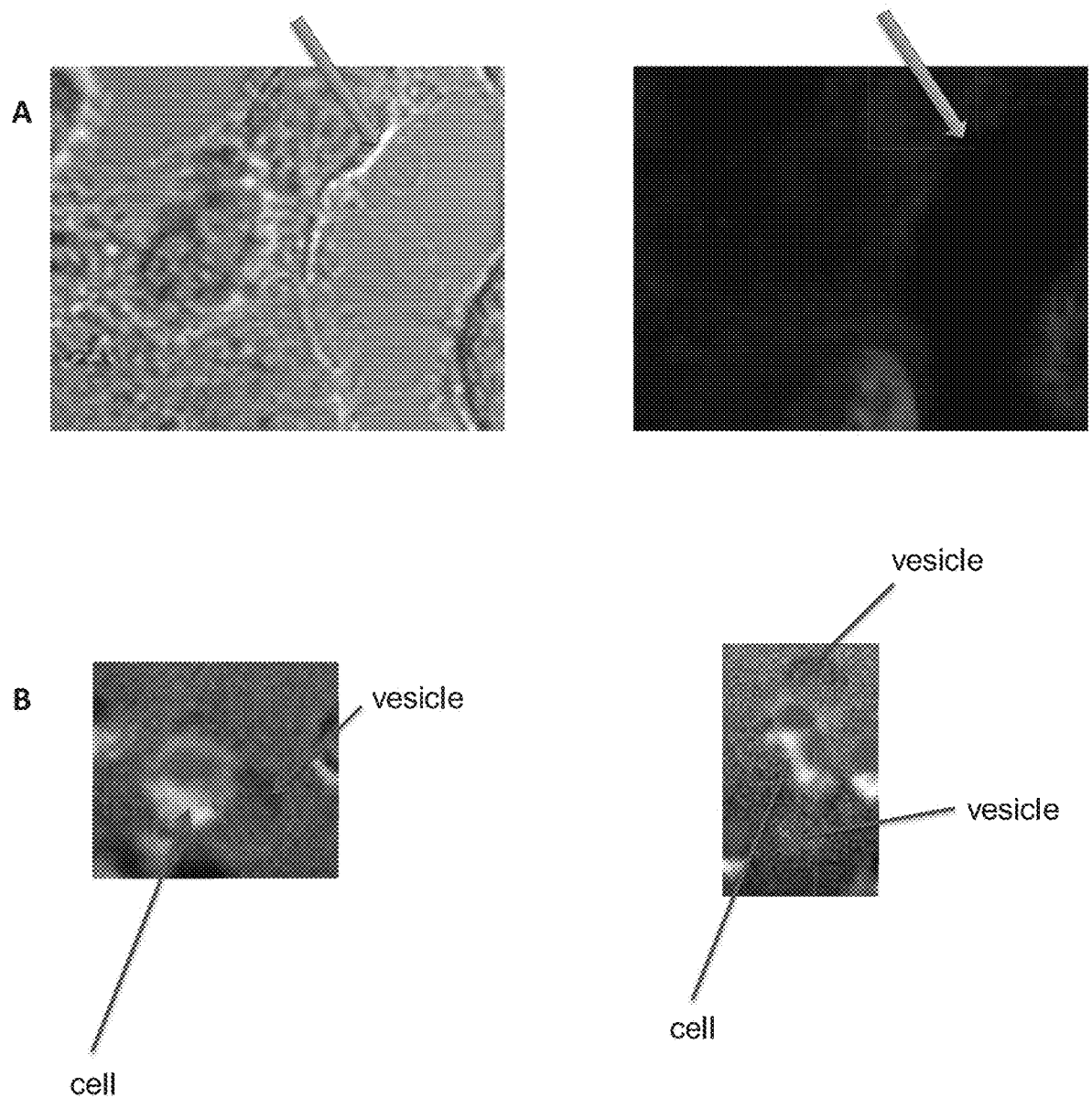
FIG. 14A and FIG. 14B depicts microscope images of extracellular vesicles being produced by various embodiments of the invention along with the presence of actin in the cell and vesicle.

Turning now to FIG. 14, which demonstrates the ability to assess the presence of actin within EVs produced in accordance of various embodiments of the invention. In FIG. 14A, left panel shows a light microscope image of a micro-scale EV being formed from a host cell, while FIG. 14A, right panel shows the presence of actin as stained with a fluorescent dye. Similarly, FIG. 14B overlays a fluorescent image onto a light image to show that EVs produced by some embodiments may be substantially free of actin.

Figure 15:
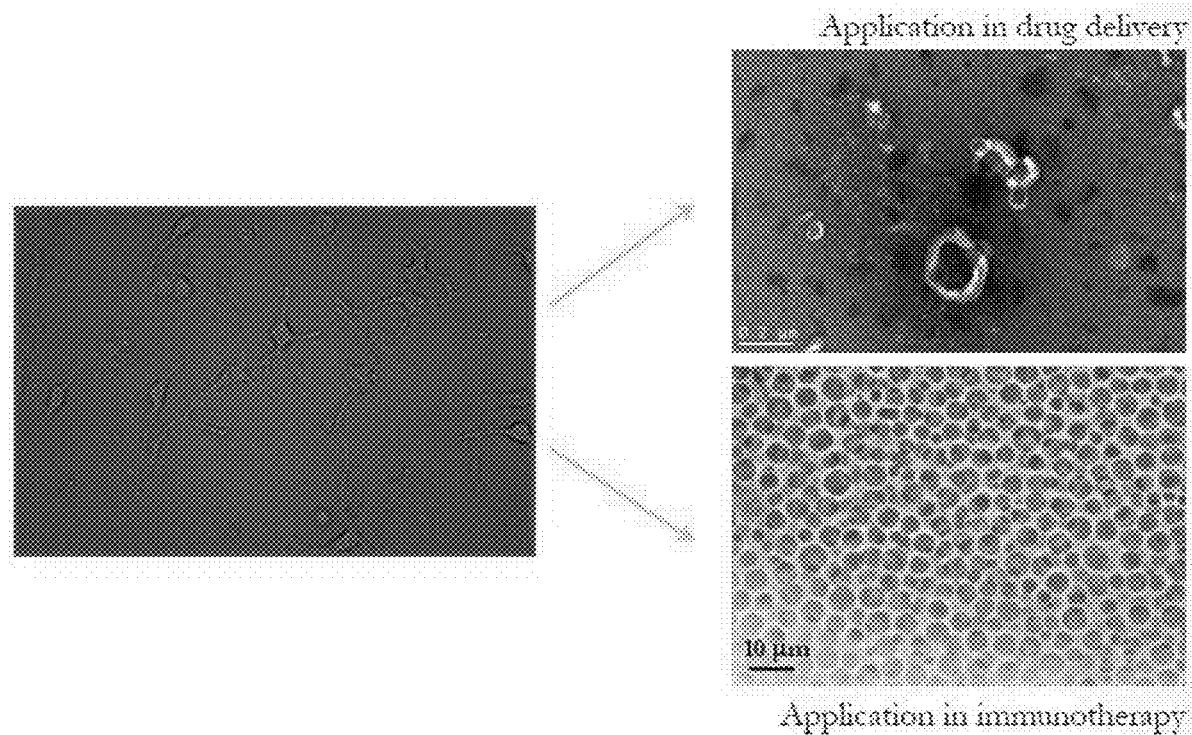
FIG. 15 shows electron microscope images of cells and extracellular vesicles, indicating the possible size range of extracellular vesicles that may be produced by various embodiments of the invention.

Biological data supports the generation and characteristic description of the EVs. Furthermore, the data supports the notion that the EVs can be used to a compound delivery system capable as a therapeutic treatment. The following data also details the scalability and enhanced production of EVs from a host source. Accordingly, these data support the various embodiments of the invention as described. Turning now to FIG. 15, certain embodiments may utilize various sizes of EVs produced by other embodiments. Specifically, smaller, nano-scale EVs may be more suitable for drug delivery, while larger micro-scale EVs may be more suitable for applications in immunotherapy.

Embodiments of EV Drug Delivery Vehicles

Some embodiments of the present disclosure may be used to deliver drugs or other therapeutic agent to an individual. Such a delivery mechanism could also be used to transport peptides, proteins, nucleic acids, or imaging agents. Examples of therapeutic agents could be synthetic or natural compounds, such as small molecules, nucleic acids, or peptides. Examples of such agents include drugs, hormones, enzymes, proteins, lipids, carbohydrates, glycoproteins, transcription factors, DNA, RNA, mRNA, modified mRNA, small RNAs, siRNA, miRNA, genes, transgenes, and dyes. Using many natural compounds may elicit a desired effect directly, such as an mRNA encoding a peptide for immediate transcription. Alternatively, some compounds may cause the desired tissue to generate the response, such that delivery of a transcription factor may activate an innate gene. Additionally, delivery of specific imaging agents may allow accumulation of dyes to a specific cell-type or tissue for imaging without background imaging signal being produced by neighboring tissue.

In some embodiments, agents of interest, including therapeutic, diagnostic, or a combination of therapeutic and diagnostic, may be loaded into cells prior to, concurrently with, after, or any combination thereof of the production of EVs. In such embodiments, harvested cells may be loaded with therapeutic agents or harvested cells may be induced to produce the agents of interest. In embodiments where the cells are loaded with agents of interest, the cells may be incubated with agents of interest in similar conditions as described within this disclosure to allow the cell to uptake the therapeutic agent. In embodiments where the cells are loaded by inducing a cell to produce the agents of interest, the cell may produce specific peptides, nucleic acids, or both peptides and nucleic acids with therapeutic properties. Therapeutic peptides may include small peptides, protein subunits, entire proteins, or any combination of the above. Therapeutic nucleic acids may include DNA or RNA, including genic sequences, plasmid DNA, tRNA, rRNA, mRNA, small RNAs, miRNA, siRNA, shRNA, crRNA, or any combination of nucleic acids produced within the cell. Additionally, ribonucleoproteins or any other form of protein-nucleic acid complex may be produced within a cell. In some embodiments, once the cells are loaded with the agents of interest, vesiculation may be induced. In other embodiments, vesiculation may be induced during the loading of the therapeutic agents into the cells. Situations were vesiculation may occur during loading may include where the cell is producing the therapeutic agents. Upon inducing vesiculation, EVs produced from the loaded cells may contain the agents of interest. EVs produced in accordance with embodiments of the invention may also be loaded with agents of interest via direct membrane penetration, chemical labeling and conjugation, electrostatic coating, adsorption, absorption, electroporation, or any combination thereof. Further, EVs produced in accordance with certain embodiments may undergo multiple loading steps, such that some agents of interest may be loaded prior to vesiculation, while additional agents of interest may be loaded during or after vesiculation. Additionally, EVs may be loaded with an agent of interest during vesiculation, and further loaded with another agent of interest after vesiculation.

Figure 16:
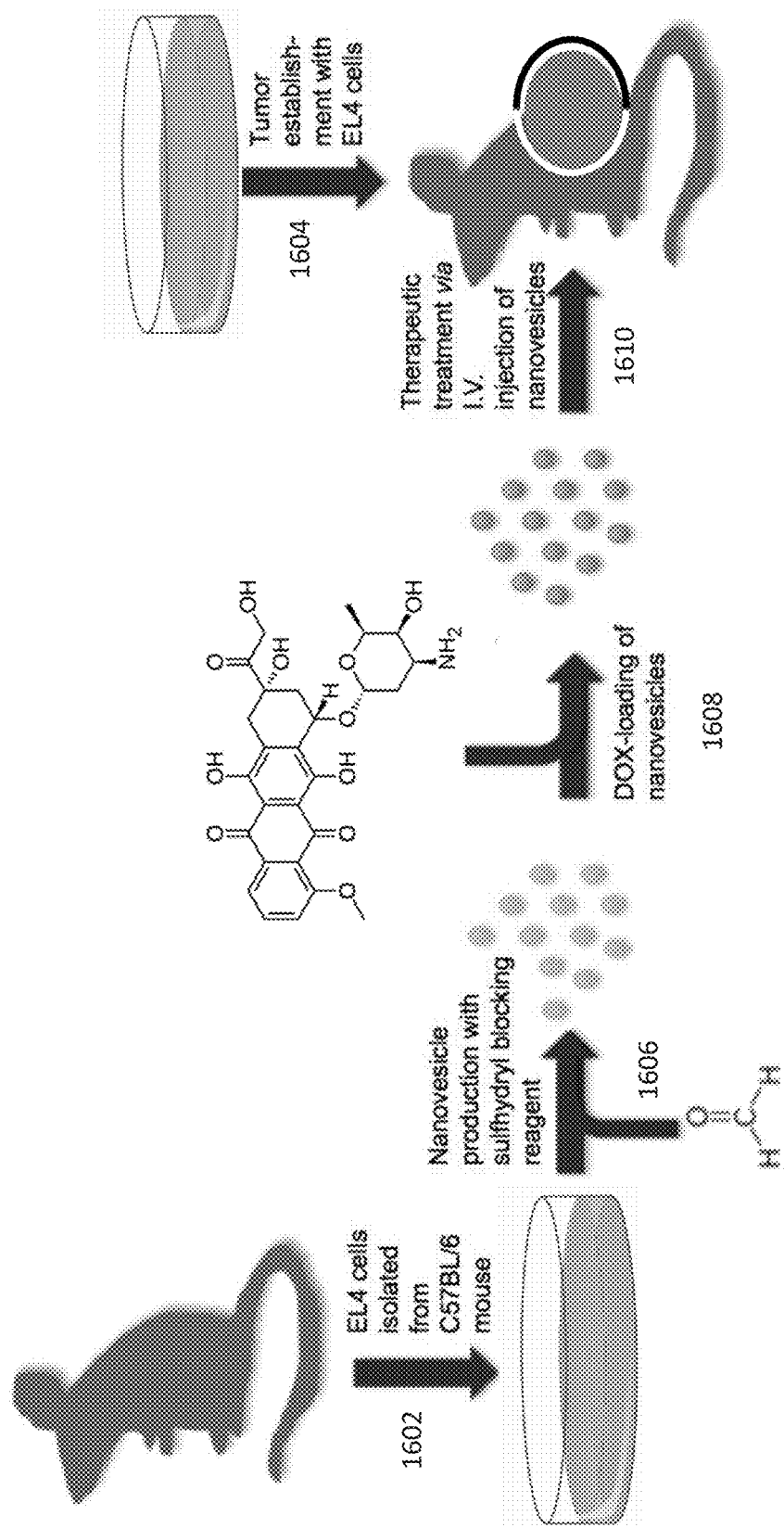
FIG. 16 illustrates a process for treating a tumor with DOX-loaded extracellular vesicles in accordance with an embodiment of the invention.

FIG. 16 demonstrates an example of one strategy to deliver a therapeutic drug to an individual in accordance with various embodiments. It should be noted that FIG. 16 is only exemplary and does not describe all possible ways to deliver a therapeutic drug to an individual in accordance with embodiments of the present invention. Specifically, FIG. 16 demonstrates the delivery of the drug, DOX to a mouse with an established tumor. In this figure, EL4 cells from a mouse have been isolated and placed into culture (1602). Additionally, a tumor is established in a mouse using EL4 cells (1604). Further, EVs have been produced from these cells by the use of sulfhydryl blocking reagents (1606). In this figure, formaldehyde is demonstrated as a possible reagent. EVs produced by sulfhydryl blocking are loaded with DOX (1608). Finally, the DOX-loaded EVs are provided to the mouse to treat the tumor established by the EL4 cells.

Figure 17A:
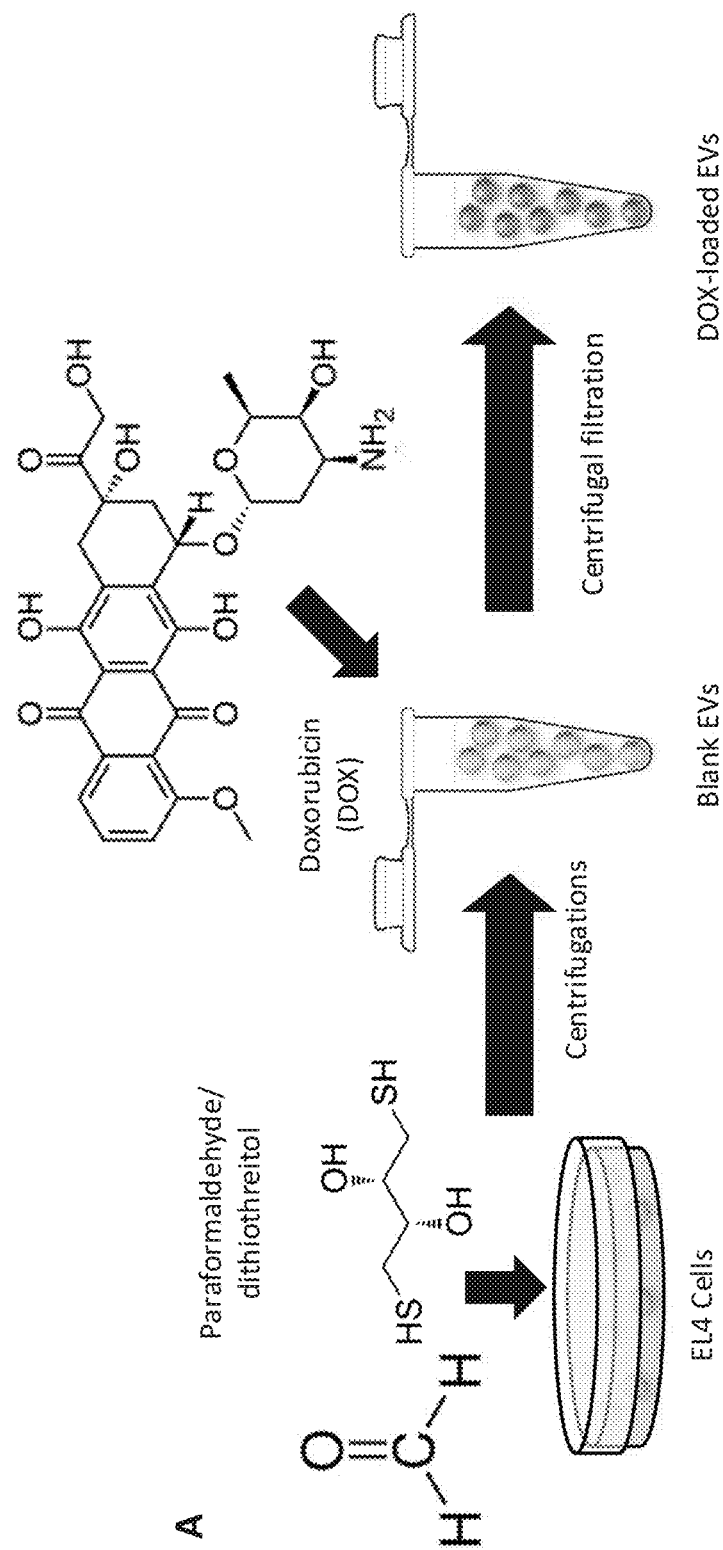
FIG. 17A illustrates the process of loading DOX into extracellular vesicles in accordance with an embodiment of the invention.
Figure 17B:
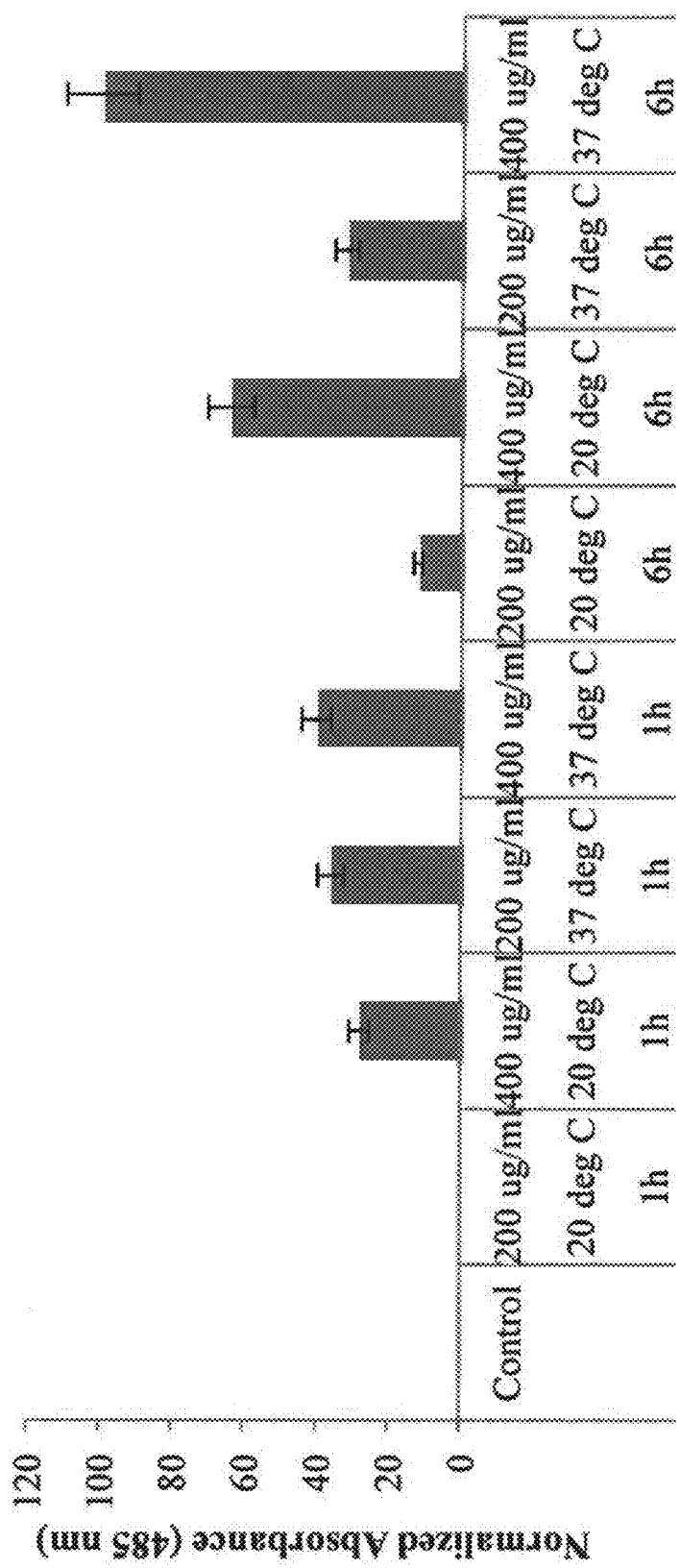
FIG. 17B is a data graph depicting the effects of concentration of compound, temperature, and time on compound loading of extracellular vesicles generated in accordance with various embodiments of the invention.
Figure 17C:
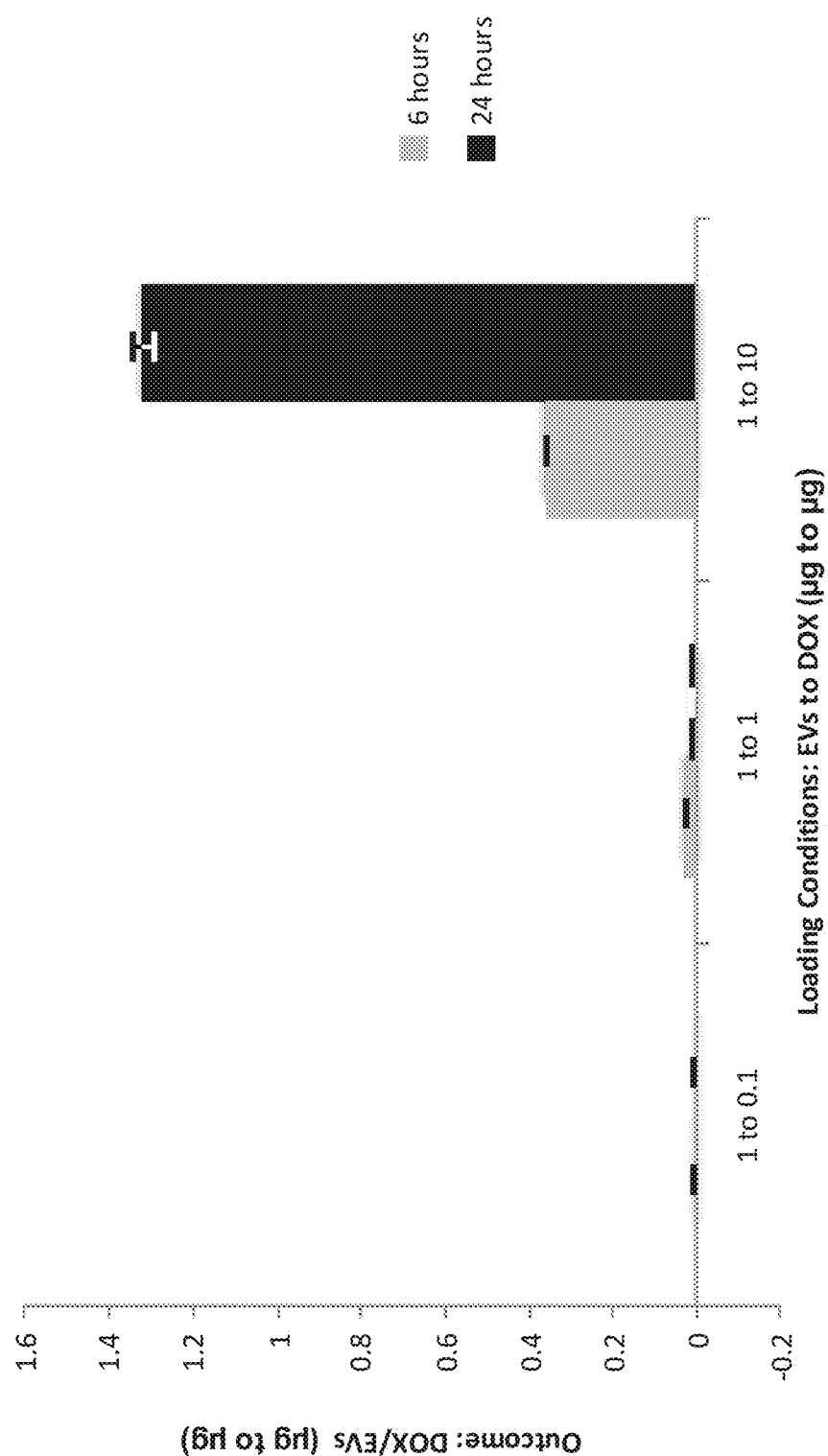
FIG. 17C depicts the effects of extracellular vesicle to DOX concentration of loading extracellular vesicles in accordance with various embodiments of the invention.

FIG. 17 further demonstrates examples of various conditions for loading EVs with a therapeutic agent in accordance with embodiments of the present invention. Specifically, FIG. 17A demonstrates the production of EVs by incubating EL4 cells with PFA and DTT. EVs produced may be collected by centrifugation. DOX or another therapeutic may be loaded into to the EVs, then collected through centrifugation. EVs have great potential as therapeutic carriers due to their small size and high biocompatibility. The EL4-derived EVs were loaded with a common chemotherapeutic drug, doxorubicin (DOX). DOX is known for high instances of cardiotoxicity, and therefore is an ideal candidate for targeted therapeutic delivery. Anticancer agent, DOX, was selected for studies due to its relatively low solubility and bioavailability and subsequent potential for improved biodistribution when delivered via drug-loaded EVs. DOX's intrinsic fluorescence also aids in confirmation of drug entrapment within EVs. DOX, a chemotherapeutic anthracycline antibiotic, exhibits red fluorescence (excitation: 480 nm, emission: 580 nm). Passive DOX loading of EVs was tested at different drug concentrations, temperatures and incubation periods (FIG. 17B). As expected, all three factors factor in DOX loading. Additionally, when the ratio of DOX to EVs was increased, the amount of DOX loaded into EVs also increased (FIG. 17C).

In embodiments of EV drug delivery vehicles, the EVs may be loaded with a compound by incubating cells or empty EVs with 25 µg/mL, 50 µg/mL, 100 µg/mL, 200 µg/mL, 300 µg/mL, 400 µg/mL, or 500 µg/mL of the compound. Additionally, the incubation may occur for 1 hour, 2 hours, 3 hours, 4 hours, 5 hours, 6 hours, 12 hours, 24 hours, or 48 hours. Alternatively, the loading conditions may occur at a ratio of EVs to a compound of 1:0.1, 1:0.2, 1:0.3, 1:0.4, 1:0.5, 1:0.6, 1:0.7, 1:0.8, 1:0.9, 1:1, 1:2, 1:2, 1:3, 1:4, 1:5, 1:6, 1:7, 1:8, 1:9, or 1:10.

Additionally, the polydispersity of compound-loaded EVs may have a similar polydispersity index (PDI) of unloaded EVs. As such, compound-loaded EVs may have a PDI of about 0.1, 0.2, 0.3, 0.4, 0.5, 0.6, 0.7, 0.8, 0.9, or 1.0.

Figure 18:
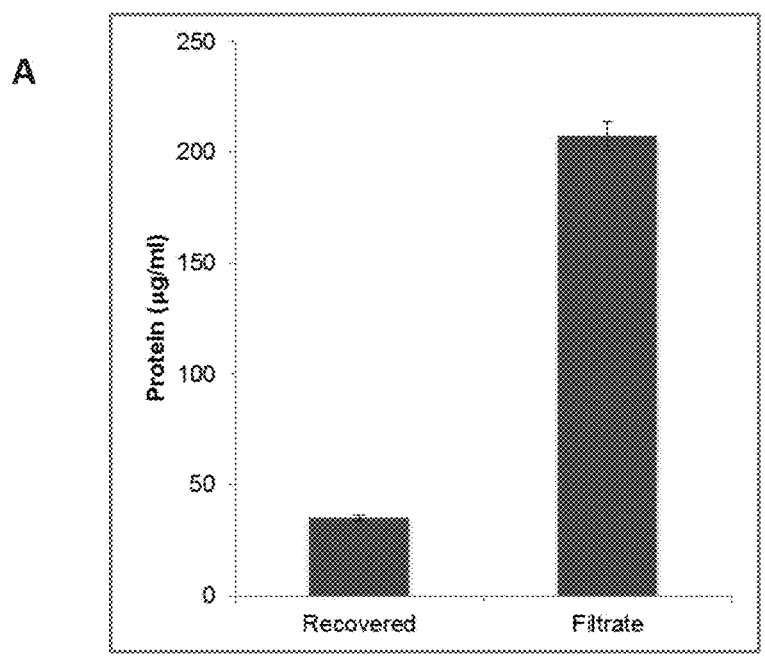
FIG. 18A is a data graph depicting the protein concentration in the recovered and filtrate portions after centrifugal filtration generated in accordance with various embodiments of the invention.
FIG. 18B is a data graph comparing size of unloaded extracellular vesicles with DOX-loaded extracellular vesicles generated in accordance with various embodiments of the invention.
Figure 18:
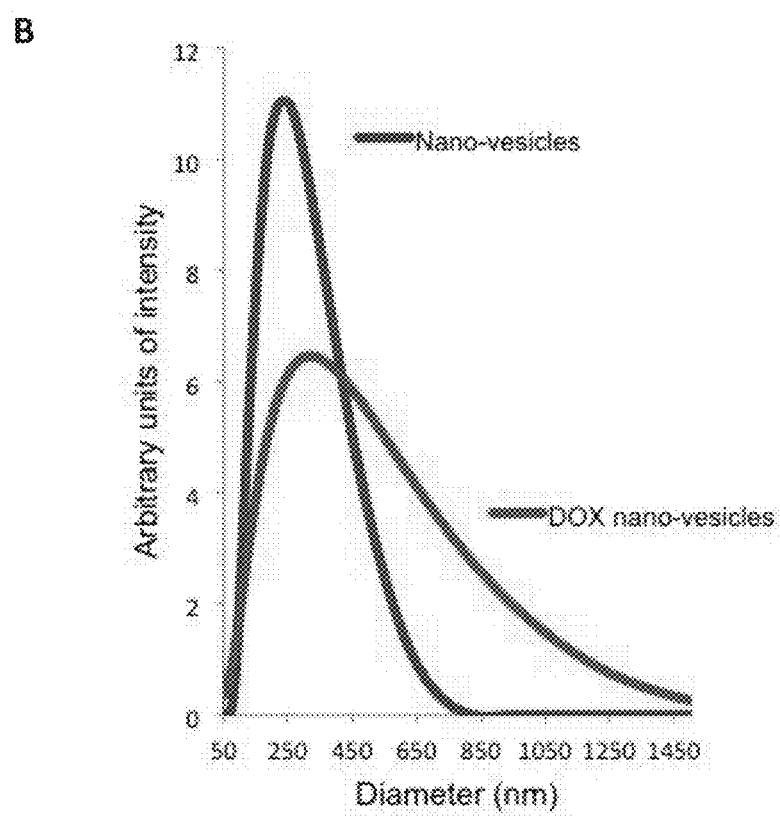

Turning now to FIG. 18, which shows non-limiting examples to assess the drug-loading of EVs in accordance with embodiments. Specifically, to assess the DOX-loading of EL4-derived EVs, the EVs were loaded with DOX via incubation with 1 mg/mL of DOX for 12 hours prior to purification with 30 kDa centrifugal filters. The filter size was selected to be more than sufficient to isolate EVs while still removing free proteins and DOX. Initial studies with 30 kDa centrifugal filtration showed that a single filtration step led to removal of more than 85% of protein from the original sample (FIG. 18A). This high protein loss indicates that the method should be sufficient for removal of free protein and free drug from samples of EVs loaded with DOX (herein called DOX-EVs). The size of the DOX-EVs was further assessed via DLS (FIG. 18B). DLS identified that the DOX-EVs range in size from 50 nm to several hundreds of nanometers in diameter (FIG. 18B). Representative TEM images of DOX-EVs can be seen in FIG. 11, where FIG. 11A shows the supernatant of EL4 cells, which have not been subjected to sulfhydryl blocking reagents; FIG. 11B shows EL4-derived unloaded EVs, and FIG. 11C shows DOX-EVs.

Figure 19:
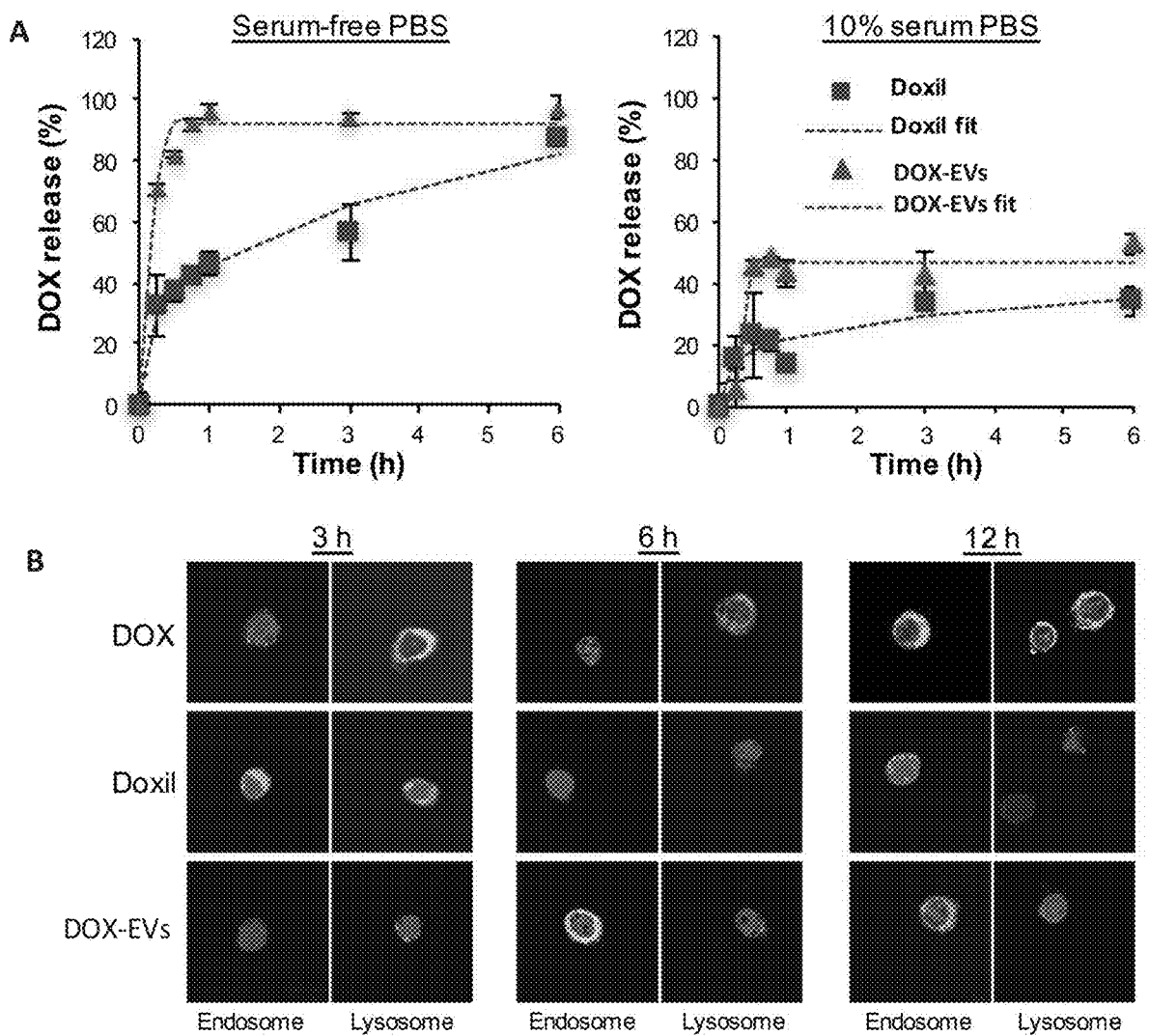
FIG. 19A is a pair of data graphs depicting DOX release in PBS with or without serum, comparing DOXIL and DOX-loaded extracellular vesicles in support of various embodiments of the invention.
FIG. 19B is a composite of confocal microscope images depicting EL4 cells treated with DOX, DOXIL or DOX-loaded extracellular vesicles, and fluorescently labelled for endosomes or lysosomes generated to support various embodiments of the invention.

Turning now to FIG. 19, EVs produced in accordance with various embodiments may show different release and uptake characteristics from other forms of drug delivery. Specifically, FIG. 19 shows DOX release from and uptake. Specifically, FIG. 19A demonstrates the release of DOX from DOX-EVs with and without serum added to PBS buffer as compared to the release of DOX from liposomal DOX (DOXIL). DOX-EVs release drug at a much more rapid rate than DOXIL. In fact, DOX-EVs show a more rapid release profile than DOXIL in both serum-free media (FIG. 19A, left panel) and in serum-containing media (FIG. 19B, right panel). Drug release reached 50% of the maximum at 51, 13, 23, and 10 minutes for DOXIL and DOX-EVs in serum-free media and DOXIL and DOX-EVs in serum-containing media, respectively.

Similarly, DOX-EVs were taken up by cells more rapidly than DOXIL (FIG. 19B). FIG. 19B shows EL4 cells incubated with 100 mg/mL of DOX, DOXIL, and DOX-EVs after 3, 6, and 12 hours prior to confocal imaging. In FIG. 19B, endosomes were stained with CellLight Early Endosomes-GFP and lysosomes were stained with LysoTracker Green DND-26. A representative image is shown for each time point. While DOXIL shows minimal uptake over the timeframe shown, DOX-EVs are taken up in the endosome within 6 hours and drug appears in the nucleus by 12 hours. EL4 cells treated with DOX-EVs for up to 12 hours exhibit DOX fluorescence in the cytoplasm while DOXIL treated cells do not.

Figure 20:
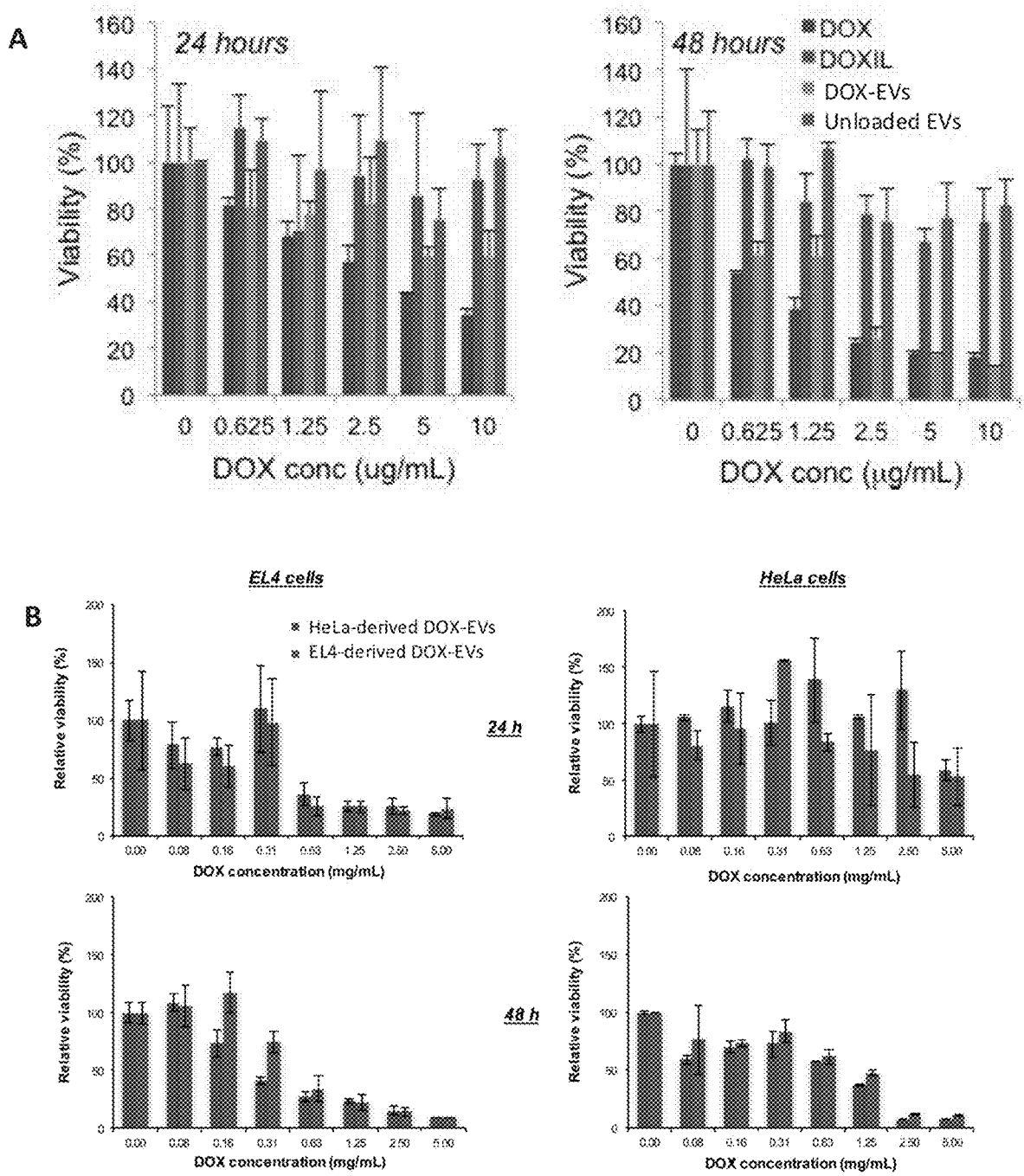
FIG. 20A is a pair of data graphs depicting the viability of EL4 cells treated with DOX, DOXIL, DOX-loaded extracellular vesicles, and unleaded extracellular vesicles in support of various embodiments of the invention.
FIG. 20B is a quartet of data graphs depicting the viability of EL4 and HeLa cells treated with DOX-loaded extracellular vesicles derived from both EL4 and HeLa cells in support of various embodiments of the invention.

Turning now to FIG. 20. FIG. 20 describes the effect of therapeutic agents delivered by EVs of various embodiments as compared to other forms of drug delivery. Specifically, FIG. 20 shows the viability of EL4 cells was assessed using an MTT assay in triplicate (n=3), and error bars show standard deviation. At the highest concentrations tested, DOX and DOX-EVs were statistically significant (p<0.01) from the controls as analyzed by a one-way ANOVA and the Tukey HSD post-hoc test. Although the mechanism behind the superior uptake of DOX-EVs compared to DOXIL has not been studied in this work, it is mores likely related to the PEGylatio of DOXIL. PEGylation has been shown to sterically stabilize liposomes allowing for slower release and uptake. (See, Immordino, et al., Int. J. Nanomedicine 1, 297-315 (2016), the disclosures being incorporated herein by reference.)

FIG. 20A shows the results of an in vitro MTT assay to test the viability of EL4 cells treated with DOX-loaded EVs. EL4 cells were treated over 24 or 48 hours with DOX, DOXIL, DOX-EVs, or unloaded EVs. The results show that there are some significant differences between cells treated over 24 hours and those treated over 48 hours. After a 24-hour treatment, DOX-loaded EVs do not perform as well as free DOX, but they seem to "catch up" over the longer incubation time. It is important to note that DOX-loaded EVs would not be expected to outperform free DOX in in in vitro study since their primary benefits (improved biocompatibility and extended release) are critical factors in an in vivo delivery setting.

FIG. 20B shows the effect of DOX-loaded HeLa-derived EVs and EL4-derived EVs at varying concentrations of DOX on both HeLa and EL4 cells. Interestingly, the cell lines did not show a preference for the EVs derived from other cell lines.

Figure 21:
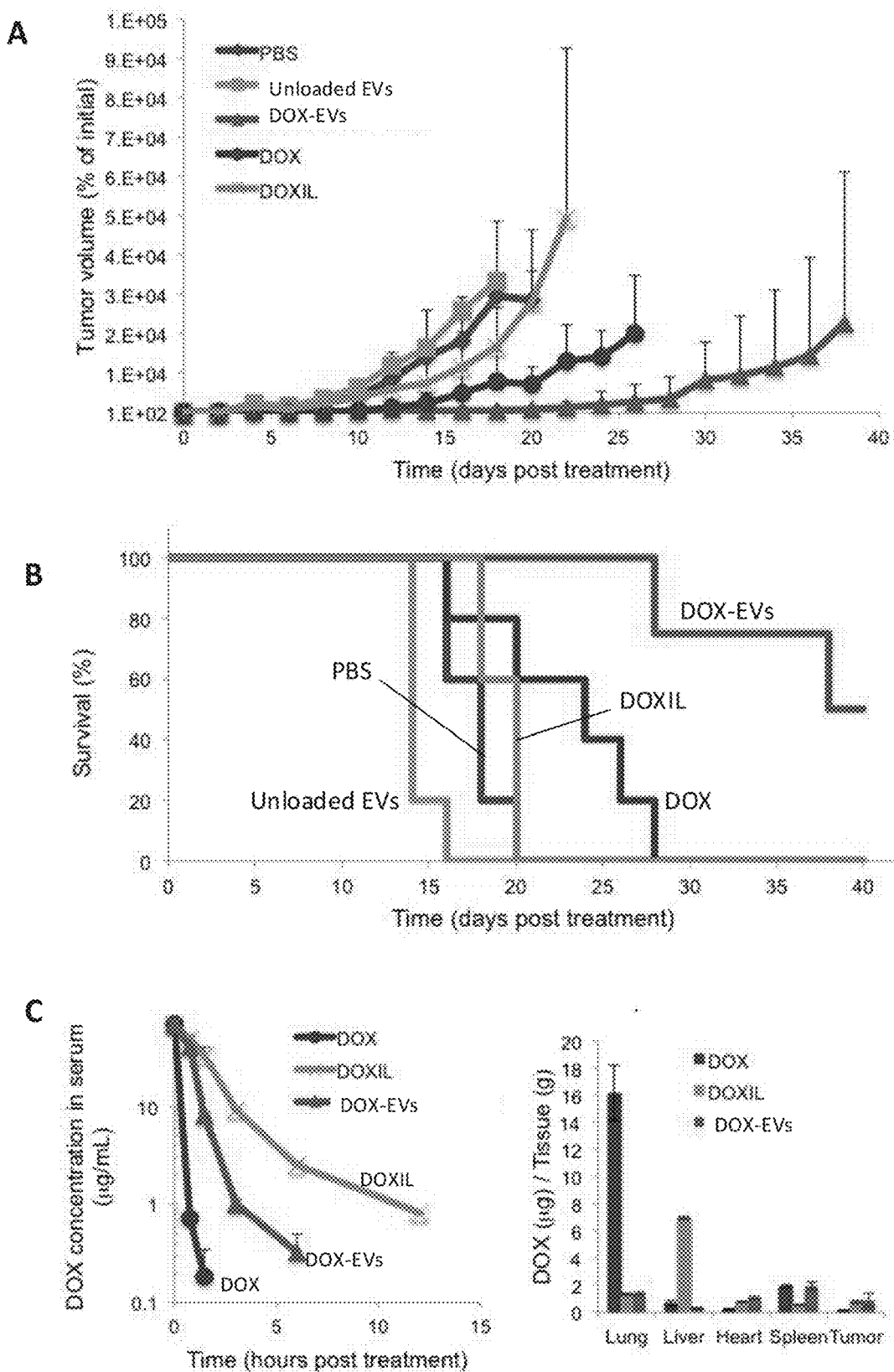
FIG. 21A is a data graph depicting tumor volume treated with PBS, unloaded extracellular vesicles, DOX-loaded extracellular vesicles, DOX, and DOXIL, in support of various embodiments of the invention.
FIG. 21B is a data graph depicting a survival curve of mice having tumors treated with PBS, unloaded extracellular vesicles, DOX-loaded extracellular vesicles, DOX, and DOXIL, PBS, unloaded extracellular vesicles, DOX-loaded extracellular vesicles, DOX, and DOXIL, in support of various embodiments of the invention.
FIG. 21C is a pair of data graphs depicting the level of DOX, DOXIL, and DOX-loaded extracellular vesicles in the serum, lung, liver, heart, spleen, and tumor of treated mice PBS, unloaded extracellular vesicles, DOX-loaded extracellular vesicles, DOX, and DOXIL, in support of various embodiments of the invention.

Turning now to FIG. 21. FIG. 21 describes the effect of therapeutic agents delivered by EVs of various embodiments as compared to other forms of drug delivery. Specifically, data from in vivo studies showing the efficacy of DOX are shown in FIG. 21. In these studies, EL4 tumors were established in C57BL/6 mice eight days before treatment. Treatment began on Day 0, where an equivalent DOX concentration of 8 mg/kg was given to the mice via intravenous injection into the tail vein. FIG. 21A shows that DOX-EVs provided the slowest tumor growth, indicating that DOX-EVs were more effective than free DOX or DOXIL in decreasing tumor size. FIG. 21B shows that DOX-EVs also provided the highest survival rate among the mice.

Turning to FIG. 21C, serum was collected from C57BL/6 mice treated with DOX, DOXIL or DOX-EVs and analyzed for drug content. Concentration of DOX in the serum (n=3) was measured over 12 hours by a series of blood collections and fluorescence quantifications. Both DOXIL and DOX-EVs remain in the serum longer than free DOX (FIG. 21C, left panel). Most likely due to the protective effect of PEGylation, DOXIL has a longer circulation time than DOX-EVs. Twenty-four hours after treatment, the mice were sacrificed and their organs were assessed for drug content. FIG. 21C, right panel, shows that free DOX tends to accumulate in the lung while DOXIL has a tendency to be cleared by the liver. DOX-EVs, on the contrary, show minimal accumulation in lung, liver, and all other tissue examined.

In the past decade, the goal of developing biocompatible, targeting nano-carriers in the form of EVs has become the goal of many researchers in the field therapeutic delivery. The theoretical process would involve isolating EVs from primary cells derived from a patient and then using those EVs as a therapeutic carrier for delivery of cargo to a specific site in the original patient's body. A key challenge in achieving this goal is the successful production of therapeutically effective levels of EVs. (See, Smith, J. A. et al. Bioprocess Int. 13, 1-13 (2015), the disclosure of which is incorporated herein by reference.) These procedures provide a relatively simple and highly scalable protocol for producing large quantities of nano-sized EVs.

Cell-derived EVs are expected to have lower immunogenicity than polymeric, viral, or lipid-based carriers. Additionally, the DOX-EVs accumulate less in the liver and lungs than DOX and DOXIL. This may be in part related to their small size; their average diameter is half that of liposomal DOX. It could also be due to vesicles' ability to specifically associate with cells from the line that they were derived from. These biodistribution characteristics result in highly improved survival outcomes for tumor-bearing mice treated with DOX-EVs compared to the controls (50% survival versus 0% survival over 40 days, FIG. 21B).

Although the exemplary data shown here use DOX-delivery vehicles for cancer therapy, EVs have a broad range of potential health applications. A wide variety of therapeutics have poor biodistribution which could be improved by delivery via EVs. Additionally, EVs could also be utilized to improve delivery of RNAs for gene therapy applications. EVs are highly promising to the field of therapeutic delivery, and the described method for scalable mass production could allow them to reach their potential in the field.

Embodiments of EVs for Therapy, including Immunotherapy

Some embodiments of the present disclosure may be used to elicit an immune response, signal a reaction, or produce any other form of response in an individual. These responses may be produced by the EV itself or elicited by the display of surface moieties on EVs. These surface moieties may include antigens, receptors, antibodies, chemically labeled, or conjugated molecules of interest, or any other form of moiety which may be displayed on a cell membrane. Conjugated molecules of interest may include small molecules, polymers, inorganic materials or any combination thereof. These surface moieties may be made of proteins, carbohydrates, lipids, nucleic acids, small molecules, inorganic materials, or any type of molecule that may be produced by a cell or labeled or conjugated prior to, concurrently with, after, or any combination thereof of EV production. These surface moieties may be artificially placed on the surface of a cell prior to vesiculation, during vesiculation, after vesiculation, or any combination of prior to, during, or after vesiculation. In some embodiments, the displaying of surface moieties may occur artificially through an act such as pulsing, heat shock, electroporation, covalent conjugation, and noncovalent coating, or any other method or combination of methods to place surface moieties on a plasma membrane. In other embodiments, the displaying of surface moieties may occur through a natural process, such as inducing a cell to produce the surface moieties and locating them on the plasma membrane. In some embodiments, some surface moieties may be loaded in combination with other agents of interest as described within this disclosure. In such situations, it may be beneficial to conduct multiple loading steps, where surface moieties may be loaded prior to vesiculation and other agents of interest, including additional surface moieties, may be loaded during or after vesiculation. Additionally, the surface moieties may be loaded after the loading of an agent of interest, such that an agent of interest, including surface moieties, may be loaded prior to vesiculation, while additional surface moieties may be loaded during or after vesiculation. Using EVs alone or an EV displaying a surface moiety, may be important for applications such as immune transplant rejection or multiple sclerosis.

Figure 22:
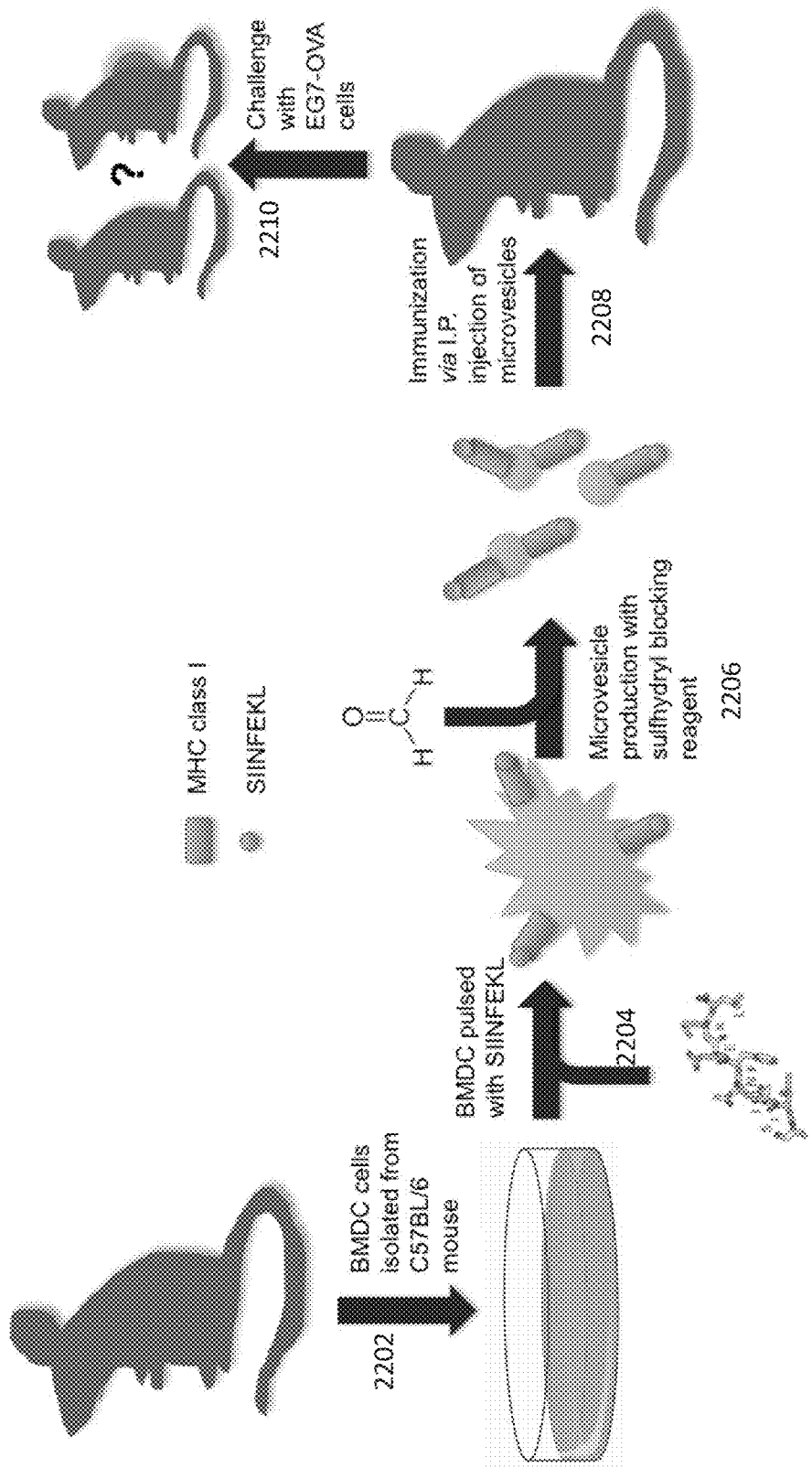
FIG. 22 illustrates a process for immunizing a treatment subject against tumor-causing cells using SIINFEKL-presenting extracellular vesicles in accordance with an embodiment of the invention.

FIG. 22 demonstrates an example of one strategy to elicit an immune response in an individual in accordance with various embodiments. It should be noted that FIG. 22 is only exemplary and does not describe all possible ways to elicit an immune response in an individual in accordance with embodiments of the present invention. Specifically, FIG. 22 demonstrates an example of the delivery of an EV displaying specific antigens, to create an immune response. In FIG. 22, cells may be isolated from an individual (2202). These cells may be manipulated in a way to display an antigen of choice (2204) prior to inducing vesiculation (2206) to produce EVs displaying the antigen. These antigen-displaying EVs may be administered to an individual (2208) to generate an immune response, when the individual is immune-challenged by something displaying the same antigen (2210).

Specifically, FIG. 22 describes a method of several embodiments where bone marrow dendritic cells (BMDC) were used for immunotherapy, especially in the field of cancer. EVs derived via exposing BMDCs to sulfhydryl blocking reagents can be used for cancer immunotherapy in the form of a cell-free vaccine. Dendritic cells (DCs) activate T cells against antigens, and therefore can be used for developing an immunization against antigens, including cancer-specific antigens. A common laboratory model for cancer immunotherapy relies on E.G7-OVA cells, a lymphoma cell line which expresses the antigen SIINFEKL. EVs from SIINFEKL-presenting BMDCs were produced to use as a model vaccine against E.G7-OVA. DC-derived exosomes have been shown to be an alternative to DC adoptive therapy. Vesiculation, in accordance with embodiments of processes described herein, would enable a more efficiently produced cell-free vaccine than is currently available using exosomes.

In the method described by FIG. 22, BMDC were isolated from C57BL/6 mice (2202). These cells were pulsed in the presence of the SIINFEKL antigen to cause the cells to display the antigen (2204). The BMDC cells were treated with sulfhydryl blocking reagents (2206) to produce EVs displaying the SIINFEKL antigen. The SIINFEKL-displaying EVs were administered to a mouse (2208) through an intraperitoneal injection (2208). The mouse was further challenged to with EG7-OVA cells (2210) to assess efficacy of using antigen-displaying EVs to produce an immune response.

In embodiments of EV for use for immunotherapy, the EVs may be loaded with a surface moiety by incubating cells or empty EVs with 25 μg/mL, 50 μg/mL, 100 μg/mL, 200 μg/mL, 300 μg/mL, 400 μg/mL, or 500 μg/mL concentration of the surface moiety. Additionally, the incubation may occur for 1 hour, 2 hours, 3 hours, 4 hours, 5 hours, 6 hours, 12 hours, 24 hours, or 48 hours. Alternatively, the loading conditions may occur at a ratio of EVs to a surface moiety of 1:0.1, 1:0.2, 1:0.3, 1:0.4, 1:0.5, 1:0.6, 1:0.7, 1:0.8, 1:0.9, 1:1, 1:2, 1:2, 1:3, 1:4, 1:5, 1:6, 1:7, 1:8, 1:9, or 1:10.

Figure 23:
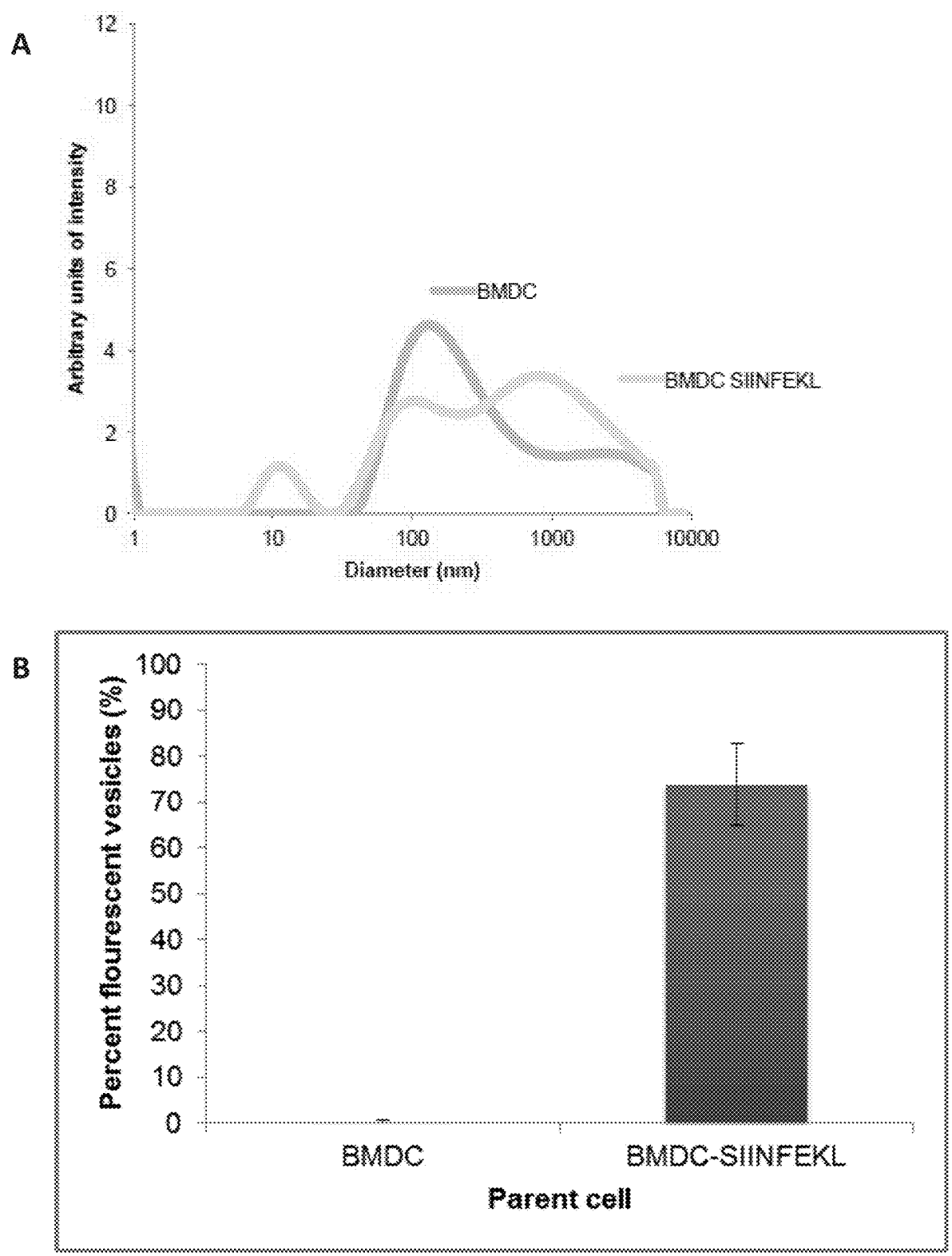
FIG. 23A is a data graph comparing size of unloaded extracellular vesicles with SIINFEKL-presenting extracellular vesicles generated in accordance with various embodiments of the invention.
FIG. 23B is a data graph depicting extracellular vesicles derived from dendritic cells can present the antigen SIINFEKL in accordance with various embodiments of the invention.

Turning now to FIG. 23. FIG. 23 demonstrates how a person may determine the efficacy of loading a surface moiety onto an EV. Specifically, FIG. 23 shows the results of SIINFEKL loading onto EVs are shown. In FIG. 23A, the size distribution of EVs produced from BMDC and BMDC displaying SIINFEKL (BMDC-SIINFEKL) as measured by DLS.

In FIG. 23B, the presentation of the antigen SIINFEKL by EVs was examined. BMDC cells (either pulsed with SIINFEKL at 1 mg/ml for 1 hour at 37° C. and washed twice or control cells) were vesiculated at 10 mil cells/ml in 10 mL PBS with 180 μl 4% PFA solution and 20 μl 1 M DTT for 4 hours at 37° C. After cell and cell debris removal by centrifugation at 1200 rpm for 5.5 min, micro-sized EVs were concentrated at 13,200 rpm for 10 minutes and redispersed in 100 μl PBS. Vesicles were labeled with fluorescently labeled antibody specific for SIINFEKL for 1 hour at 4° C. and washed twice and then characterized by flow cytometry. Based on forward and side scattering data, micro-sized vesicle gating was set and the percentage of fluorescent micro-sized vesicles was found. FIG. 23B shows the percentage of fluorescent events in the micro-sized vesicle region. Over 70% of SIINFEKL-pulsed BMDC-derived EVs show SIINFEKL presentation.

Additionally, the polydispersity of surface moiety displaying EVs may have a similar polydispersity index (PDI) of unloaded EVs. As such, surface moiety displaying EVs may have a PDI of about 0.1, 0.2, 0.3, 0.4, 0.5, 0.6, 0.7, 0.8, 0.9, or 1.0.

Figure 24:
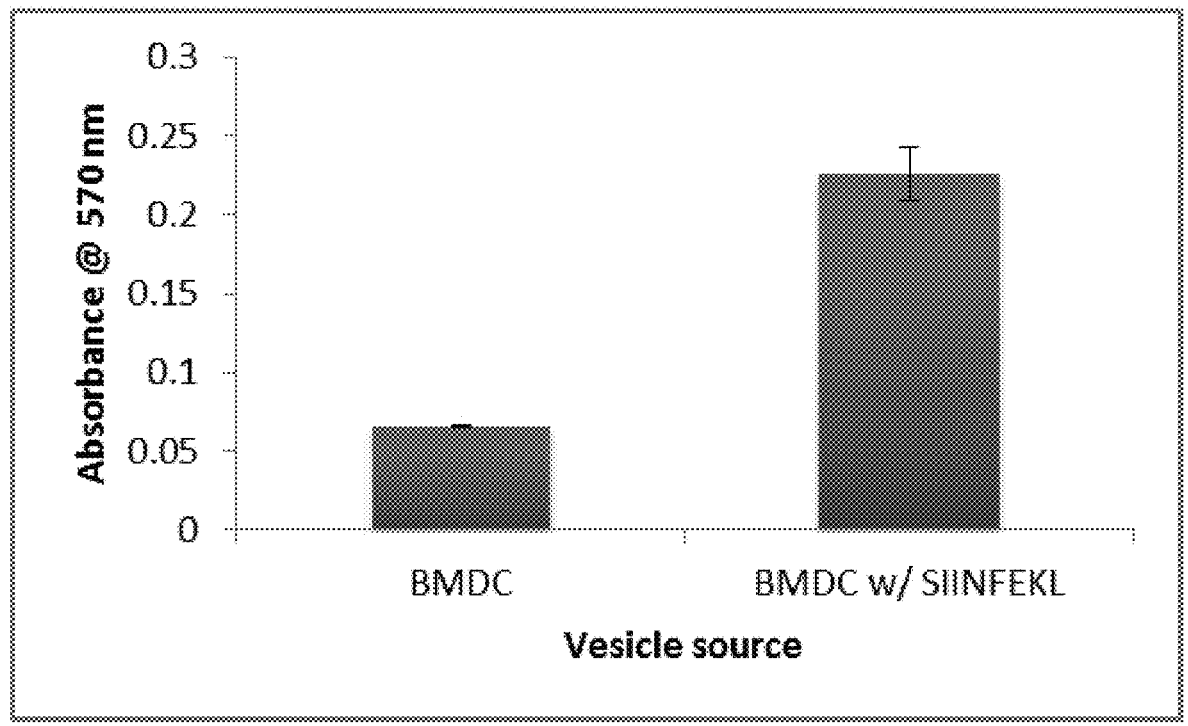
FIG. 24 is a data graph depicting the activation of T-cells by extracellular vesicles presenting the antigen SIINFEKL in accordance with various embodiments of the invention.

Turning now to FIG. 24, showing how the efficacy of EVs loaded with surface moieties may be at eliciting an immune response. Specifically, FIG. 24 demonstrates the ability of these EVs to activate T-cells after determining EVs presented the antigen SIINFEKL. In embodiments, ten thousand cells of the T-cell line B3Z were plated in 95 μL of media (RPMI) in a 96 well plate. 5 μL of EVs were added and the cells were incubated overnight. (Note that BMDC and BMDC-SIINFEKL EVs were produced from equivalent numbers of BMDC cells.) After removing the media from the cells, a beta-galactosidase assay (CPRG) was performed and absorbance was measured at 570 nm. High activity of beta-galactosidase indicate activation of the T-Cells. Thus, FIG. 24 is an indication that BMDC-SIINFEKL EVs can activate B3Z cells.

Figure 25:
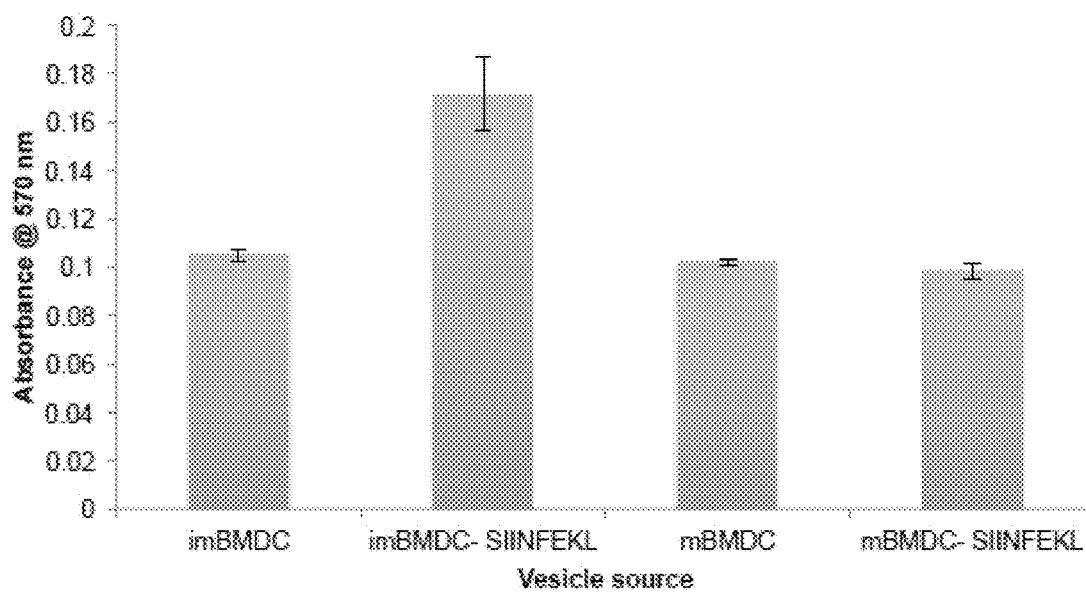
FIG. 25A is a data graph depicting the activation of T-cells by extracellular vesicles derived from immature dendritic cells, immature dendritic cells presenting the SIINFEKL antigen, mature dendritic cells, and mature dendritic cells presenting the SIINFEKL antigen in accordance with various embodiments of the invention.
FIG. 25B is a data graph depicting the level of SIINFEKL presentation on extracellular vesicles derived from immature dendritic cells, immature dendritic cells presenting the SIINFEKL antigen, mature dendritic cells, and mature dendritic cells presenting the SIINFEKL antigen in accordance with various embodiments of the invention.
Figure 25:
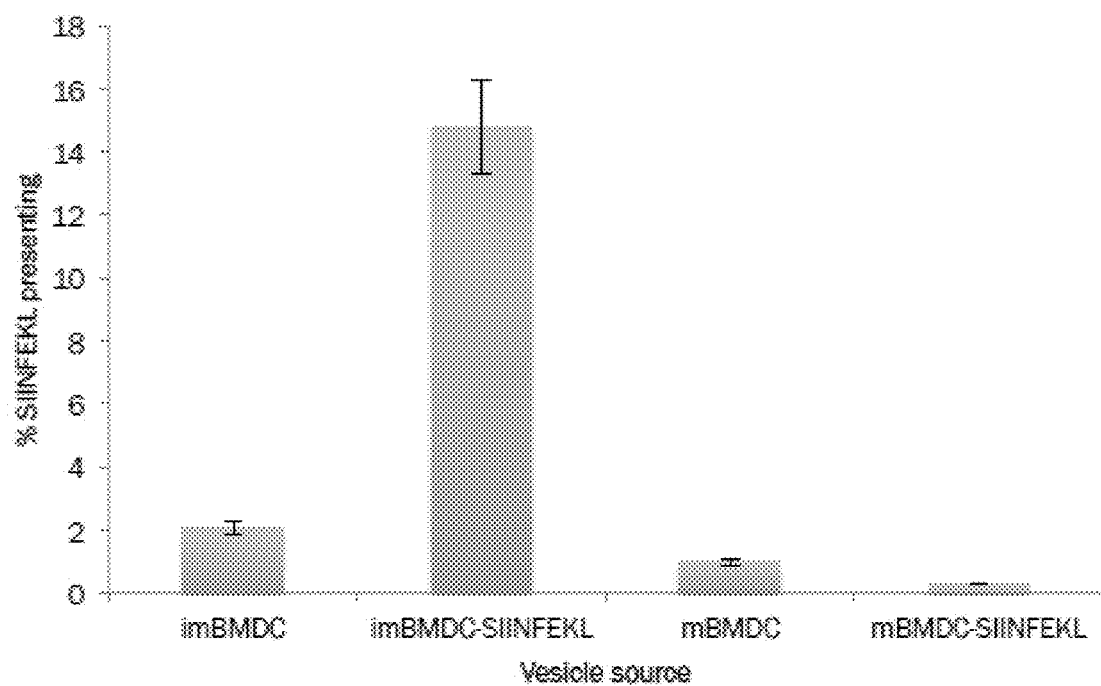

Turning now to FIG. 25, which demonstrates examples where some cells may be more suitable for surface moiety loading than others. Specifically, immature BMDC-SIINFEKL EVs were found to be more effective than other BMDC EVs at eliciting an immune response. FIG. 25A shows data from a CPRG assay describing how mature BMDC-SIINFEKL produced a similar T-cell response to mature BMDC and immature BMDC, while immature BMDC-SIINFEKL cells produced a higher level of response. Following an assay using fluorescently labeled antibodies specific for SIINFEKL, only immature BMDC-SIINFEKL EVs presented the SIINFEKL antigen.

Methods and Materials of Exemplary Embodiments

Cell culture. A mouse lymphoma cell line (EL4) was obtained from the American Type Culture Collection (ATCC) and grown in DMEM (Thermo Fisher Scientific) supplemented with 10% FBS and 1% penicillin-streptomycin. Cell were kept at 37° C. with 5% $CO_2$.

EV production and isolation. 107 cells/mL were incubated with 25 mM paraformaldehyde and 2 mM dithiothreitol in PBS for 6 hours at 37° C. with 5% $CO_2$. To isolate EVs, cells were removed by centrifugation at 1,200 rpm for 5.5 minutes followed by removal of cell debris and micro-sized EVs at 9,300×g for 10 minutes. EVs were concentrated with a 30 kDa centricon (4,500 rpm for 15 minutes); the EV-containing supernatant was concentrated and washed with an equivalent volume of PBS twice.

EV characterization. EV size distribution was characterized by dynamic light scattering analysis using a Malvern Zetasizer. Size was confirmed and structured was analyzed via transmission electron microscopy (TEM). Formvar carbon coated copper grids coated with 10 μL of EVs stained with 1% uranyl acetate were imaged with a Philips/FEI CM-20 Transmission Electron Microscope operated at 200 kV. EVs were quantified using a BCA Protein Assay Kit (Pierce Biotechnology).

Doxorubicin-loading of EVs. EVs (25 μg/mL by protein content) were incubated with DOX (1 mg/mL) in PBS mixing for 12 hours at 37° C. Free drug was removed and EVs were concentrated with a 30 kDa centricon (4,500 rpm for 15 minutes); the collected EVs were washed with an equivalent volume of PBS three times. A sample of vesicles was lysed via sonication for 15 minutes and the drug content was quantified by fluorescence spectroscopy (ex. 485 nm, em. 595 nm).

Doxorubicin release. DOXIL and DOX-loaded EVs were diluted to 10 μg/mL in PBS and kept incubating at 37° C. on a shaking plate. At each time point, a sample was removed and centrifuged with a 30 kDa centricon at 4,500 rpm for 15 minutes. The EVs remaining concentrated on the filter were resuspended in an equivalent volume of PBS and analyzed by florescence spectroscopy (ex. 485 nm, em. 595 nm) to determine the concentration of DOX remaining in the liposomes and EVs.

In vitro viability studies. EL4 cells were plated at 20,000 cells/well in 100 μL of DMEM with 10% FBS. Cells were incubated for 24 hours or 48 hours with the concentrations of DOX, DOXIL or DOX-EVs described in FIG. 20. An MTT assay was performed and cells were incubated with 1 mg/mL of MTT for 1 hour. The crystals were dissolved in 100 μL of DMSO and the absorbance of each well was characterized at 560 nm.

In vivo therapeutic experiments. EL4 tumors were established in the right thighs of 12-week old female C57BL/6 mice by subcutaneous injection of 106 EL4 cells in 100 μL DPBS. After eight days, tumors were clearly visible, and the mice were intravenously injected with a single dose of the treatment of control DPBS in a total volume of 100 μL. Tumor size was measured over 40 days post treatment.

For pharmacokinetics and biodistribution experiments, tumors were established and mice were treated as described above. Tail vein blood collection was completed at the time points indicated and suspended in acidified alcohol. The blood was analyzed for DOX concentration by fluorescence spectroscopy (ex. 485 nm, em. 595 nm). 24 hours post treatment, the mice were sacrificed and the organs were extracted. The organs were cryopulverized and resuspended in acidified alcohol for fluorescence spectroscopy (ex. 485 nm, em. 595 nm) analysis.

Exemplary Embodiments

Biological data supports the generation and characteristic description of the nanovesicles. Furthermore, the data supports the notion that the nanovesicles can be used to a compound delivery system capable as a therapeutic treatment. The following data also details the scalability and enhanced production of nanovesicles from a host source. Accordingly, these data support the various embodiments of the invention as described.

Optimizing Sulfhydryl Blocking to Produce EVs

FIG. 5 describes embodiments of the production of EVs, where the concentrations of sulfhydryl blocking reagents have been altered. Specifically, FIG. 5A demonstrates embodiments where the concentration of paraformaldehyde has been altered to show maximum production levels at 25 mM paraformaldehyde. FIG. 5B shows embodiments where HeLa cells were exposed to various concentrations of sulfhydryl blocking reagents, such that 1×=25 mM paraformaldehyde with 2 mM dithiothreitol. EVs were isolated and quantified using a BCA protein assay. These data show that the production of EVs with HeLa cells is highest at 25 mM paraformaldehyde with 2 mM dithiothreitol, as compared to other concentrations tested.

Collecting and Purifying EVs

In various embodiments, EVs may be collected by any suitable means to separate EVs from cells or cell debris. In some embodiments, to isolate EVs, cells were removed by centrifugation at 1,200 rpm for 5.5 minutes followed by removal of cell debris and micro-sized vesicles at 10,000 rpm for 10 minutes. EVs were concentrated with a 30 kDa centricon (4,500 rpm for 15 minutes); the EV-containing supernatant was concentrated and washed with an equivalent volume of PBS twice. Upon production of EVs in embodiments of this disclosure, formaldehyde residue may be removed using centrifugation, as shown in FIG. 6. The presence of formaldehyde in the resulting EV collection was measured by $^1$H NMR. It should be noted that an embodiment removing formaldehyde by centrifugation is only exemplary, and residue from any added reagents may be removed by any suitable means, including centrifugation, absorption, neutralization, or other means known in the art.

Producing EVs by Sulfhydryl Blocking

FIG. 7 demonstrates an embodiment where the supernatant of vesiculating HeLa cells was analyzed by TEM. HeLa cells treated with paraformaldehyde (PFA) and dithiothreitol (DTT), in accordance with various embodiments of the invention, generate a large amount of EVs as secondarily confirmed by TEM measurements. Since the control (inset) does not show EVs, these nano-sized EVs are unlikely to be exosomes generated by normal cellular processes. Instead, sulfhydryl blocking reagent-induced blebbing results in cells shedding nano-sized EVs. Additionally, FIG. 8 shows a TEM image of EL4 cells treated with and without PFA/DTT. TEM images in FIG. 8A demonstrate that the supernatant from EL4 cells incubated in serum-free/reagent-free media have little or no vesicles, while the EL4 cells incubated with serum-free media containing 25 mM paraformaldehyde and 2 mM dithiothreitol for 4 hours, however, had many nano-sized EVs as indicated by the circles. In order to more clearly examine the EVs, the cells, debris and giant plasma membrane vesicles were removed by centrifugation at 16,100×g. The EVs were then isolated and concentrated by centrifugation at 100,000×g.

EVs are a promising potential therapeutic carrier. Low yield of intrinsic vesicle production is a problem. However, sulfhydryl blocking reagents can be used to produce EVs appropriate in size for carrying therapeutic cargo. FIG. 9 demonstrates embodiments of EV production in the presence and absence of sulfhydryl blocking reagents. EL4 cells were incubated at 100,000 cells/mL in 5 mL of either DMEM (without FBS) for 24 hours or PBS with 90 µL 4% PFA solution and 10 µL 1 M DTT for 2 hours at 37° C. After cells and cell debris were removed by centrifugation at 1200 rpm for 5.5 min, micro-sized vesicles were pelleted at 13,200 rpm for 10 minutes, leaving the EVs in the supernatant. Then, EVs were isolated by 30 kDa centricons at 4,500 rpm for 10 minutes. The EVs were washed three times with 5 mL of DPBS to remove free protein and sulfhydryl blocking reagents. Protein content was assessed using a BCA protein assay (FIG. 9). Vesicles produced from cells that were not exposed to sulfhydryl blocking reagents are called exosomes. Sulfhydryl blocking reagents produce a significantly greater (10-fold) amount of EVs compared to naturally occurring exosomes, based on protein quantification over a significantly shorter time-frame of production.

Determining Stability of EVs

FIG. 10 describes the stability of exosomes versus EVs produced according to certain embodiments. In this figure, the size range of exosomes and EVs of some embodiments are shown as measured by dynamic light scattering (DLS) as measured at 0, 24, and 48 hours. Additionally, the polydispersity index (PDI) shows that as time passes, exosomes increase in polydispersity, while EVs of certain embodiments remain stable. Also, the anionic surface charge of exosomes decreased over time, while EVs of some embodiments remain relatively stable after 24 and 48 hours, when compared to the initial measurement.

Adjusting EV Size for Specific Uses

FIG. 12 shows some embodiments, where phosphate-buffered saline (PBS) may be used along with the sulfhydryl blocking reagents to generate EVs. In this figure, EVs were generated using 25 mM PFA, 2 mM DTT along with PBS at 0.1×, 1×, and 10× concentrations. The size distribution of EVs produced in these embodiments was measured via a DLS assay. The increased concentration of PBS led to smaller EVs produced in some embodiments. These results indicate that the size of EVs produced in some embodiments may be customized to suit specific needs.

Specifically, FIG. 12A demonstrates the effect of increasing the buffer concentration to generate EVs in the 10 nm to 1,000 nm size-range (nano-scale EVs) of some embodiments. Embodiments of nano-scale EVs may be generated by inducing vesiculation in cells, followed by a 30 kDa centrifugal filtration as described in this disclosure. In some embodiments, cells may be removed from the solution by an initial 1,200 rpm centrifugation prior to the 30 kDa centrifugal filtration. Additionally, FIG. 12B demonstrates a similar result showing a linear relationship between increased osmolarity and smaller EVs.

Similarly, FIGS. 12C and 12D demonstrate the effect of increasing the buffer concentration to generate EVs in the 500 nm to greater than 15,000 nm size-range (micro-scale EVs) in other embodiments. Embodiments of micro-scale EVs may be generated by inducing vesiculation in cells followed by centrifugation at 1,200 rpm to remove cells. The remaining supernatant may be further centrifuged at 9,300×g to isolate micro-scale EVs. It should be noted that the supernatant remaining after isolation of micro-scale EVs may also be submitted to a 30 kDa centrifugal filtration to further isolate nano-scale EVs. Images of micro-scale EVs of various embodiments are shown in FIG. 12E. In these images, the size and distribution of micro-scale EVs generated using sulfhydryl blocking reagents along with varying concentrations of PBS are shown.

The size of EVs produced in certain embodiments may also be adjusted by using alternative buffers. FIG. 13A demonstrates the effect of several buffers on the size of EVs produced by some embodiments as measured by DLS. In this figure, the buffers DPBS, DMEM, and GPMV were shown to produce EVs with sulfhydryl blocking in various size ranges, including into the larger, µm-sized EVs.

Additionally, not all buffers produce EVs at the same rate. FIG. 13B demonstrates the production of EVs by various buffers as determined by a BCA assay to assess the protein content. As shown, PBS and DPBS buffers are more efficient than GPMV and DMEM buffers. FIG. 13C demonstrates PDI of EVs produced by PBS and GPMV buffers. As indicated in FIG. 13C, PBS buffer produces EVs with a lower PDI, indicating that PBS creates more uniformly sized EVs over GPMV, which has a PDI of approximately 1, which indicates nearly complete polydispersity of EVs produced with GPMV. Further, FIG. 13D demonstrates nano-sized EVs produced by vesiculation with 0.1 M HEPES buffer and 0.9% saline, which show a very broad size distribution and high polydispersity among these buffers. Similarly, FIG. 13E shows production of micro-sized EVs using 0.1 M HEPES buffer and 0.9% saline, which show a very broad size distribution and high polydispersity among these buffers.

Each of these buffers shown in FIG. 13 may contain various components to balance osmotic pressure as well as supplement cellular growth. The results shown in FIG. 13 indicate that changing osmolarity of the solution is not the only factor in adjusting the average size, size distribution, or production rate of EVs produced by various embodiments.

Assessing Actin Content of EVs

In FIG. 14A, left panel shows a light microscope image of a micro-scale EV being formed from a host cell, while FIG. 14A, right panel shows the presence of actin as stained with a fluorescent dye. Similarly, FIG. 14B overlays a fluorescent image onto a light image to show that EVs produced by some embodiments may be substantially free of actin.

Loading EVs with Doxorubicin

FIG. 17 further demonstrates examples of various conditions for loading EVs with a therapeutic agent in accordance with embodiments of the present invention. Specifically, FIG. 17A demonstrates the production of EVs by incubating EL4 cells with PFA and DTT. EVs produced may be collected by centrifugation. DOX or another therapeutic may be loaded into to the EVs, then collected through centrifugation. EVs have great potential as therapeutic carriers due to their small size and high biocompatibility. The EL4-derived EVs were loaded with a common chemotherapeutic drug, doxorubicin (DOX). DOX is known for high instances of cardiotoxicity, and therefore is an ideal candidate for targeted therapeutic delivery. Anticancer agent, DOX, was selected for studies due to its relatively low solubility and bioavailability and subsequent potential for improved biodistribution when delivered via drug-loaded EVs. DOX's intrinsic fluorescence also aids in confirmation of drug entrapment within EVs. DOX, a chemotherapeutic anthracycline antibiotic, exhibits red fluorescence (excitation: 480 nm, emission: 580 nm). Passive DOX loading of EVs was tested at different drug concentrations, temperatures and incubation periods (FIG. 17B). As expected, all three factors factor in DOX loading. Additionally, when the ratio of DOX to EVs was increased, the amount of DOX loaded into EVs also increased (FIG. 17C).

To assess the DOX-loading of EL4-derived EVs, the EVs were loaded with DOX via incubation with 1 mg/mL of DOX for 12 hours prior to purification with 30 kDa centrifugal filters. The filter size was selected to be more than sufficient to isolate EVs while still removing free proteins and DOX. Initial studies with 30 kDa centrifugal filtration showed that a single filtration step led to removal of more than 85% of protein from the original sample (FIG. 18A). This high protein loss indicates that the method should be sufficient for removal of free protein and free drug from samples of EVs loaded with DOX (herein called DOX-EVs). The size of the DOX-EVs was further assessed via DLS (FIG. 18B). DLS identified that the DOX-EVs range in size from 50 nm to several hundreds of nanometers in diameter (FIG. 18B). Representative TEM images of DOX-EVs can be seen in FIG. 11, where FIG. 11A shows the supernatant of EL4 cells, which have not been subjected to sulfhydryl blocking reagents; FIG. 11B shows EL4-derived unloaded EVs, and FIG. 11C shows DOX-EVs.

Assessing EV-delivered Doxorubicin Release, Uptake, and Efficacy

FIG. 19 shows DOX release from and uptake. Specifically, FIG. 19A demonstrates the release of DOX from DOX-EVs with and without serum added to PBS buffer as compared to the release of DOX from liposomal DOX (DOXIL). DOX-EVs release drug at a much more rapid rate than DOXIL. In fact, DOX-EVs show a more rapid release profile than DOXIL in both serum-free media (FIG. 19A, left panel) and in serum-containing media (FIG. 19B, right panel). Drug release reached 50% of the maximum at 51, 13, 23, and 10 minutes for DOXIL and DOX-EVs in serum-free media and DOXIL and DOX-EVs in serum-containing media, respectively.

Similarly, DOX-EVs were taken up by cells more rapidly than DOXIL (FIG. 19B). FIG. 19B shows EL4 cells incubated with 100 mg/mL of DOX, DOXIL, and DOX-EVs after 3, 6, and 12 hours prior to confocal imaging. In FIG. 19B, endosomes were stained with CellLight Early Endosomes-GFP and lysosomes were stained with LysoTracker Green DND-26. A representative image is shown for each time point. While DOXIL shows minimal uptake over the timeframe shown, DOX-EVs are taken up in the endosome within 6 hours and drug appears in the nucleus by 12 hours. EL4 cells treated with DOX-EVs for up to 12 hours exhibit DOX fluorescence in the cytoplasm while DOXIL treated cells do not.

Turning now to FIG. 20. FIG. 20 describes the effect of therapeutic agents delivered by EVs of as compared to other forms of drug delivery. Specifically, FIG. 20 shows the viability of EL4 cells was assessed using an MTT assay in triplicate (n=3), and error bars show standard deviation. At the highest concentrations tested, DOX and DOX-EVs were statistically significant (p<0.01) from the controls as analyzed by a one-way ANOVA and the Tukey HSD post-hoc test. Although the mechanism behind the superior uptake of DOX-EVs compared to DOXIL has not been studied in this work, it is mores likely related to the PEGylatio of DOXIL. PEGylation has been shown to sterically stabilize liposomes allowing for slower release and uptake. (See, Immordino, et al., Int. J. Nanomedicine 1, 297-315 (2016), the disclosures being incorporated herein by reference.)

FIG. 20A shows the results of an in vitro MTT assay to test the viability of EL4 cells treated with DOX-loaded EVs. EL4 cells were treated over 24 or 48 hours with DOX, DOXIL, DOX-EVs, or unloaded EVs. The results show that there are some significant differences between cells treated over 24 hours and those treated over 48 hours. After a 24-hour treatment, DOX-loaded EVs do not perform as well as free DOX, but they seem to "catch up" over the longer incubation time. It is important to note that DOX-loaded EVs would not be expected do outperform free DOX in in vitro study since their primary benefits (improved biocompatibility and extended release) are critical factors in an in vivo delivery setting.

FIG. 20B shows the effect of DOX-loaded HeLa-derived EVs and EL4-derived EVs at varying concentrations of DOX on both HeLa and EL4 cells. Interestingly, the cell lines did not show a preference for the EVs derived from other cell lines.

Turning now to FIG. 21. FIG. 21 describes the effect of therapeutic agents delivered by EVs as compared to other forms of drug delivery. Specifically, data from in vivo studies showing the efficacy of DOX are shown in FIG. 21. In these studies, EL4 tumors were established in C57BL/6 mice eight days before treatment. Treatment began on Day 0, where an equivalent DOX concentration of 8 mg/kg was given to the mice via intravenous injection into the tail vein. FIG. 21A shows that DOX-EVs provided the slowest tumor growth, indicating that DOX-EVs were more effective than free DOX or DOXIL in decreasing tumor size. FIG. 21B shows that DOX-EVs also provided the highest survival rate among the mice.

Turning to FIG. 21C, serum was collected from C57BL/6 mice treated with DOX, DOXIL or DOX-EVs and analyzed for drug content. Concentration of DOX in the serum (n=3) was measured over 12 hours by a series of blood collections and fluorescence quantifications. Both DOXIL and DOX-EVs remain in the serum longer than free DOX (FIG. 21C, left panel). Most likely due to the protective effect of PEGylation, DOXIL has a longer circulation time than DOX-EVs. Twenty-four hours after treatment, the mice were sacrificed and their organs were assessed for drug content. FIG. 21C, right panel, shows that free DOX tends to accumulate in the lung while DOXIL has a tendency to be cleared by the liver. DOX-EVs, on the contrary, show minimal accumulation in lung, liver, and all other tissue examined.

In the past decade, the goal of developing biocompatible, targeting nano-carriers in the form of EVs has become the goal of many researchers in the field therapeutic delivery. The theoretical process would involve isolating EVs from primary cells derived from a patient and then using those EVs as a therapeutic carrier for delivery of cargo to a specific site in the original patient's body. A key challenge in achieving this goal is the successful production of therapeutically effective levels of EVs. (See, Smith, J. A. et al. Bioprocess Int. 13, 1-13 (2015), the disclosure of which is incorporated herein by reference.) These procedures provide a relatively simple and highly scalable protocol for producing large quantities of nano-sized EVs.

Cell-derived EVs are expected to have lower immunogenicity than polymeric, viral, or lipid-based carriers. Additionally, the DOX-EVs accumulate less in the liver and lungs than DOX and DOXIL. This may be in part related to their small size; their average diameter is half that of liposomal DOX. It could also be due to vesicles' ability to specifically associate with cells from the line that they were derived from. These biodistribution characteristics result in highly improved survival outcomes for tumor-bearing mice treated with DOX-EVs compared to the controls (50% survival versus 0% survival over 40 days, FIG. 21B).

Loading of Surface Moieties on EVs

FIG. 23 shows the results of SIINFEKL loading onto EVs are shown. In FIG. 23A, the size distribution of EVs produced from BMDC and BMDC displaying SIINFEKL (BMDC-SIINFEKL) as measured by DLS.

In FIG. 23B, the presentation of the antigen SIINFEKL by EVs was examined. BMDC cells (either pulsed with SIINFEKL at 1 mg/ml for 1 hour at 37° C. and washed twice or control cells) were vesiculated at 10 mil cells/ml in 10 mL PBS with 180 μl 4% PFA solution and 20 μl 1 M DTT for 4 hours at 37° C. After cell and cell debris removal by centrifugation at 1200 rpm for 5.5 min, micro-sized EVs were concentrated at 13,200 rpm for 10 minutes and redispersed in 100 μl PBS. Vesicles were labeled with fluorescently labeled antibody specific for SIINFEKL for 1 hour at 4° C. and washed twice and then characterized by flow cytometry. Based on forward and side scattering data, micro-sized vesicle gating was set and the percentage of fluorescent micro-sized vesicles was found. FIG. 23B shows the percentage of fluorescent events in the micro-sized vesicle region. Over 70% of SIINFEKL-pulsed BMDC-derived EVs show SIINFEKL presentation.

FIG. 24 demonstrates the ability of these EVs to activate T-cells after determining EVs presented the antigen SIINFEKL. In embodiments, ten thousand cells of the T-cell line B3Z were plated in 95 μL of media (RPMI) in a 96 well plate. 5 μL of EVs were added and the cells were incubated overnight. (Note that BMDC and BMDC-SIINFEKL EVs were produced from equivalent numbers of BMDC cells.) After removing the media from the cells, a beta-galactosidase assay (CPRG) was performed and absorbance was measured at 570 nm. High activity of beta-galactosidase indicate activation of the T-Cells. Thus, FIG. 24 is an indication that BMDC-SIINFEKL EVs can activate B3Z cells.

FIG. 25 demonstrates that immature BMDC-SIINFEKL EVs were found to be more effective than other BMDC EVs at eliciting an immune response. FIG. 25A shows data from a CPRG assay describing how mature BMDC-SIINFEKL produced a similar T-cell response to mature BMDC and immature BMDC, while immature BMDC-SIINFEKL cells produced a higher level of response. Following an assay using fluorescently labeled antibodies specific for SIINFEKL, only immature BMDC-SIINFEKL EVs presented the SIINFEKL antigen.

Doctrine of Equivalents

While the above description contains many specific embodiments of the invention, these should not be construed as limitations on the scope of the invention, but rather as an example of one embodiment thereof. Accordingly, the scope of the invention should be determined not by the embodiments illustrated, but by the appended claims and their equivalents.

What is claimed is:

1. A composition for the delivery of a medicament, comprising:
sulfhydryl blocking reagent induced extracellular vesicles derived from a mammalian cell that are loaded with a medicament, wherein the sulfhydryl blocking reagent induced extracellular vesicles are substantially free of a nuclear component and have an average diameter of between 10 nm and 10000 nm, and wherein the sulfhydryl blocking reagent induced extracellular vesicles have a PDI of less than 0.5.

2. The composition of claim 1, wherein the mammalian cell is selected from the group consisting of a primary cell, a cell derived from a cell line, a stem cell, a cancer cell, a dendritic cell presenting an antigen, and a red blood cell.

3. The composition of claim 1, wherein:
the sulfhydryl blocking reagent induced extracellular vesicles have a PDI of less than 0.4.

4. The composition of claim 1, wherein the medicament is selected from a therapeutic agent, or an imaging agent.

5. The composition of claim 1, wherein the extracellular vesicles are induced with a sulfhydryl blocking reagent that is comprised of at least one of a cross-linking reagent and a reducing agent in a phosphate buffered saline.

6. The composition of claim 5, wherein the cross-linking reagent is selected from the group consisting of formaldehyde and paraformaldehyde and the reducing agent is selected from the group consisting of dithiothreitol, cysteine, and glutathione.

7. The composition of claim 6, wherein the cross-linking reagent is paraformaldehyde; and the reducing agent is dithiothreitol.

8. The composition of claim 5, wherein the phosphate buffered saline is used at a 1× to 10× buffer concentration.

9. The composition of claim 1, wherein the sulfhydryl blocking reagent induced extracellular vesicles are substantially free of actin.

10. The composition of claim 1, wherein the sulfhydryl blocking reagent induced extracellular vesicles have an average diameter of between 10 nm and 200 nm.

11. The composition of claim 1, wherein the sulfhydryl blocking reagent induced extracellular vesicles are stable for at least 6 hours at 37° C.

12. The composition of claim 1, wherein the composition is formulated for local delivery or systemic delivery.

13. The composition of claim 1, wherein the composition is formulated for intravenous delivery.

14. The composition of claim 1, wherein the therapeutic agent is an anticancer agent.

15. The composition of claim 1, wherein the therapeutic agent is doxorubicin.

16. The composition of claim 1, wherein the composition is formulated for the delivery of the compound to a human patient.

17. The composition of claim 16, wherein the mammalian cell is a primary cell from the human patient.

18. A method to treat a subject in need thereof, comprising administering the composition of claim 1 to the subject.

19. The method of claim 18, wherein the composition is administered at the site of a tumor.

20. The method of claim 18, wherein administering the composition results in at least one of the following: activation of T cells and stimulation of an immune response.

* * * * *